(12) United States Patent
Barzel et al.

(10) Patent No.: US 12,031,146 B2
(45) Date of Patent: *Jul. 9, 2024

(54) GENOME EDITING WITHOUT NUCLEASES

(71) Applicant: The Board of Trustees of the Leland Stanford Junior University, Stanford, CA (US)

(72) Inventors: Adi Barzel, Palo Alto, CA (US); Mark A. Kay, Los Altos, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 306 days.

This patent is subject to a terminal disclaimer.

(21) Appl. No.: 17/322,561

(22) Filed: May 17, 2021

(65) Prior Publication Data

US 2021/0277419 A1 Sep. 9, 2021

Related U.S. Application Data

(63) Continuation of application No. 17/067,236, filed on Oct. 9, 2020, now abandoned, which is a continuation of application No. 16/801,531, filed on Feb. 26, 2020, now abandoned, which is a continuation of application No. 15/126,860, filed as application No. PCT/US2015/021501 on Mar. 19, 2015, now Pat. No. 10,612,041.

(60) Provisional application No. 62/045,451, filed on Sep. 3, 2014, provisional application No. 62/044,145, filed on Aug. 29, 2014, provisional application No. 61/969,709, filed on Mar. 24, 2014, provisional application No. 61/969,013, filed on Mar. 21, 2014.

(51) Int. Cl.
| | |
|---|---|
| *A61K 39/00* | (2006.01) |
| *A61K 38/18* | (2006.01) |
| *A61K 39/395* | (2006.01) |
| *A61K 48/00* | (2006.01) |
| *C07K 14/705* | (2006.01) |
| *C07K 14/71* | (2006.01) |
| *C07K 14/715* | (2006.01) |
| *C07K 16/10* | (2006.01) |
| *C07K 16/28* | (2006.01) |
| *C12N 5/0783* | (2010.01) |
| *C12N 9/64* | (2006.01) |
| *C12N 15/00* | (2006.01) |
| *C12N 15/52* | (2006.01) |
| *C12N 15/86* | (2006.01) |
| *C12N 15/90* | (2006.01) |

(52) U.S. Cl.
CPC .......... *C12N 15/86* (2013.01); *A61K 38/1866* (2013.01); *A61K 48/0008* (2013.01); *A61K 48/005* (2013.01); *C07K 16/1045* (2013.01); *C12N 9/644* (2013.01); *C12N 15/52* (2013.01); *C12N 15/907* (2013.01); *C12Y 304/21022* (2013.01); *C07K 2317/76* (2013.01); *C07K 2319/92* (2013.01); *C12N 2750/14143* (2013.01); *C12N 2799/025* (2013.01); *C12N 2800/24* (2013.01); *C12N 2840/20* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 5,139,941 | A | 8/1992 | Muzyczka et al. |
| 5,173,414 | A | 12/1992 | Lebkowski et al. |
| 5,222,982 | A | 6/1993 | Ommaya |
| 5,385,582 | A | 1/1995 | Ommaya |
| 5,667,998 | A | 9/1997 | Dougherty et al. |
| 5,981,214 | A | 11/1999 | Skoultchi |
| 6,093,392 | A | 7/2000 | High et al. |
| 6,140,081 | A | 10/2000 | Barbas |
| 6,453,242 | B1 | 9/2002 | Eisenberg et al. |
| 6,491,907 | B1 | 12/2002 | Rabinowitz et al. |
| 6,534,261 | B1 | 3/2003 | Cox, III et al. |
| 6,936,243 | B2 | 8/2005 | Snyder et al. |
| 6,951,758 | B2 | 10/2005 | Ferrari et al. |
| 7,271,002 | B2 | 9/2007 | Kotin et al. |
| 7,361,639 | B2 | 4/2008 | Xia |
| 7,439,065 | B2 | 10/2008 | Ferrari et al. |
| 7,485,291 | B2 | 2/2009 | Fang et al. |
| 7,714,119 | B2 | 5/2010 | Fang et al. |

(Continued)

FOREIGN PATENT DOCUMENTS

| | | |
|---|---|---|
| EP | 0981604 | 3/2000 |
| EP | 1005376 | 6/2000 |

(Continued)

OTHER PUBLICATIONS

Abremski et al. (1984) "Bacteriophage P1 site-specific recombination. Purification and properties of the Cre recombinase protein" The Journal of Biological Chemistry 259 1509-1514.

(Continued)

*Primary Examiner* — Robert M Kelly
(74) *Attorney, Agent, or Firm* — Bozicevic, Field & Francis LLP; Kyle A. Gurley

(57) ABSTRACT

Methods and compositions are provided for editing the genome of a cell without the use of an exogenously supplied nuclease. Aspects of the methods include contacting a cell with a targeting vector comprising nucleic acid sequence to be integrated into the target locus, where the cell is not also contacted with a nuclease. In addition, reagents, devices and kits thereof that find use in practicing the subject methods are provided.

21 Claims, 26 Drawing Sheets
Specification includes a Sequence Listing.

(56) References Cited

U.S. PATENT DOCUMENTS

| | | | |
|---|---|---|---|
| 7,888,121 | B2 | 2/2011 | Urnov et al. |
| 7,972,854 | B2 | 7/2011 | Miller et al. |
| 7,972,856 | B2 | 7/2011 | Russell et al. |
| 7,998,734 | B2 | 8/2011 | High et al. |
| 8,030,065 | B2 | 10/2011 | Gray |
| 8,846,387 | B2 | 9/2014 | Russell et al. |
| 8,865,881 | B2 | 10/2014 | Balazs et al. |
| 9,045,763 | B2 | 6/2015 | DeKelver et al. |
| 9,175,280 | B2 | 11/2015 | Gregory et al. |
| 9,315,825 | B2 | 4/2016 | Wilson et al. |
| 9,376,685 | B2 | 6/2016 | DeKelver et al. |
| 2003/0147853 | A1 | 8/2003 | McClelland et al. |
| 2003/0162188 | A1 | 8/2003 | Dekelver et al. |
| 2004/0208846 | A1 | 10/2004 | Zhang |
| 2005/0075492 | A1 | 4/2005 | Chen et al. |
| 2005/0142581 | A1 | 6/2005 | Griffey et al. |
| 2005/0266000 | A1 | 12/2005 | Bond et al. |
| 2005/0266552 | A1 | 12/2005 | Doench et al. |
| 2005/0272923 | A1 | 12/2005 | Zhang et al. |
| 2007/0254842 | A1 | 11/2007 | Bankiewicz |
| 2007/0292922 | A1 | 12/2007 | Fang et al. |
| 2008/0081064 | A1 | 4/2008 | Jelle et al. |
| 2008/0299580 | A1 | 12/2008 | Dekelver et al. |
| 2009/0196903 | A1 | 8/2009 | Kliman |
| 2009/0203071 | A1 | 8/2009 | Chen |
| 2009/0241207 | A1 | 9/2009 | Lathe |
| 2009/0263900 | A1 | 10/2009 | Dekelver et al. |
| 2011/0059160 | A1 | 3/2011 | Essner et al. |
| 2011/0065779 | A1 | 3/2011 | Fang et al. |
| 2011/0126303 | A1 | 5/2011 | High et al. |
| 2011/0145940 | A1 | 6/2011 | Voytas et al. |
| 2011/0281361 | A1 | 11/2011 | Dekelver et al. |
| 2013/0117869 | A1 | 5/2013 | Duchateau |
| 2013/0137180 | A1 | 5/2013 | Chen et al. |
| 2013/0203840 | A1 | 8/2013 | Arnould et al. |
| 2013/0280222 | A1 | 10/2013 | Kay et al. |
| 2016/0022838 | A1 | 1/2016 | Gregory et al. |
| 2016/0046915 | A1 | 2/2016 | Wang |
| 2016/0237457 | A1 | 8/2016 | DeKelver et al. |
| 2017/0088856 | A1 | 3/2017 | Barzel et al. |
| 2021/0017539 | A1 | 1/2021 | Barzel et al. |
| 2021/0214752 | A1 | 7/2021 | Kay et al. |
| 2022/0204995 | A1 | 6/2022 | Kay et al. |

FOREIGN PATENT DOCUMENTS

| | | |
|---|---|---|
| EP | 1316319 | 6/2003 |
| EP | 2281050 | 2/2011 |
| EP | 2627665 | 8/2013 |
| JP | 2013527753 | 7/2013 |
| WO | WO 92/01070 | 1/1992 |
| WO | WO 93/03769 | 3/1993 |
| WO | WO 94/016718 | 8/1994 |
| WO | 98/41240 A1 | 9/1998 |
| WO | 98/48005 A1 | 10/1998 |
| WO | WO 98/53058 | 11/1998 |
| WO | WO 98/53059 | 11/1998 |
| WO | WO 98/53060 | 11/1998 |
| WO | WO 99/25840 | 5/1999 |
| WO | WO 99/25841 | 5/1999 |
| WO | WO 02/016536 | 2/2002 |
| WO | WO 03/08045 | 1/2003 |
| WO | WO 03/016496 | 2/2003 |
| WO | WO 2007/056441 | 5/2007 |
| WO | WO 2008/133938 | 11/2008 |
| WO | WO 2009/054985 | 4/2009 |
| WO | WO 2009/131632 | 10/2009 |
| WO | WO 2011/002988 | 1/2011 |
| WO | WO 2011/100058 | 8/2011 |
| WO | WO 011/119773 | 9/2011 |
| WO | WO 2011/130345 | 10/2011 |
| WO | WO 2012/012738 | 1/2012 |
| WO | WO 2012/021632 | 2/2012 |
| WO | 2012/051343 A1 | 4/2012 |
| WO | 2013/119880 A1 | 8/2013 |
| WO | WO 2013/119880 | 8/2013 |
| WO | WO 2013/158309 | 10/2013 |
| WO | WO 2015/143177 | 9/2015 |
| WO | WO 2017/049296 | 3/2017 |

OTHER PUBLICATIONS

Aiello et al. (1979) "Adenovirus 5 DNA sequences present and RNA sequences transcribed in transformed human embryo kidney cells (HEK-Ad-5 or 293)" Virology 94 460.

Aiuti et al. (2002) "Correction of ADA-SCIO by stem cell gene therapy combined with nonmyeloablative conditioning" Science 29:5577 2410-2413.

Al-Dosari et al. (2009) "Nonviral Gene Delivery: Principle, Limitations, and Recent Progress" The AAPS Journal 2:4 671-681.

Angel et al. (2010) "Innate immune suppression enables frequent transfection with RNA encoding reprogramming proteins" PLoS One, 5:7 e11756.

Anguela et al. (2013) "Robust ZFN-mediated genome editing in adult hemophilic mice" Blood 122:19 3283-3287.

Anguela XM et al. (2013) "ZFN Mediated Targeting of Albumin "Safe Harbor" Results In Therapeutic Levels of Human Factor VIII in a Mouse Model of Hemophilia A." Blood 122:21 720-720.

Arnold et al. (1999) "Mutants of Tn3 resolvase which do not require accessory binding sites for recombination activity" EMBO Journal 18:1407-1414.

Arnold (1998) "When blind is better: protein design by evolution" Nature Biotechnology 16 617-618.

Arruda et al. (2017) "Novel approaches to hemophilia therapy: successes and challenges" Blood 2251-2256.

Banaszynski et al. (2006) "A rapid, reversible, and tunable method to regulate protein function in living cells using synthetic small molecules" Cell 126:5 995-1004.

Banko et al. "Chemical genetic screen for AMPKalpha2 substrates uncovers a network of proteins involved in mitosis" Molecular Cell 44:6 878-892.

Barzel et al. (2011) "Native homing endonucleases can target conserved genes in humans and in animal models" Nucleic Acids Research 39:15 6646-6659.

Barzel et al. (2015) "Promoterless gene targeting without nucleases ameliorates haemophilia B in mice" Nature 517 12.

Barzel et al. (2012) "Targeting 2A-Fusions to Endogenous Genes" Molecular Therapy 20:1 S234.

Benabdallah et al. (2010) "Targeted gene addition to human mesenchymal stromal cells as a cell-based plasma-soluble protein delivery platform" Cytotherapy 12:3 394-399.

Beumer et al. (2008) "Efficient gene targeting in Drosophila by direct embryo injection with zinc-finger nucleases" Proceedings of the National Academy of Sciences of the United States of America 105:50 19821-19826.

Blaese et al. (1995) "T lymphocyte-directed gene therapy for ADA-SCIO: initial trial results after 4 years" Science 270:5235 475-480.

Borel et al. (2017) "Survival Advantage of Both Human Hepatocyte Xenografts and Genome-Edited Hepatocytes for Treatment of ☐-1 Antitrypsin Deficiency" Molecular Therapy 25:11 1-13.

Boztug et al. (2010) "Stem-cell gene therapy for the Wiskott-Aldrich syndrome" The New England Journal of Medicine 363:20 1918-1927.

Breitbart et al. (2001) "Treatment of ischemic wounds using cultured dermal fibroblasts transduced retrovirally with PDGF-B and VEGF121 genes" Annals of Plastic Surgery 46:5 555-561.

Buchholz et al. (2001) "Alteration of Cre recombinase site specificity by substrate-linked protein evolution" Nat Biotechnology 19 1047-1052.

Capecchi (1980) "High efficiency transformation by direct microinjection of DNA into cultured mammalian cells" Cell 22 479-488.

Carter (1992) "Adeno-associated virus vectors" Current Opinion in Biotechnology 3 533-539 (1992).

Cavazzana-Calvo et al. (2000) "Gene therapy of human severe combined immunodeficiency (SCID)-X1 disease" Science 288:5466 669-672.

(56) References Cited

OTHER PUBLICATIONS

Cavazzana-Calvo et al (2010) "Transfusion independence and HMGA2 activation after gene therapy of human beta-thalassaemia" Nature 467:7313 318-322.
Chan et al. (2011) "Comparison of IRES and F2A-Based Locus-Specific Multicistronic Expression in Stable Mouse Lines" PLoS One 6(12): e28885, pp. 1-11.
Chandler et al. (2012) Pre-clinical efficacy and dosing of an AAV8 vector expressing human methylmalonyl-CoA mutase in a murine model of methylmalonic acidemia (MMA), Molecular Genetics and Metabolism 107:3 617-619.
Chandler et al. (2017) "Rescue of Mice with Methylmalonic Acidemia from Immediate Neonatal Lethality Using an Albumin Targeted, Promoterless Adeno-Associated Viral Integrating Vector" Molecular Therapy Abstract 26 25(5S1) 13.
Chang et al. (1987) "Modification of DNA ends can decrease end joining relative to homologous recombination in mammalian cells" Proceedings of the National Academy of Sciences of the United States of America 84 4959-4963.
Chen (2008) "Intron splicing-mediated expression of AAV Rep and Cap genes and production of AAV vectors in insect cells" Molecular Therapy 16:5 924-930.
Chen et al. (1996) "Production and Characterization of Human 293 Cell Lines Expressing the Site-Specific Recombinase Cre" Somatic Cell Molecular Genetics 22:6 477-88.
Christ et al. (1998) "Alterations in the Directionality of λ Site-specific Recombination Catalyzed by Mutant Integrases in Vivo" Journal Molecular Biology 288 825-836.
Christian et al. (2010) "Targeting DNA 25 Double-Strand Breaks with Tai Effector Nucleases, Genetics" 186:757-761.
Chu et al. (1981) "SV40 DNA transfection of cells in suspension: analysis of efficiency of transcription and translation of T-antigen" Gene 13:197.
Connelly et al. (2010) "Gene correction by homologous recombination with zinc finger nucleases in primary cells from a mouse model of a generic recessive genetic disease" Molecular Therapy 18:6 1103-1110.
Cox (1993) "The FLP protein of the yeast 2-microns plasmid: expression of a eukaryotic genetic recombination system in *Escherichia coli*" Proceedings of the National Academy of Sciences of the United States of America, 80 4223-4227.
Davidoff et al. (2016) "Genetic Targeting of the Albumin Locus to Treat Hemophilia" The New England Journal of Medicine 374 1288-1290.
Donsante et al. (2007) "AAV vector integration sites in mouse hepatocellular carcinoma" Science 317 477.
Dorgai et al. (1995) "Identifying Determinants of Recombination Specificity: Construction and Characterization of Mutant, Bacteriophage Integrases" Journal Molecular Biology 252 178-188.
Dorgai, L. et al. (1998) "Recognition of Core Binding Sites by Bacteriophage Integrases" Journal Molecular Biology 277: 1059-70 (1998).
Doyle et al. (2012) "The Construction of Transgenic and Gene Knockout/Knockin Mouse Models of Human Disease" Transgenic Res. 21(2): 327-349.
Eastman et al. (2002) "Development of Catheter-Based Procedures for Transducing the Isolated Rabbit Liver with Plasmid DNA" Human Gene Therapy 13:17 2065-2077.
Felgner et al. (1987) "Lipofection: A highly efficient, lipid-mediated DNA-transfection procedure" Proceedings of the National Academy of Sciences of the United States of America 84: 7413-7417.
Futerman et al. (2004) "The Cell Biology of Lysosomal Storage Disorders" Nature Reviews Molecular Cell Biology 5 554-565.
Galiano et al. (2004) "Quantitative and reproducible murine model of 10 excisional wound healing" Wound Repair and Regeneration 12:4:485-492.
Galetto et al. (2009) "Targeted approaches for gene therapy and the emergence of engineered meganucleases" Expert Opinion on Biological Therapy 9:10 1289-1303.

Gauglitz et al. (2011) "Combined gene and stem cell therapy for cutaneous wound healing" Molecular Pharmaceutics 8:5 1471-1479.
Graham et al. (1973) "A new technique for the assay of infectivity of human adenovirus 5 DNA" Virology 52 456-467.
Graham et al. (1977) "Characteristics of a Human Cell Line Transformed by DNA from Human Adenovirus Type 5" Journal of General Virology 36 59-72.
Grindley et al. (2006) "Mechanisms of Site-Specific Recombination" Annual Review of Biochemistry 75 567-605.
Guo et al. (1997) "Structure of Cre recombinase complexed with DNA in a site-specific recombination synapse" Nature 389 40-46.
Haceinbey-Abina et al. (2008) "Insertional oncogenesis in 4 patients after retrovirus-mediated gene therapy of SCID-X1" Journal of Clinical Investigation 118:9 3132-3142.
Händel et al. (2011) "Zinc-finger nuclease based genome surgery: it's all about specificity" Current Gene Therapy 11: : 28-37.
Hartley et al. (1980) "Nucleotide sequence of the yeast plasmid" Nature 286 860-864.
Hartung (1998) "Cre mutants with altered DNA binding properties" Journal of Biological Chemistry 273 22884-22891.
Henikoff (1998) "Conspiracy of silence among repeated transgenes" Bioessays, 20:7 532-535.
Hockemeyer et al. (2009) "Efficient targeting of expressed and silent genes in human ESCs and iPSCs using zinc-finger nucleases" Nature Biotechnology 27(9): 851-857.
Humbert et al. (2012) "Targeted Gene Therapies, Tools, Applications, Optimization" Critical Reviews in Biochemistry and Molecular Biology 47:3 264-281.
International Search Report for for PCT/US2013/032443, 5 pages (dated Nov. 12, 2013).
International Search Report for PCT/US2015/021501, 3 pages (dated Jul. 1, 2015).
Iwamoto et al. (2010) "A general chemical method to regulate protein stability in the mammalian central nervous system" Chemistry & Biology 17:9 981-988.
Kay et al. (2000) "Evidence for gene transfer and expression of factor IX in haemophilia B patients treated with an AAV vector" Nature Genetics 24:3: 257-261.
Keifer (2011) "Primer and Interviews: Advances in Targeted Gene Modification" 240 2688-2696.
Khan et al. (2011) "AAV-mediated gene targeting methods for human cells" Nature Protocols 6:4 482-501.
Khan et al. (2010) "Engineering of human pluripotent stem cells by AAV-mediated gene targeting" Molecular Therapy 18:6 1192-1199.
Kim et al. (2011) "High cleavage efficiency of a 2A peptide derived from porcine teschovirus-1 in human cell lines, zebrafish and mice" PLoS One 6 e18556.
Klein et al. (1987) "High-velocity microprojectiles for delivering nucleic acids into living cells" Nature 327 70-73.
Klippel et al. (1988) "Isolation and characterization of unusual gin mutants" EMBO Journal 7: 3983-3989.
Koerber et al. (2008) "DNA Shuffling of Adeno-associated Virus Yields Functionally Diverse Viral Progeny" Molecular Biology 16 1703-1709.
Koerber et al. (2009) "Molecular evolution of adeno-associated virus for enhanced glial gene delivery" Molecular Therapy 17 2088.
Kotin (1994) "Prospects for the use of adeno-associated virus as a vector for human gene therapy" Human Gene Therapy 5 793-801.
Lagos-Quintana et al. (2001) "Identification of novel genes coding for small expressed RNAs" Science 294 853-857.
Lagos-Quintana et al. (2002) "Identification of tissue-specific microRNAs from mouse" Current Biology 12 735-739.
Lagos-Quintana et al. (2003) "New microRNAs from mouse and human" RNA 9 175-179.
Lange-Gustafson et al. (1984) "Purification and properties of Int-h, a variant protein involved in site-specific recombination of bacteriophage lambda" The Journal of Biological Chemistry 259 12724-12732.
Langer (1990) "New Methods of Drug Delivery" Science 249 1527-1533.
Lau et al. (2001) "An abundant class of tiny RNAs with probable regulatory roles in Caenorhabditis elegans" Science 294 858-861.

(56) References Cited

OTHER PUBLICATIONS

Lebkowski et al. (1988) "Adeno-associated virus: a vector system for efficient introduction and integration of DNA into a variety of mammalian cell types" Molecular Cell Biology 8:3988-3996.
Lee et al. (2001) "An extensive class of small RNAs in Caenorhabditis elegans" Science 294 862.
Li et al. (2011) "In vivo genome editing restores haemostasis in a mouse model of haemophilia" Nature 475 217-221.
Li et al. (2010) "TAL nucleases (TALNs): hybrid proteins composed of TAL effectors and FokI DNA-cleavage domain" Nucleic Acids Research 39:1 359-372.
Lim et al. (2003) "Vertebrate microRNA genes" Science 299 1540.
Lim et al. (2003) "The microRNAs of Caenorhabditis elegans" Genes & Development 17 991-1008.
Lisowski et al. (2012) "Ribosomal DNA integrating rAAV-rDNA vectors allow for stable transgene expression" Molecular Therapy 20 1912-1923.
Liu (2000) "Protein Splicing Intein: Genetic Mobility, Origin, and Evolution, Annual Review of Genetics" 34 61-76.
Lombardo et al. (2007) "Gene editing in human stem cells using zinc finger nucleases and integrase-defective lentiviral vector delivery" Nature Biotechnology 25:11 1298-306.
Lorbach et al. (2000) "Site-specific Recombination in Human Cells Catalyzed by Phage 1 Integrase Mutants" J. Mol. Biol., 296: 1175-1181 (2000).
Madisen et al. (2010) "A robust and high-throughput Cre reporting and characterization system for the whole mouse brain" Nature Neuroscience 13(1): 133-142.
Maguire et al. (2008) "Safety and Efficacy of Gene Transfer for Leber's Congenital Amaurosis" The New England Journal of Medicine 358:21 2240-2248.
Mannino et al. (1988) "Liposome mediated gene transfer" Biotechniques 6 682-690.
Manno, et al. (2003) "AAV-mediated factor IX gene transfer to skeletal muscle in patients with severe hemophilia B" Blood 101:8 2963-2972.
Manno et al. (2006) "Successful transduction of liver in hemophilia by AAV-Factor IX and limitations imposed by the host immune response" Nature Medicine 12:3 342-347.
Mason et al. (2011) "Gene therapy for the peripheral nervous system: a strategy to repair the injured nerve?" Current Gene Therapy 11 75-89.
Martini et al. (2011) "Adeno-associated virus for cystic fibrosis gene therapy" Brazilian Journal of Medical and Biological Research 44 1097-1104.
Miller et al. (1980) "int-h: An int mutation of phage lambda that enhances site-specific recombination" Cell 20 721-729.
Miller et al. (2006) "Gene targeting in vivo by adeno-associated virus vectors" Nature Biotechnology 24:8 1022-1026.
Miller et al. (2003) "Human Gene Targeting by Adeno-Associated Virus Vectors is Enhanced by DNA Double-Strand Breaks" Molecular and Cellular Biology 23:10 3350-3357.
Minchiotti et al. (1989) "The Molecular Defect in a COOH-terminal-modified and Shortened Mutant of Human Srum Albumin" Journal of Biological Chemistry 264:6 3385-3389.
Minghetti et al. (1986) "Molecular Structure of the Human Albumin Gene is Revealed by Nucleotide Sequence within q11-22 of Chromosome 4" Journal of Biological Chemistry 261:15 6747-6757.
Mingozzi et al. (2011) "Therapeutic in vivo gene transfer for genetic disease using AAV: progress and challenges" Nature Reviews Genetics 12 341-356.
Mountford et al. (1994) "Dicistronic targeting constructs: Reporters and modifiers of mammalian gene expression" PNAS 91: 4303-4307.
Muskhelishvili et al. (1993) "SSV1-encoded site-specific recombination system in Sulfolobus shibatae" Molecular Genetics and Genomics 237 334-342.
Mussolino (2012) "TALE nucleases: tailored genome engineering made easy" Current Opinion in Biotechnology 23:5 644-50.
Mutskov et al. (2004) "Silencing of transgene transcription precedes methylation of promoter DNA and histone H3 lysine 9" EMBO Journal 23:1 138-149.
Muzyczka (1992) "Use of adeno-associated virus as a general transduction vector for mammalian cells" Current Opinion in Biotechnology 158 97-129.
Nakai et al. (2005) "Unrestricted hepatocyte transduction with adeno-associated virus serotype 8 vectors in mice" Journal Virology 79 214-224.
Nathwani et al. (2011) "Adenovirus-associated virus vector-mediated gene transfer in hemophilia B" The New England Journal of Medicine 365:25 2357-2365.
Nehls et al. (1996) "Two Genetically Separable Steps in the Differentiation of Thymic Epithelium" Science 272 886-889.
Nygaard et al. (2016) "A universal system to select gene-modified hepatocytes in vivo" Science Translational Medicine 8:342 342ra79.
Palmer et al. (1989) "Production of human factor IX in animals by genetically modified skin fibroblasts: potential therapy for hemophilia B" Blood 73:2 438-45.
Paulk et al. (2012) "AAV-mediated gene targeting is significantly enhanced by transient inhibition of nonhomologous end joining or the proteasome in vivo" Human gene therapy 23 658-665.
Perez-Pinera et al. (2012) "Advances in targeted genome editing" Current Opinion in Biotechnology 16:3-4 268-277.
Porro et al. (2017) "Promoterless gene targeting without nucleases rescues lethality of a Crigler-Najjar syndrome mouse model" EMBO Molecular Medicine 1-10.
Porter et al. (2011) "Chimeric antigen receptor-modified T cells in chronic lymphoid leukemia" The New England Journal of Medicine 365:8 725-733.
Pruett-Miller et al. (2009) "Attenuation of zinc finger nuclease toxicity 30 by small-molecule regulation of protein levels" PLOS Genetics 5:2 e1000376.
Pruett-Miller et al. (2008) "Comparison of zinc finger nucleases for use in gene targeting in mammalian cells" Molecular Cellular 16:4 707-717.
Racaniello (2013) "How many viruses on Earth" Virology 3 pages. URL: http://www.virology.ws/2013/09/06/how-many-viruses-on-earth.
Rosser et al. (2010) "Repeat-induced gene silencing of L 1 transgenes is correlated with differential promoter methylation" Gene 456:1-2 15-23.
Roth et al. (2001) "Nonviral transfer of the gene encoding coagulation factor VIII in patients with severe hemophilia A" The New England Journal of Medicine 344:23 1735-1742.
Sadowski (1993) "Site-specific genetic recombination: hops, flips and flops" Federation of American Societies for Experimental Biology 7:760-767.
Santoro et al. (2002) "Directed evolution of the site specificity of Cre recombinase" Proceedings of the National Academy of Sciences of the United States of America 99 4185-4190.
Sauer (1994) "Site-specific recombination: developments and applications" Current Opinion in Biotechnology 5: 521-527.
Saxena et al. (1997) "Probing Flp: a new approach to analyze the structure of a DNA recognizing protein by combining the genetic algorithm, mutagenesis and non-canonical DNA target sites" Biochimica et Biophysica Acta 1340 187-204.
Sclimenti et al. (2001) "Directed evolution of a recombinase for improved genomic integration at a native human sequence" Nucleic Acids Research 29 5044-51.
Semple et al. (2010) "Rational design of cationic lipids for siRNA delivery" Nature Biotechnology 28:2 172-178.
Shaikh et al. (1977) "The Cre recombinase cleaves the lox site in trans" Journal of Biological Chemistry 272 5695-5702.
Shalaby et al. (1990) "Exon skipping during splicing of albumin mRNA precursors in Nagase analbuminemic rats" Proceedings of the National Academy of Sciences of the United States of America 87 2652-2656.
Shanks et al. (2009) "Are animal models predictive for humans?" Philosophy, Ethics, and Humanities in Medicine 1-20.

(56) References Cited

OTHER PUBLICATIONS

Sharma et al. (2013) "Abstract #488: In Vivo ZFN Mediated Targeting of Albumin as a Platform for Expression of Multiple Therapeutic Genes" Molecular Therapy 21(Supplement 1) S188-S189.
Sharma et al. (2012) "2A peptides provide distinct solutions to driving stop-carry on translational recoding" Nucleic Acid Research 40(7): 3143-3151.
Shelling et al. (1994) "Targeted integration of transfected and infected adeno-associated virus vectors containing the neomycin resistance gene" Gene Therapy 1165-1169.
Shi et al. (2013) "Role of antigen-specific regulatory CD4+CD25+ T cells in tolerance induction after neonatal IP administration of AAV-hF.IX" Gene therapy 20 987-996.
Shigekawa et al. (1988) "Electroporation of eukaryotes and prokaryotes: a general approach to the introduction of macromolecules into cells" Biotechniques 6 742-751.
Silva et al. (2011) "Meganucleases and Other Tools for Targeted Genome Engineering: Perspective and Challenges for Gene Therapy, Current Gene Therapy" 11-27.
Stankunas et al. (2003) "Conditional protein alleles using knockin mice and a chemical inducer of dimerization" Molecular Cellular 12:6 1615-1624.
Stein et al. (2010) "Genomic instability and myelodysplasia with monosomy 7 consequent to EV11 activation after gene therapy for chronic granulomatous disease" Nature Medicine 16:2 198-204.
Szymczak et al. (2004) "Correction of multi-gene deficiency in vivo using a single 'self-cleaving' 2A peptide-based retroviral vector" Nature Biotechnology 22:5 589-594.
Takeuchi et al. (2011) "Tapping natural reservoirs of homing endonucleases for targeted gene modification" Proceedings of the National Academy of Sciences 13077-13082, Proceedings of the National Academy of Sciences of the United States of America.
Tanaka et al. (1998) "A highly efficient method for the site-specific integration of transfected plasmids into the genome of mammalian cells using purified retroviral integrase" Gene 17 67-76.
Titeux et al. (2010) "SIN retroviral vectors expressing COL7A1 under human promoters for ex vivo gene therapy of recessive dystrophic epidermolysis bullosa" Molecular Therapy 18:8 1509-1518.
Urnov et al. (2005) "Highly efficient endogenous human gene correction using designed zinc-finger nucleases" Nature 435:7042 646-651.
Van Rensburg et al. (2013) "Chromatin structure of two genomic sites for targeted transgene integration in induced pluripotent stem cells and hematopoietic stem cells" Gene therapy 20:2 201-214.
Vergunst et al. (2000) "VirB/D4-Dependent Protein Translocation from Agrobacterium into Plant Cells" Science 290 979-982.
Voziyanov et al. (2002) "A dual reporter screening system identifies the amino acid at position 82 in Flp site-specific recombinase as a determinant for target specificity" Nucleic Acids Research 30 1656-1663.
Voziyanov et al. (2003) "Stepwise Manipulation of DNA Specificity in Flp Recombinase: Progressively Adapting Flp to Individual and Combinatorial Mutations in its Target Site" Journal of Molecular Biology 326 65-76.
Wang et al. (2000) "Sustained Expression of Therapeutic Level of Factor IX in Hemophilia B Dogs by AAV-Mediated Gene Therapy in Liver" Molecular Therapy 1:2 154-158.
Wang (2012) "Targeted gene addition to a predetermined site in the human genome using a ZFN-based nicking enzyme" Genome Research 22:7 1316-1326.
Wei et al. (2011) "Rapid derivation of genetically related mutants from embryonic cells harboring a recombinase specific Trp53 platform" Cell Cycle 10(8): 1261-1270.
Written Opinion for PCT/US2013/032443, 8 pages (dated Nov. 12, 2013).
Written Opinion for PCT/US2015/021501, 7 pages (dated Jul. 1, 2015).
Xinfang et al. (1996) "Implantation of autologous skin fibroblast genetically modified to secrete clotting factor IX partially corrects the hemorrhagic tendencies in two hemophilia B patients" Chinese Medical Journal (Engl) 109:11 832-839.
Yagil et al. (1995) "Identifying Determinants of Recombination Specificity: Construction and Characterization of Chimeric Bacteriophage Integrases" Journal of Molecular Biology 252 163-177.
Yew et al. (2013) "Gene therapy for lysosomal storage disorders" Pediatric endocrinology reviews: PER 11 Suppl 1 99-109.
Zhang et al. (2011) "Enhanced collateral growth by double transplantation of gene-nucleofected fibroblasts in ischemic hindlimb of rats" PLoS One 6:4 e19192.
Zhang et al. (1997) "Expression of Naked Plasmid DNA Injected into the Afferent and Efferent Vessels of Rodent and Dog Livers" Human Gene Therapy 8 1763-1772.
Zhou et al. (1994) "Adeno-associated virus 2-mediated high efficiency gene transfer into immature and mature subsets of hematopoietic progenitor cells in human umbilical cord blood" Journal of Experimental Medicine 179 1867-1875.
Ziello et al. (2010) "Cellular Endocytosis and Gene Delivery" Molecular Medicine 16:5-6 222-229.
Zou et al. (2011) "Oxidase-deficient neutrophils from X-linked chronic granulomatous disease iPS cells: functional correction by zinc finger nuclease-mediated safe harbor targeting" Blood 117:21 5561-5572.
Kattenhorn et al. (2016), "Adeno-Associated Virus Gene Therapy for Liver Disease", Human Gene Therapy, vol. 27. No. 12: 947-961.
Karnan et al., (2016), "Improved methods of AAV-mediated gene targeting for human cell lines using ribosome-skipping 2A peptide", Nucleic Acids Research, vol. 44, No. 6, e54, 1-14.
Chandler et al., "Treatment of Methylmalonic Acidemia by Promoterless Gene-Targeting Using Adeno-Associated Viral (AAV) Medicated Homologous Recombination", Molecular Therapy, vol. 24, May 2016, pp. S21-S22.
Chandler et al., "Targeted integration of MUT into the Albumin Locus Using a Promoterless AAV Vector (Generide TM) Confers a Hepatocellular Growth Advantage in Mice with Methylmalonic Acidemia", ASGCT, 2018, pp. 1-1.

FIGURE 6
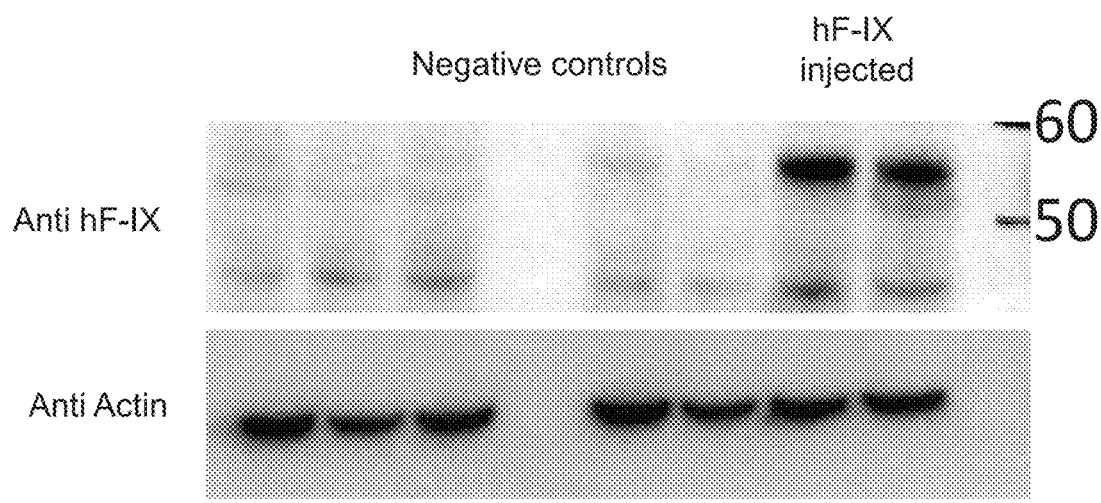
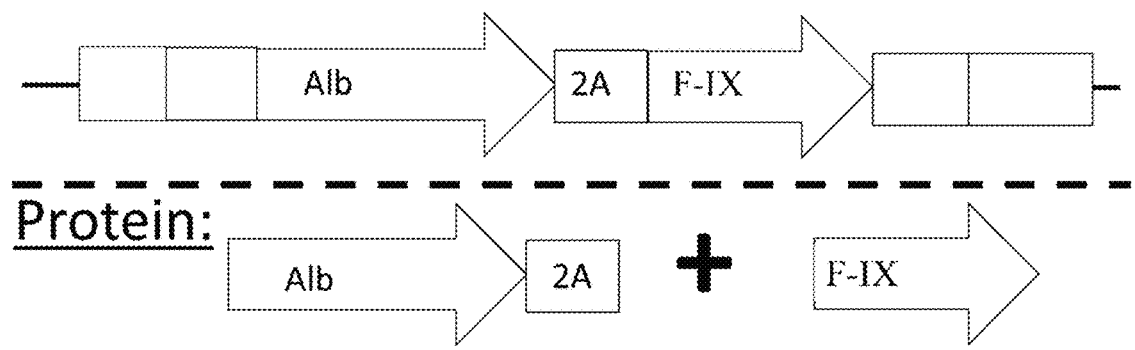

FIGURE 8
A
DNA:
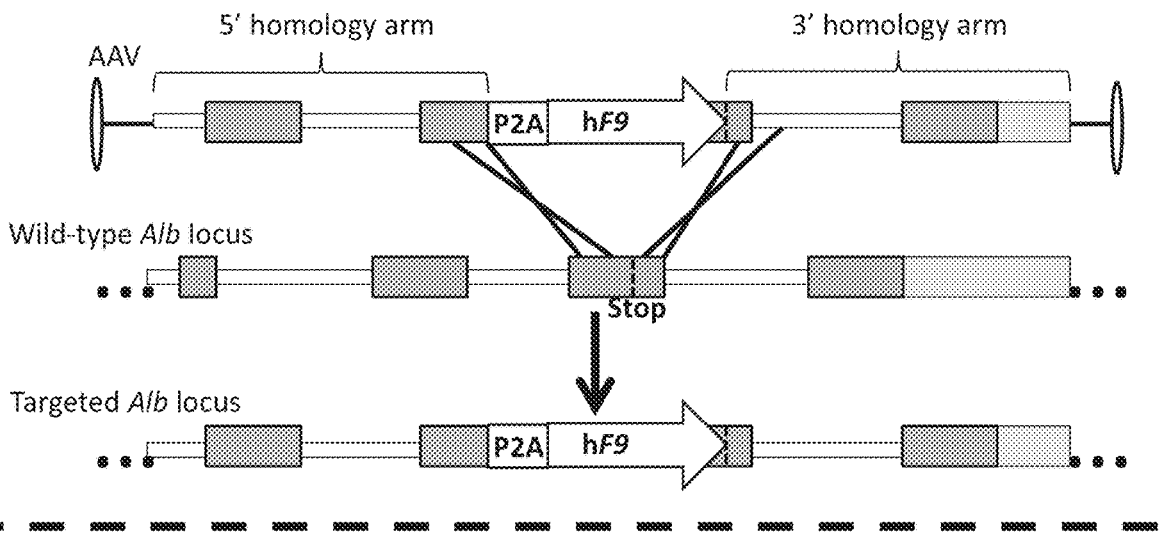
RNA: Fused mRNA
Protein:
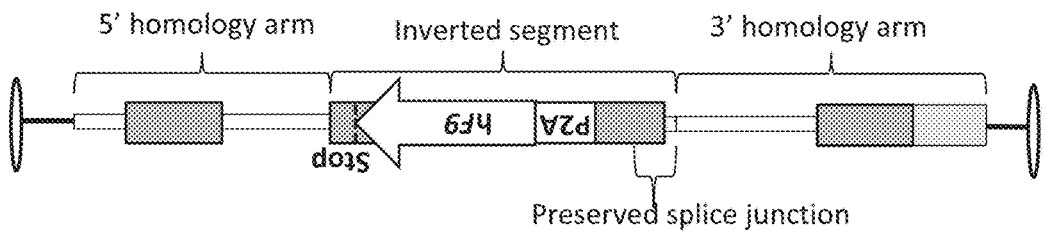
B

FIGURE 9
A
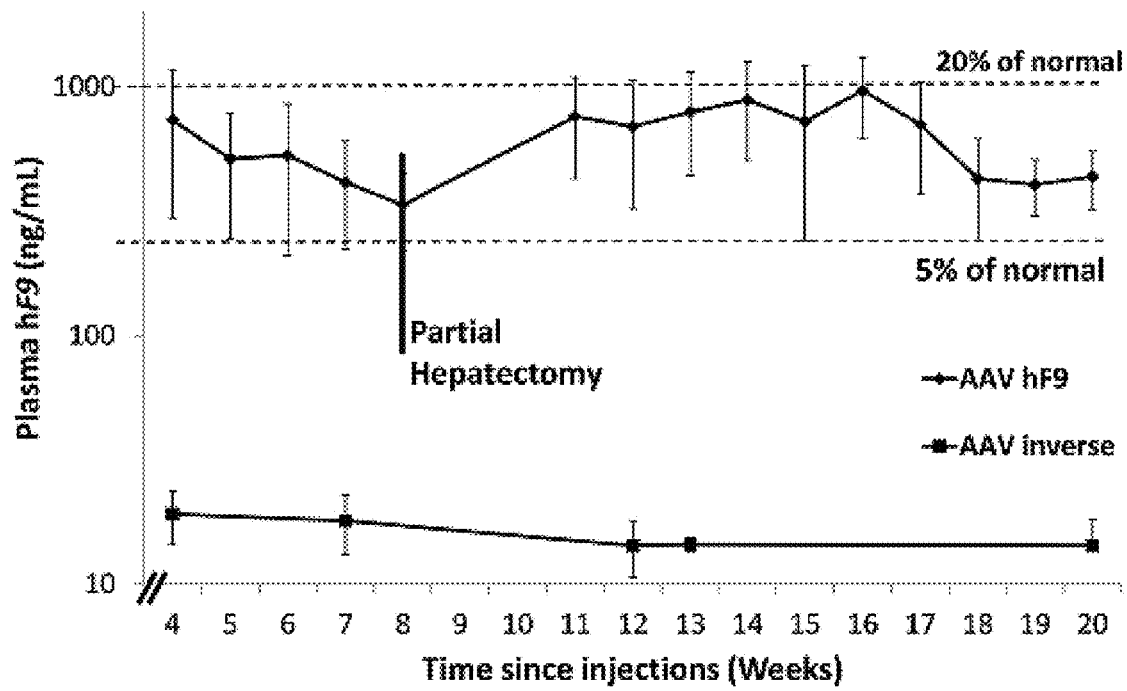
B
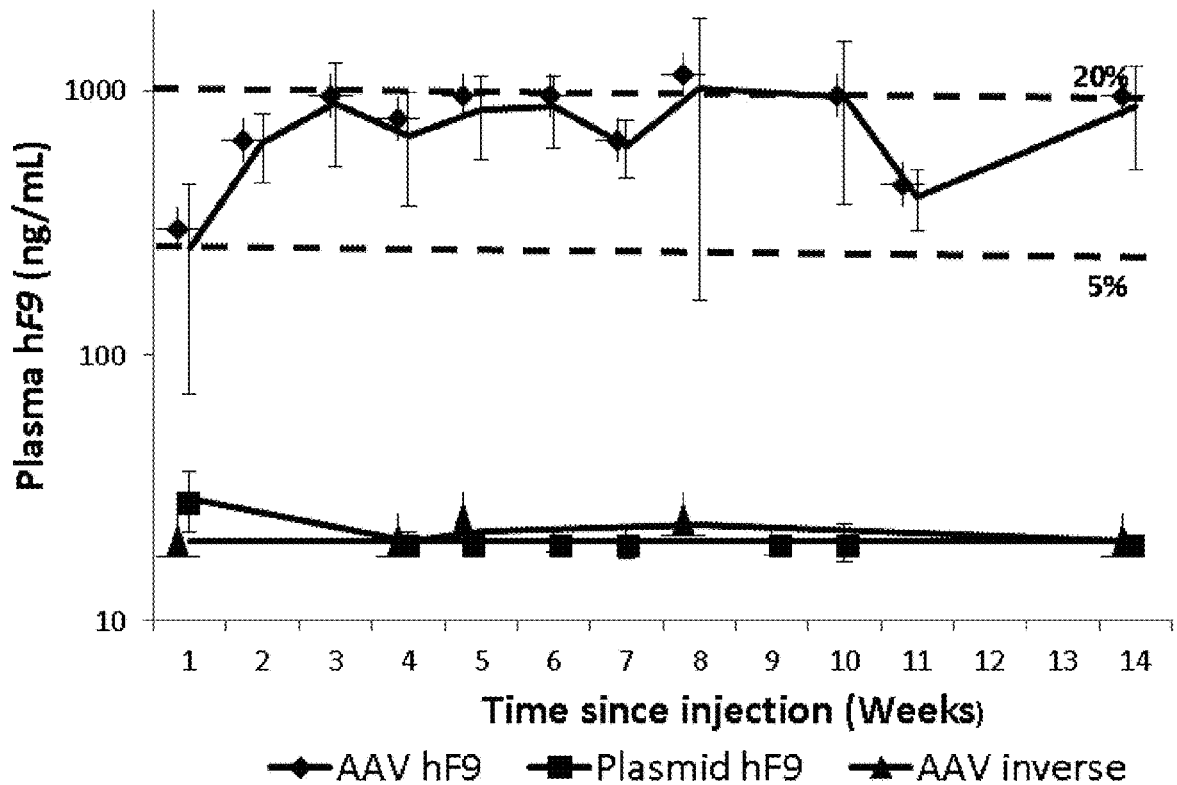

FIGURE 9 (Cont. 1)
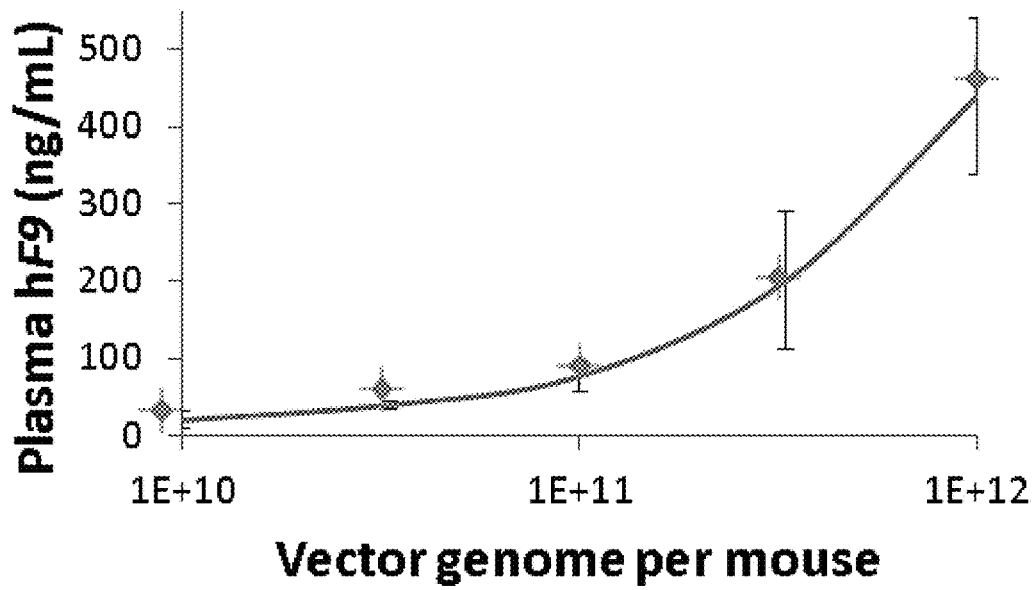
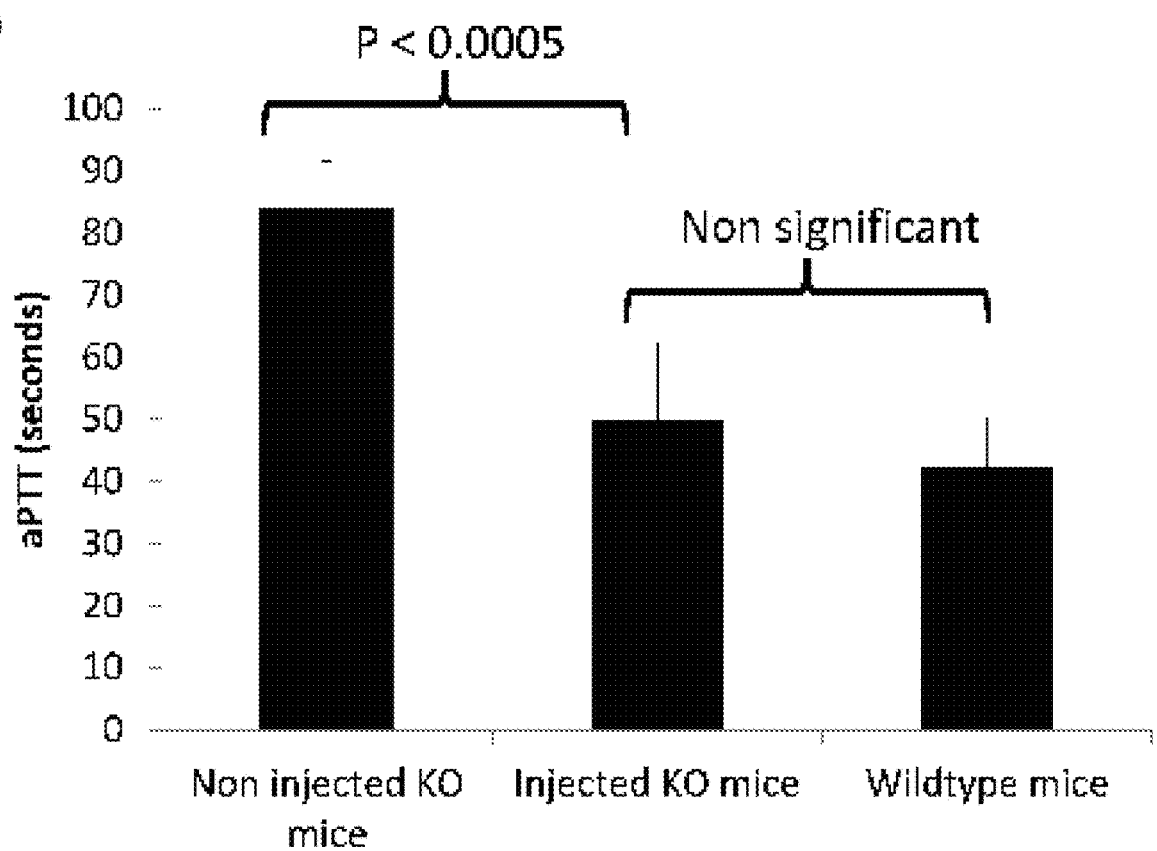

FIGURE 9 (Cont. 2)
E
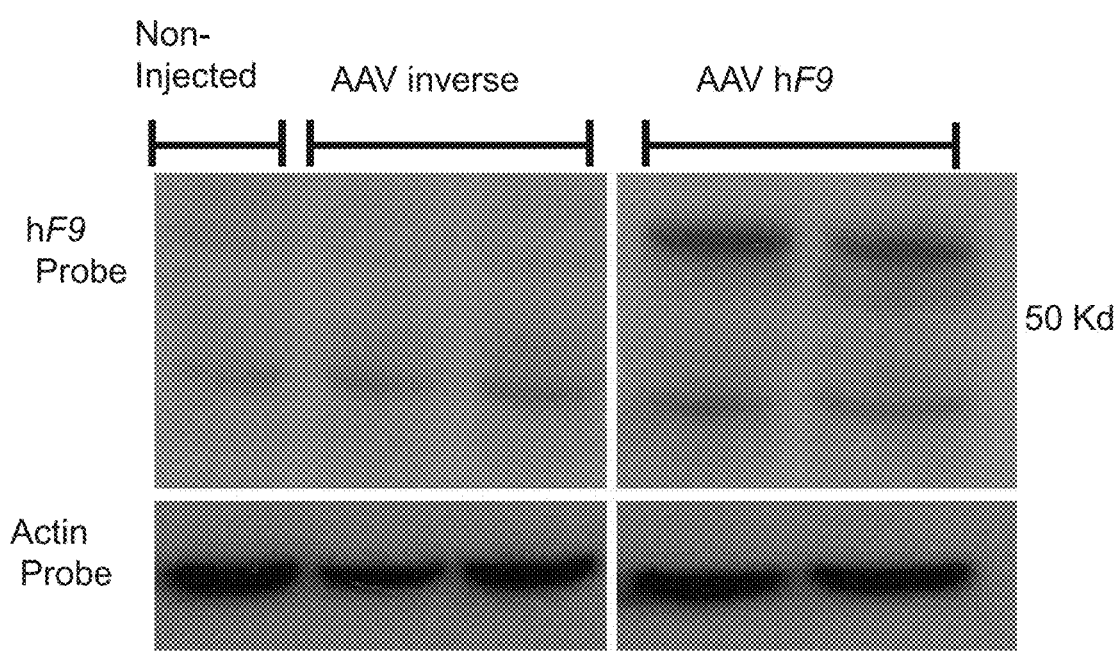

FIGURE 10
A
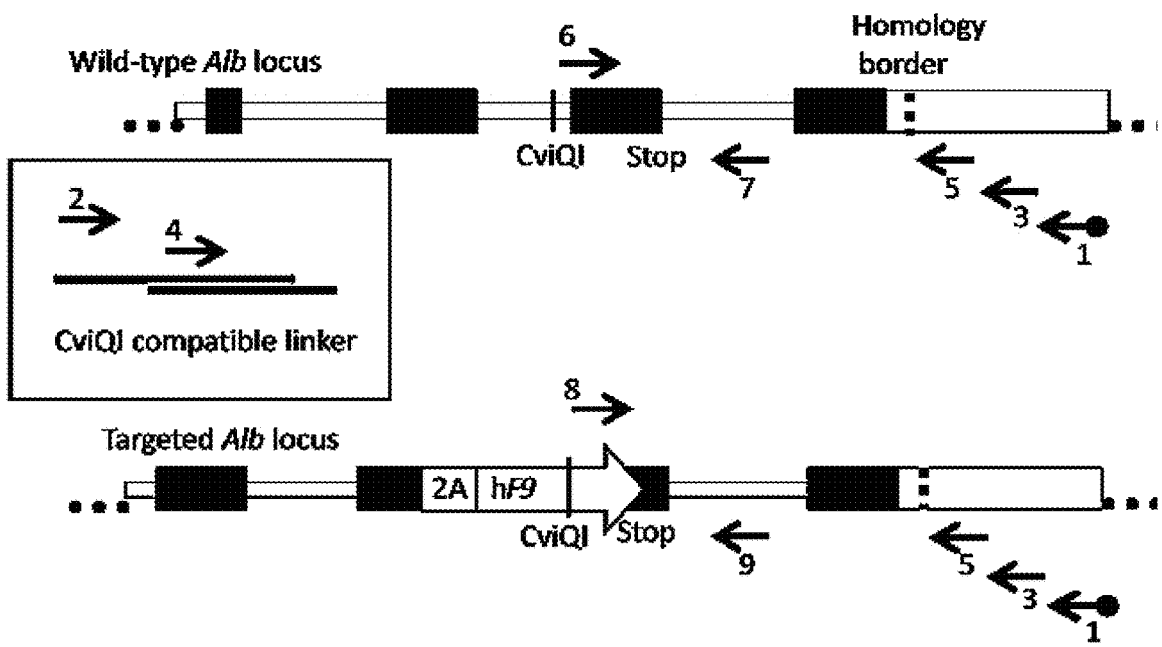
B
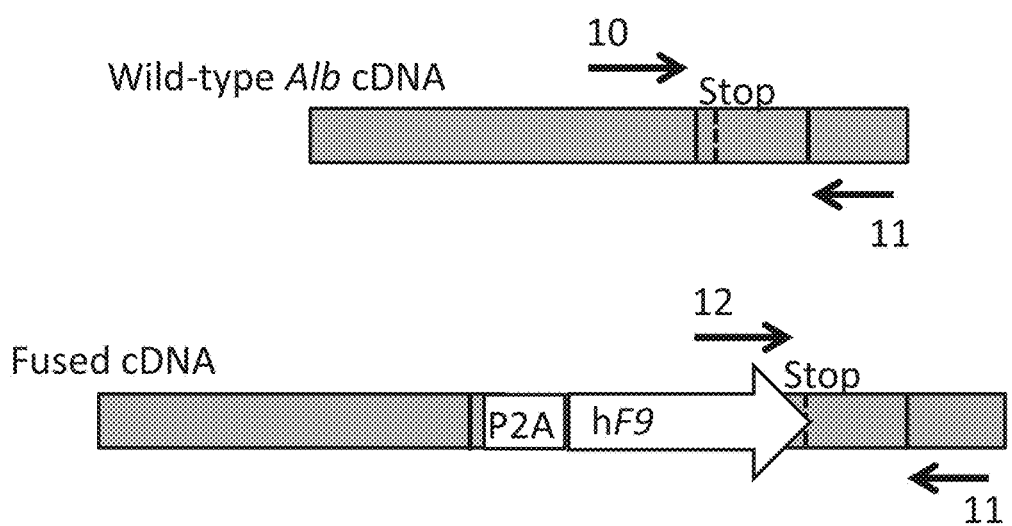

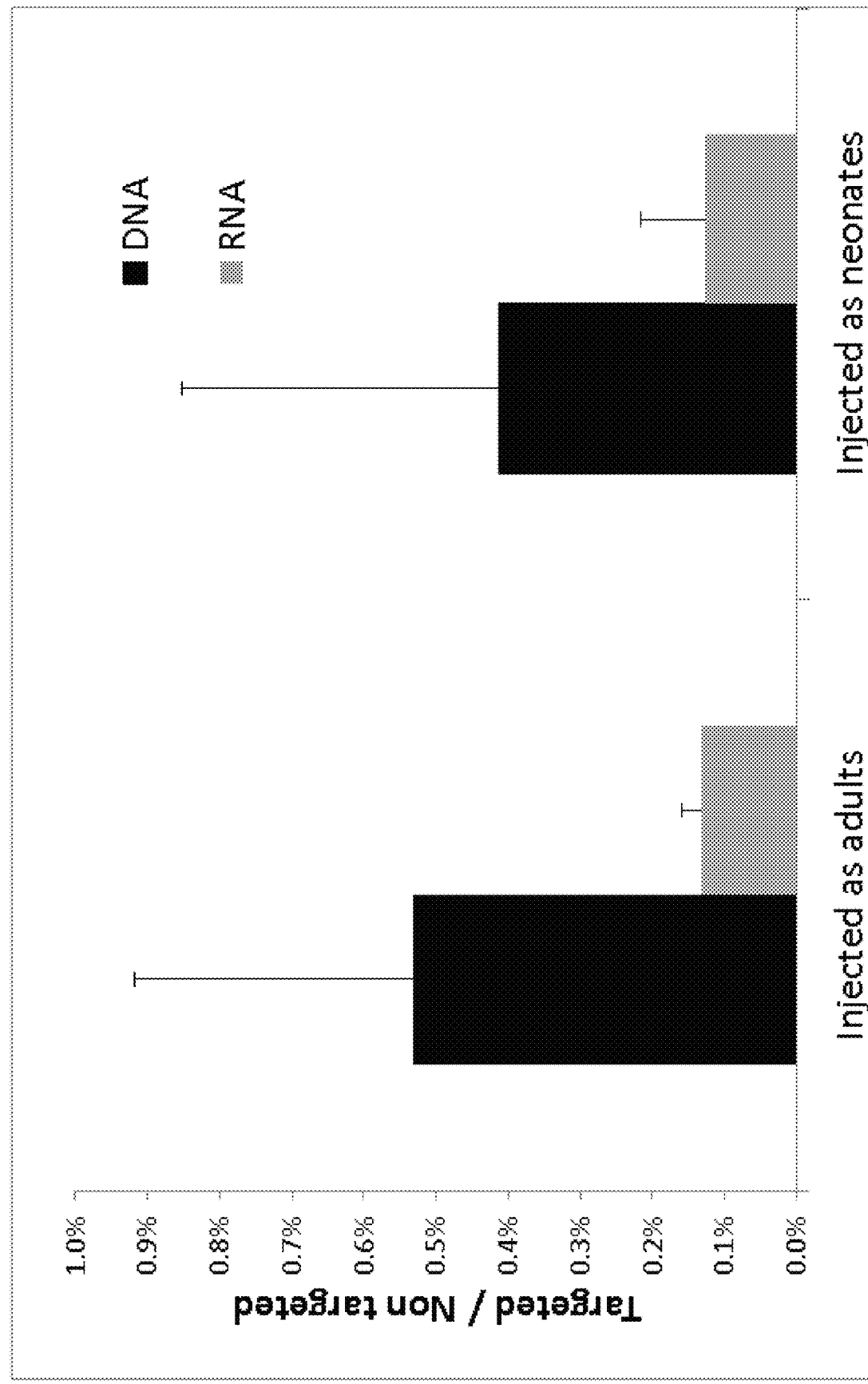
FIGURE 10 (Cont. 1)
C

FIGURE 11
A
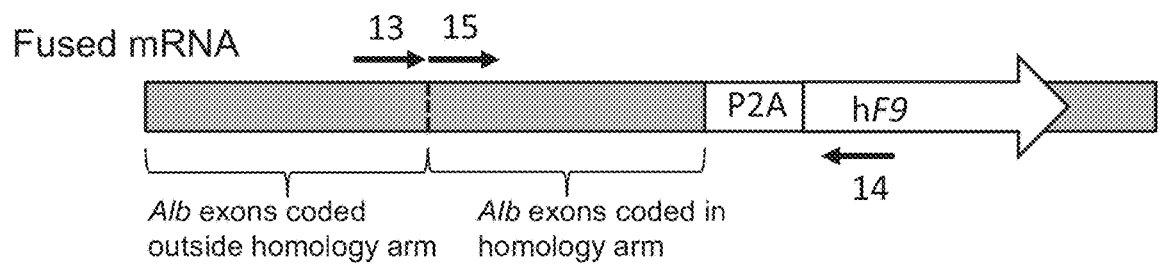
B
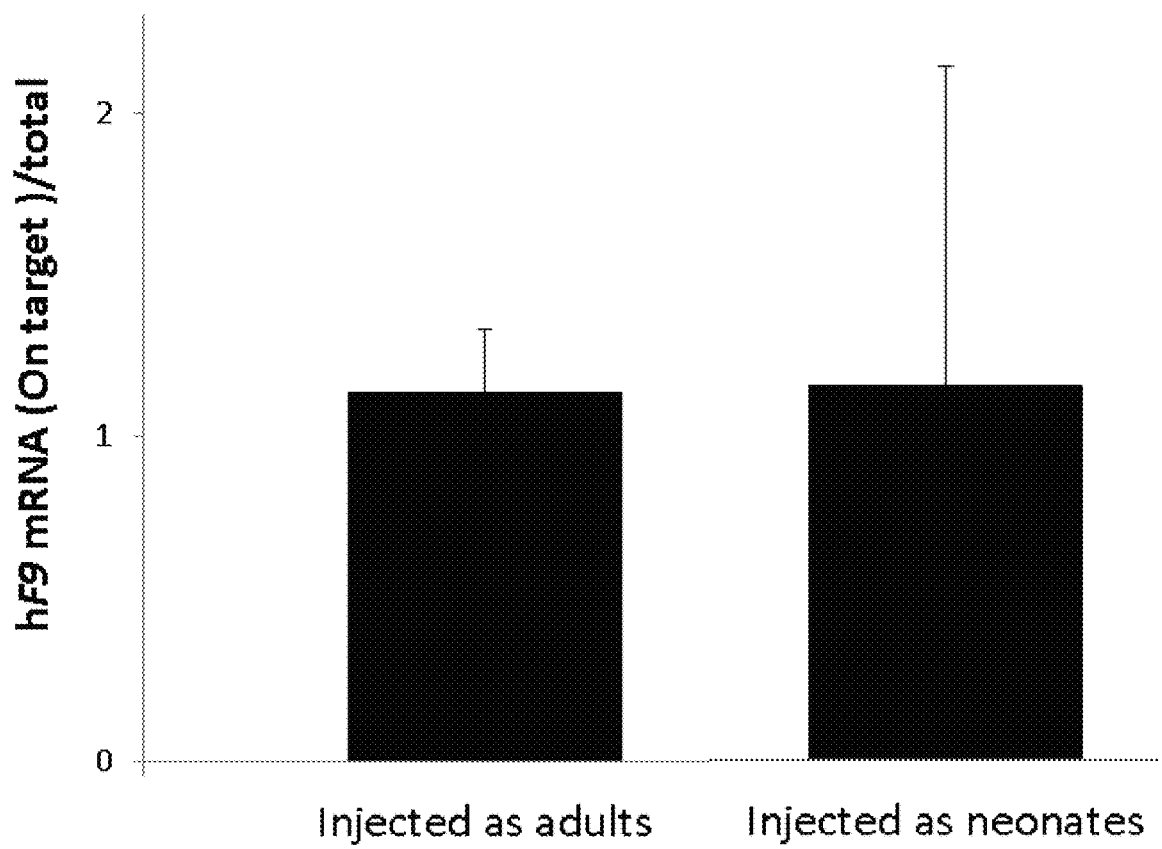

FIGURE 11 (Cont. 1)
C
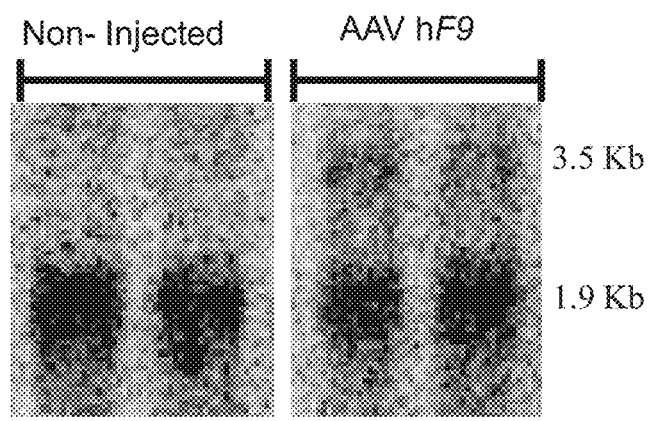
D
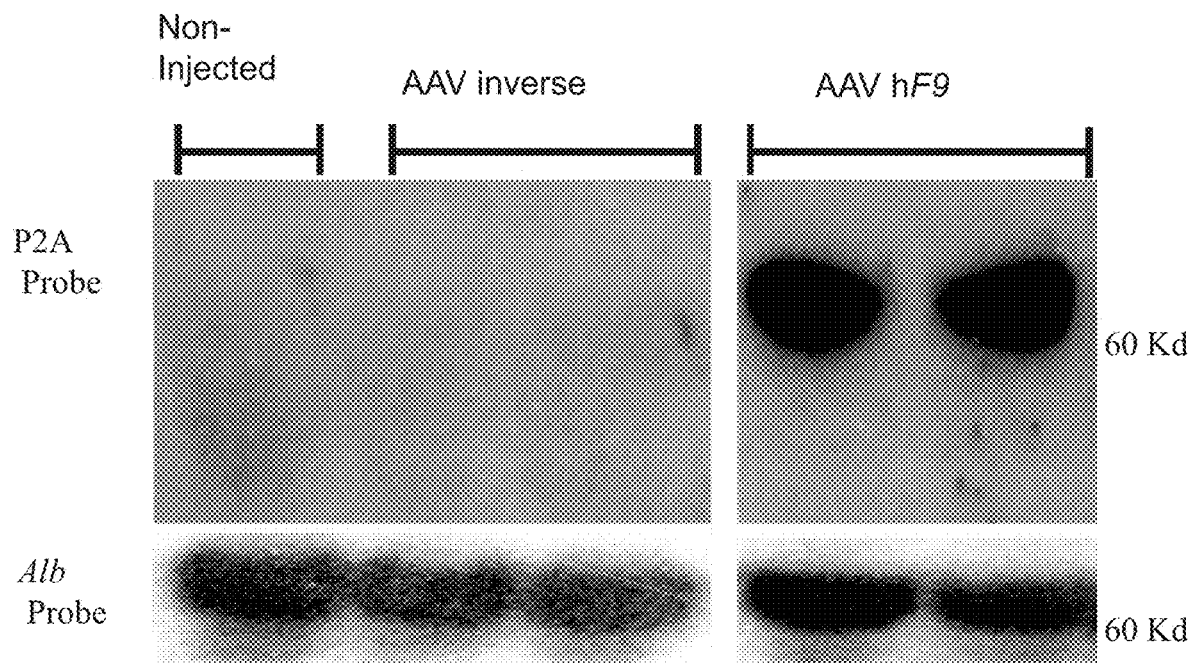

FIGURE 13
Step 1: Linear amplification (LAM)
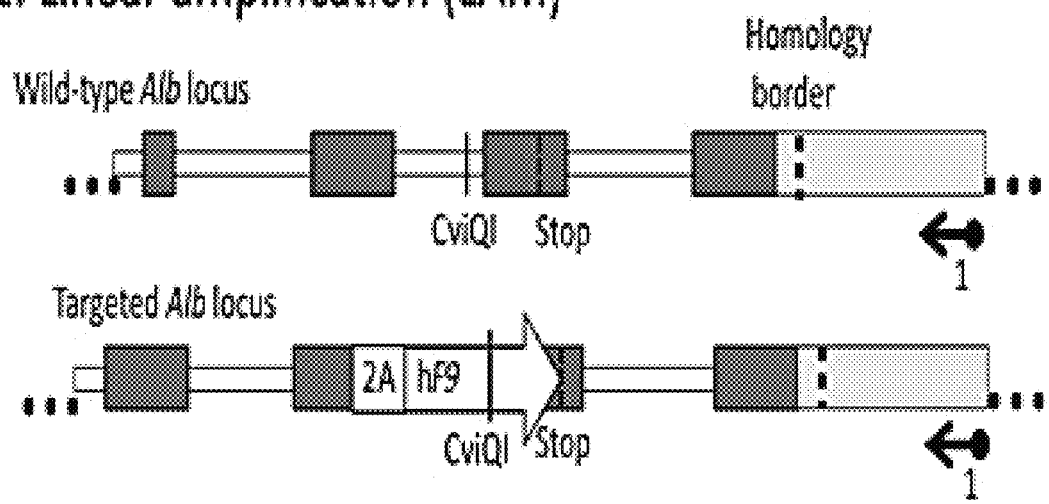
Step 2: Binding to beads and wash
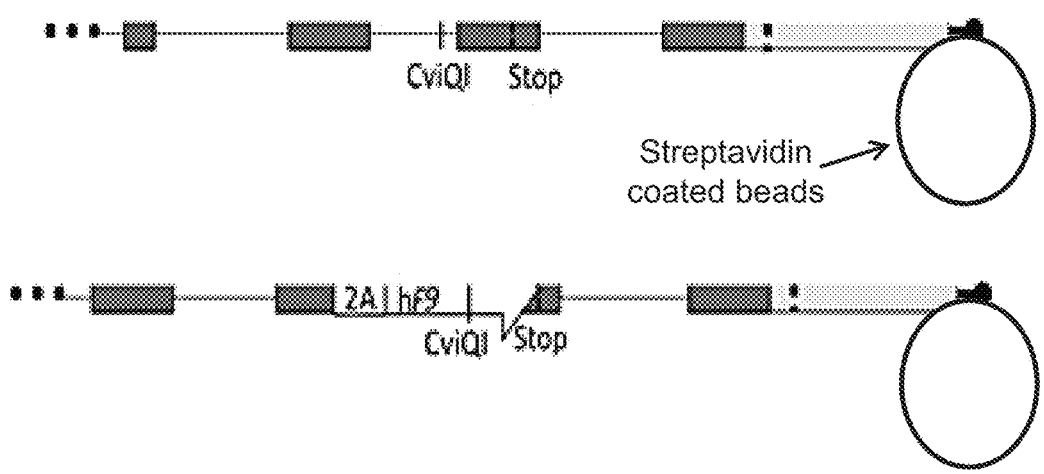

FIGURE 13 (Cont. 1)
Step 3: Second strand DNA synthesis with random primers
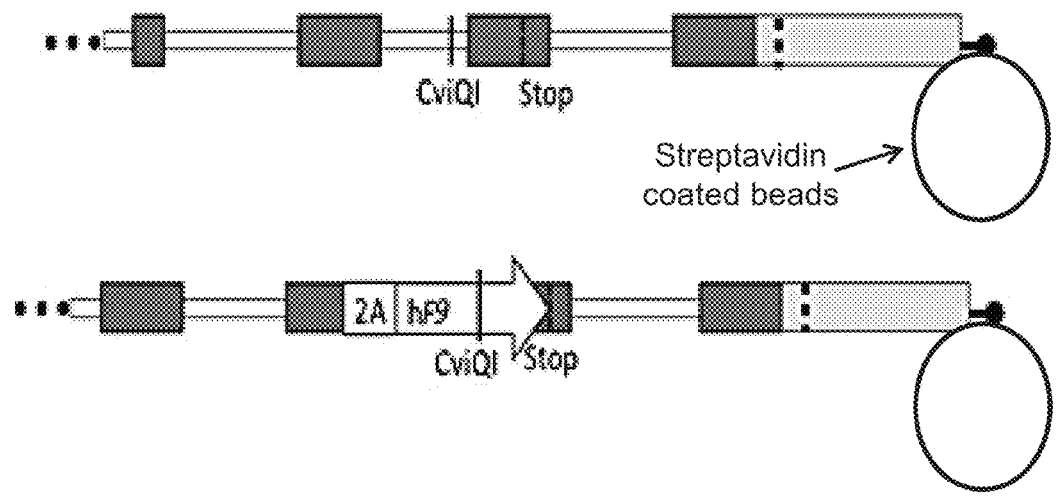
Step 4: CviQI cleavage
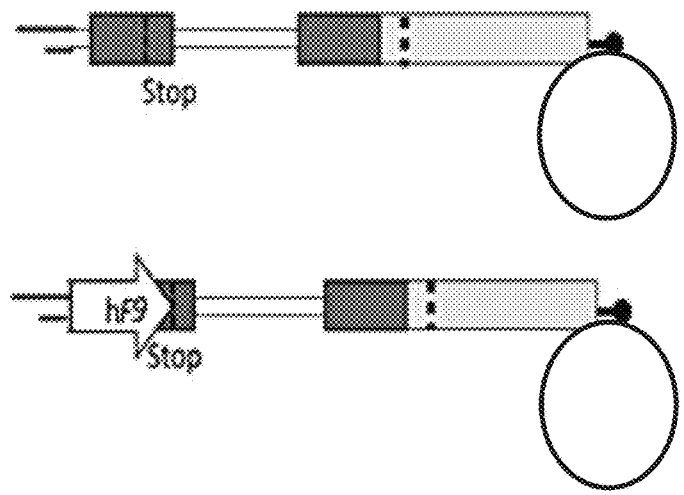

FIGURE 13 (Cont. 2)
Step 5: Linker ligation
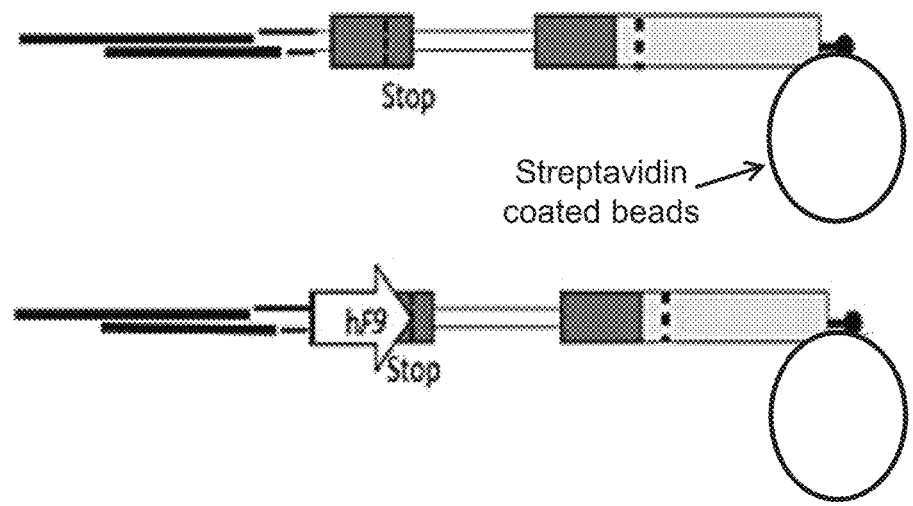
Step 6: 1ˢᵗ nested PCR
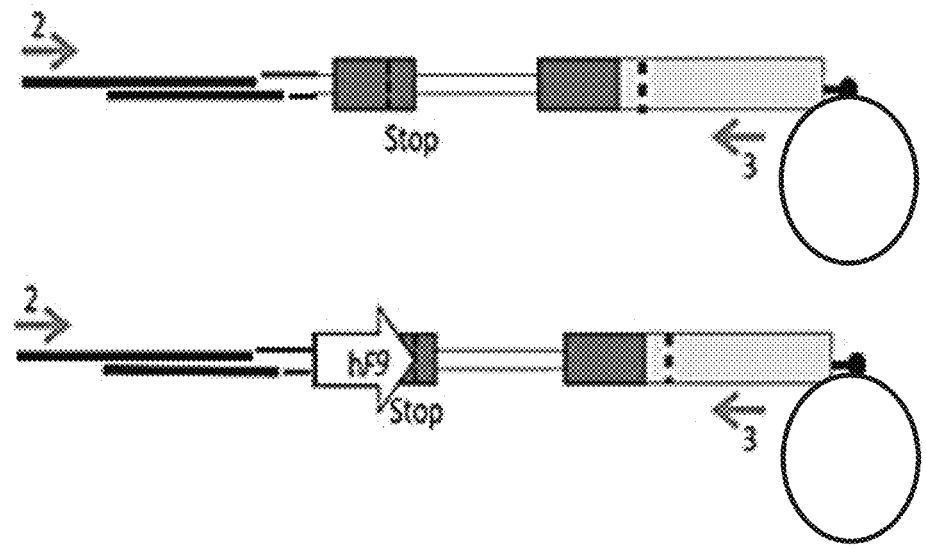

FIGURE 13 (Cont. 3)
Step 7: 2nd nested PCR
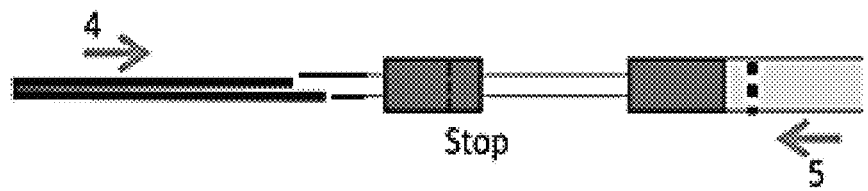
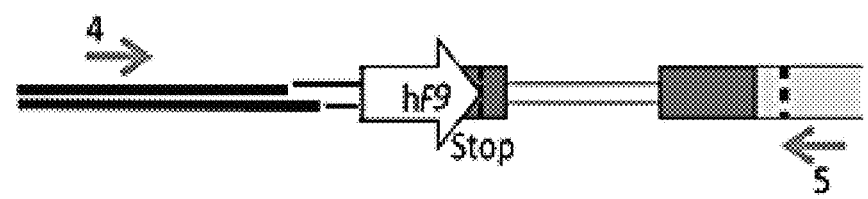
Step 8: qPCR (different primer pairs in different wells)
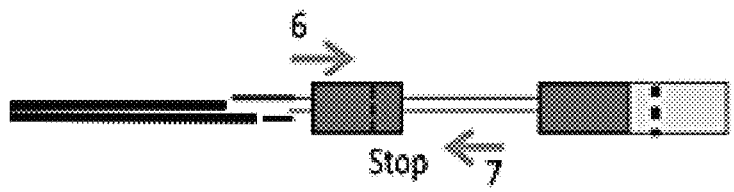
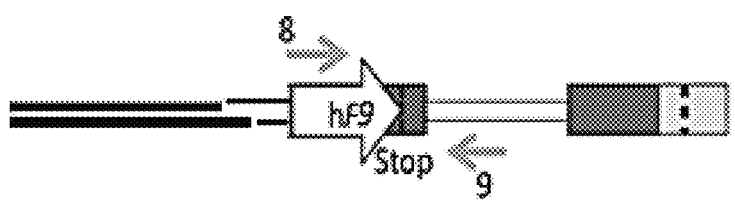

FIGURE 14
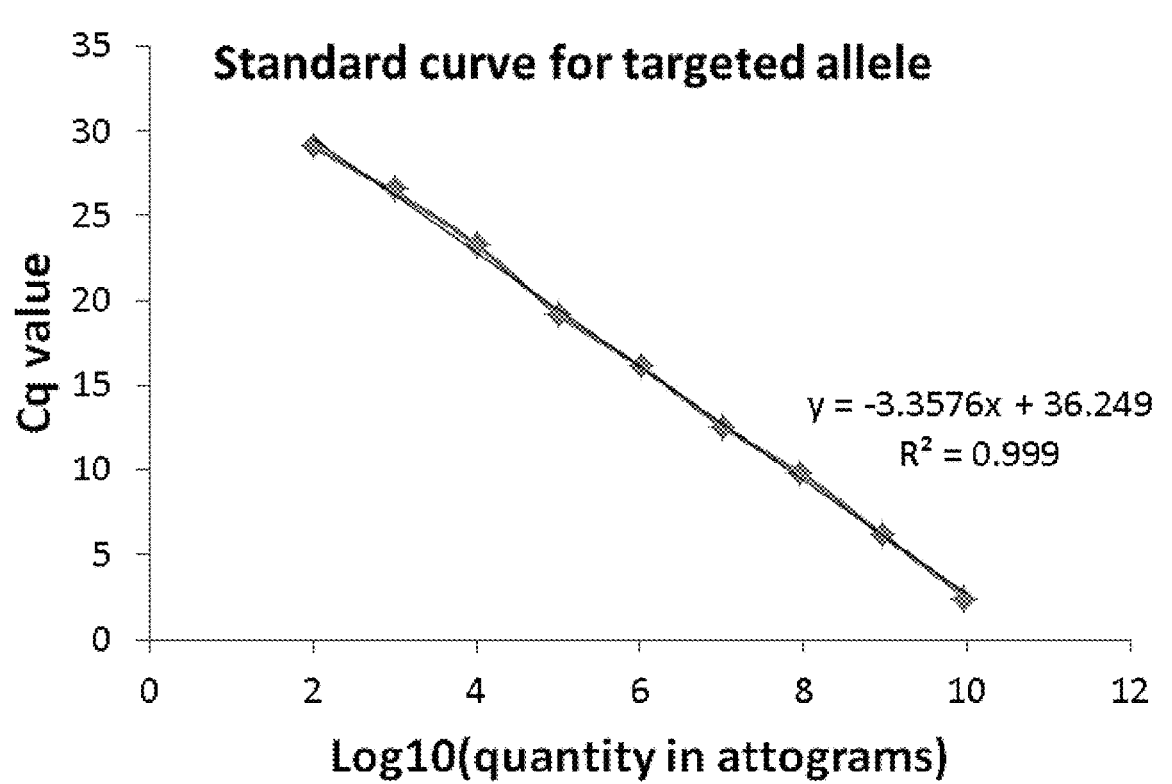
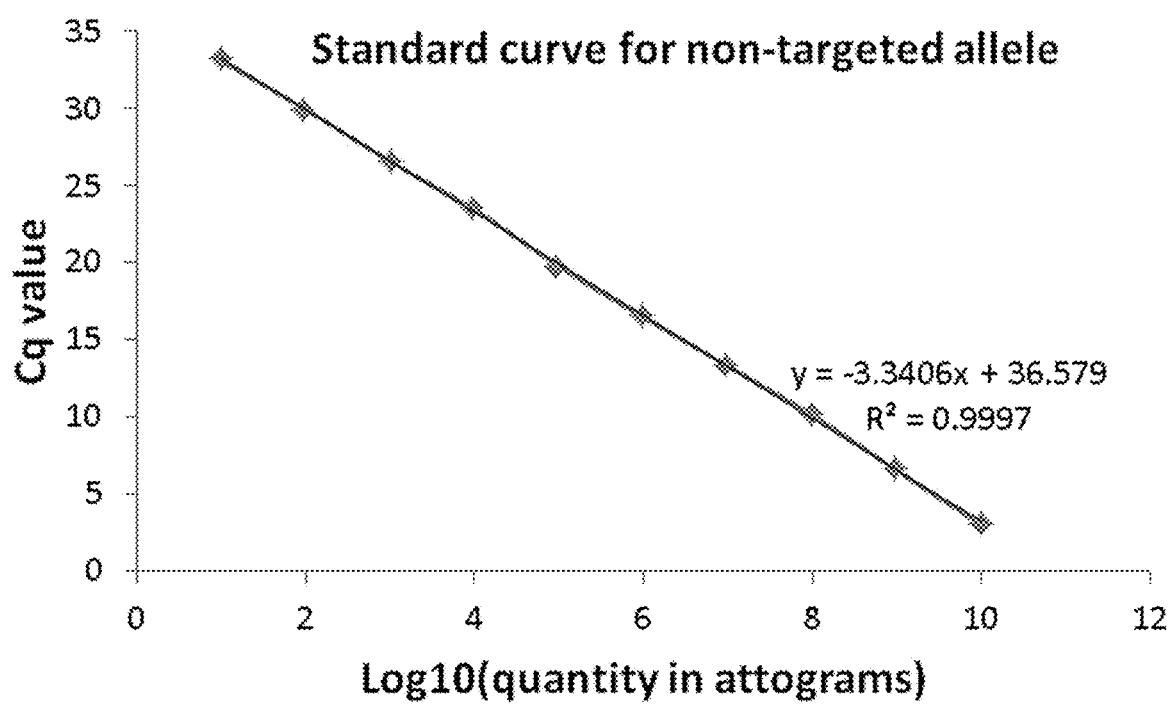

FIGURE 17

| Position | ID | REF | ALT | HAP1 | HAP2 | HAP3 | HAP4 | HAP5 | HAP6 | HAP7 |
|---|---|---|---|---|---|---|---|---|---|---|
| 74285239 | rs962304 | C | T | T | C | C | C | C | T | C |
| 74285552 | rs4076 | A | G | A | G | A | A | A | G | G |
| 74285567 | rs962005 | C | A | C | A | C | C | C | A | A |
| 74285758 | rs2236766 | G | T | G | T | T | G | G | T | T |
| 74285823 | rs2236767 | G | A | G | A | G | G | G | A | A |
| 74286013 | STOP | | | | | | | | | |
| 74287403 | rs429703 | T | C | C | T | T | C | T | T | C |
| Frequency | | | | 50.14% | 44.69% | 2.15% | 1.51% | 1.37% | 0.09% | 0.05% |

FIGURE 19
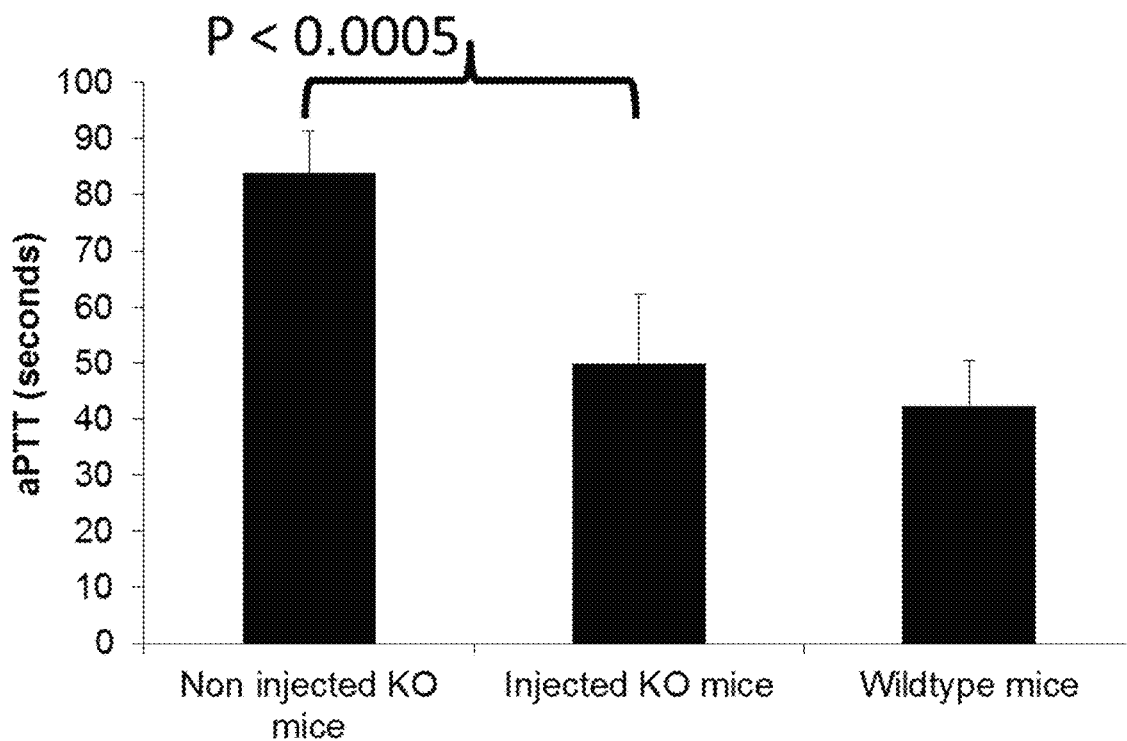
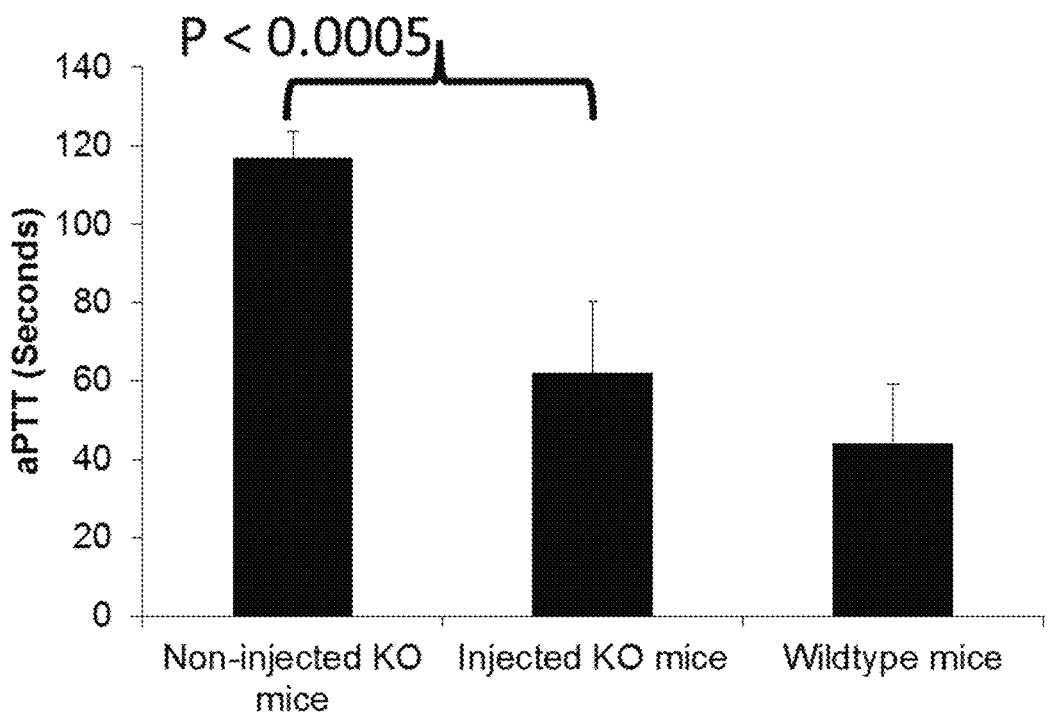

GENOME EDITING WITHOUT NUCLEASES

CROSS-REFERENCE

This application is a continuation of U.S. patent application Ser. No. 17/067,236 filed Oct. 9, 2020, which is a continuation of U.S. patent application Ser. No. 16/801,531 filed Feb. 26, 2020, which is a continuation of U.S. patent application Ser. No. 15/126,860 filed Sep. 16, 2016, now U.S. Pat. No. 10,612,041 issued on Apr. 7, 2020, which is a national stage filing of International Patent Application No. PCT/US2015/021501 filed Mar. 19, 2015, which claims the benefit of U.S. Provisional Patent Application Nos. 62/045,451 filed Sep. 3, 2014, 62/044,145 filed Aug. 29, 2014, 61/969,709 filed Mar. 24, 2014, and 61/969,013 filed Mar. 21, 2014, each of which applications is incorporated herein by reference in its entirety.

GOVERNMENT RIGHTS

This invention was made with Government support under contract HL064274 awarded by the National Institutes of Health. The Government has certain rights in the invention.

FIELD OF THE INVENTION

This invention pertains to genome editing in the absence of exogenous nucleases.

BACKGROUND OF THE INVENTION

Site-specific manipulation of the genome is a desirable goal for many applications in medicine, biotechnology, and biological research. In recent years much effort has been made to develop site-specific nucleases for gene targeting in mitotic and post-mitotic cells in vitro and in vivo. However, these targeted nucleases are often toxic to cells and their off target activity may be immunogenic and genotoxic. What is needed in the art are methods for editing the genome of a cell without the use of exogenously provided nucleases. The present invention addresses these issues.

SUMMARY OF THE INVENTION

Methods and compositions are provided for editing the genome of a cell without the use of an exogenously supplied nuclease. Aspects of the methods include contacting a cell with a targeting vector comprising nucleic acid sequence to be integrated into the target locus, where the cell is not also contacted with a nuclease. In addition, reagents, devices and kits thereof that find use in practicing the subject methods are provided.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 6. Western blot analysis of liver. The size of the hF-IX band indicates efficient ribosomal skipping by the 2A peptide.

FIG. 8. Vector design and experimental scheme. A. The rAAV8 vector encodes a codon-optimized hF9 cDNA and preceding 2A-peptide coding sequence flanked by homology arms directing integration 5' to the Alb stop codon. Length of the 5' and 3' arms are 1.3 and 1.4-kb, respectively. Following integration by homologous recombination, Alb and hF9 are fused at the DNA and RNA levels, but two separate proteins are produced as the result of ribosomal skipping. B. With respect to the Alb homology arms, the AAV inverse control has hF9 inverted along with the 2A-peptide coding sequence, the adjacent Alb exon and the preceding splice junction. Thin white rectangles: Alb introns; thick dark gray rectangles: Alb exons; thick white rectangles: P2A; thick white arrows: hF9; thick light gray rectangles: extragenic DNA; dashed lines: stop codon; ellipsoids: inverted terminal repeats; P=proline.

FIG. 9. Human factor IX expression and activity in injected mice. A. Plasma hF9 measured by ELISA following IP injections of 2-day-old B6 mice with 2.5e11 vg of either the hF9 experimental construct (n=6) or inverse control (n=3). Measurements below the detection limit were assigned a threshold value of 20 ng/mL. PH=partial hepatectomy. Error bars represent standard deviation. Dashed lines denote 5% and 20% of normal F9 levels. B. Plasma hF9 measured by ELISA following tail vain injections of 9-week-old B6 mice with 1e12 vg of either the AAV hF9 experimental construct (n=7), or inverse control (n=3), or a hydrodynamic injection of 30 μg plasmid (3.5e12 copy number) coding for the hF9 construct in the "correct" orientation. The limit of detection was 20 ng/mL. Error bars and dashed lines as in (A). C. Plasma hF9 measured by ELISA following tail vain injections of 9-week-old B6 mice with the designated MOI of AAV hF9 experimental construct (n=4 for each group). Error bars represent standard deviation. D. Measurement of coagulation efficiency by activated partial thromboplastin time (aPTT) 2 weeks after tail vain injections of 1e12 AAV8-hF9 vg per mouse (n=5). Error bars represent standard deviation. E. Western blot analysis for hF9 in liver samples from mice injected with the AAV8-hF9 construct or inverse control. The expected size of hF9 is 55-Kd.

FIG. 10. Rate of Alb targeting at the DNA and RNA levels. A. Assessment of on-target integration rate begins using linear amplification (LAM) with biotinylated primer 1 (black), annealing to the genomic locus but not to the vector. Linear amplicons are then bound to streptavidinylated beads and washed to exclude episomal vectors. Subsequent second-strand DNA synthesis with random primers was followed by CviQI restriction digestion. A compatible linker is then ligated, followed by two rounds of nested PCR (primers 2-3 in blue, and then primers 4-5 in red). CviQI cleaves at the same distance from the homology border in both targeted and wild-type alleles, thus allowing for unbiased amplification. The amplicons of the $2^{nd}$ nested PCR then serve as a template for qPCR assays with either primers 6-7 (green) or 8-9 (orange). B. For mRNA quantification, primers 10-11 or 11-12 were used to generate a cDNA for qPCR assays. Shape and fill code as in FIG. 1. C. Black bars represent the targeting rate of Alb alleles as the ratio between the abundance of the DNA template amplified by primers 6-7 to the abundance of the DNA template amplified by primers 8-9, corrected by a factor of 0.7 to account for hepatocyte frequency. Gray bars represent the expression rate of targeted Alb alleles as the ratio between the abundance of the cDNA template amplified by primers 10-11 to the abundance of the cDNA template amplified by primers 11-12. N=3 for each group, error bars represent standard deviation.

FIG. 11. Specificity of hF9 expression. A. cDNA, produced from RT with a poly-dT primer, served as a template for either a qPCR assay with primers 13-14 or 14-15. B. Bars represent the rate of Alb_hF9 mRNAs to total hF9-containing mRNAs as the ratio between the abundance of the cDNA template amplified by primers 13-14 to the abundance of the cDNA template amplified by primers 14-15. N=3 for each group, error bars represent standard deviation. C. Northern blot analysis of liver samples with a probe against P2A. The lower non-specific signal corresponds in size to 18S rRNA. D. Western blot analysis of P2A from liver samples of mice injected with the AAV-P2A-hF9 construct or inverse control. P2A is expected to be fused to Albumin (66.5-Kd).

FIG. 13. Scheme of targeting rate assessment. Assessment of on-target integration rate begins using linear amplification (LAM) with biotinylated primer 1 (black), annealing to the genomic locus but not to the vector (step 1). Linear amplicons are then bound to streptavidinylated beads and washed to exclude episomal vectors (Step 2). Subsequent second-strand DNA synthesis with random primers (Step 3) was followed by CviQI restriction digestion (Step 4). A compatible linker is then ligated (Step 5) followed by two rounds of nested PCR amplifications (primers 2-3 in blue-Step 6, and then primers 4-5 in red-Step 7). CviQI cleaves at the same distance from the homology border in both targeted and wild-type alleles, thus allowing for unbiased amplification. The amplicons of the $2^{nd}$ nested PCR then serve as a template for qPCR assays with either primers 6-7 (green) or 8-9 (orange) (Step 8).

FIG. 14. Standard curves for targeting rate assessment by qPCR. qPCR standard curves for the targeted allele (primers 8 and 9, FIG. 3) and non-targeted allele (primers 6 and 7, FIG. 3). Mass units used are functionally equivalent to molarity because all amplicons used were of equal length.

FIG. 17. Haplotypes in the human population at the relevant Alb locus as extracted from the 1000 genomes project ("http:" followed by "//www." followed by "1000genomes" followed by ".org").

FIG. 19. Measurement of coagulation efficiency by activated partial thromboplastin time (aPTT) 2 weeks after tail vein injections of AAV8-F9 at $1\times10^{12}$ vector genomes per mouse (top) or of AAV8-F9 Triple at $3\times10^{11}$ vector genomes per mouse (bottom) (n=5 each). KO, knockout. Error bars represent standard deviation.

DETAILED DESCRIPTION OF THE INVENTION

Figure 1:
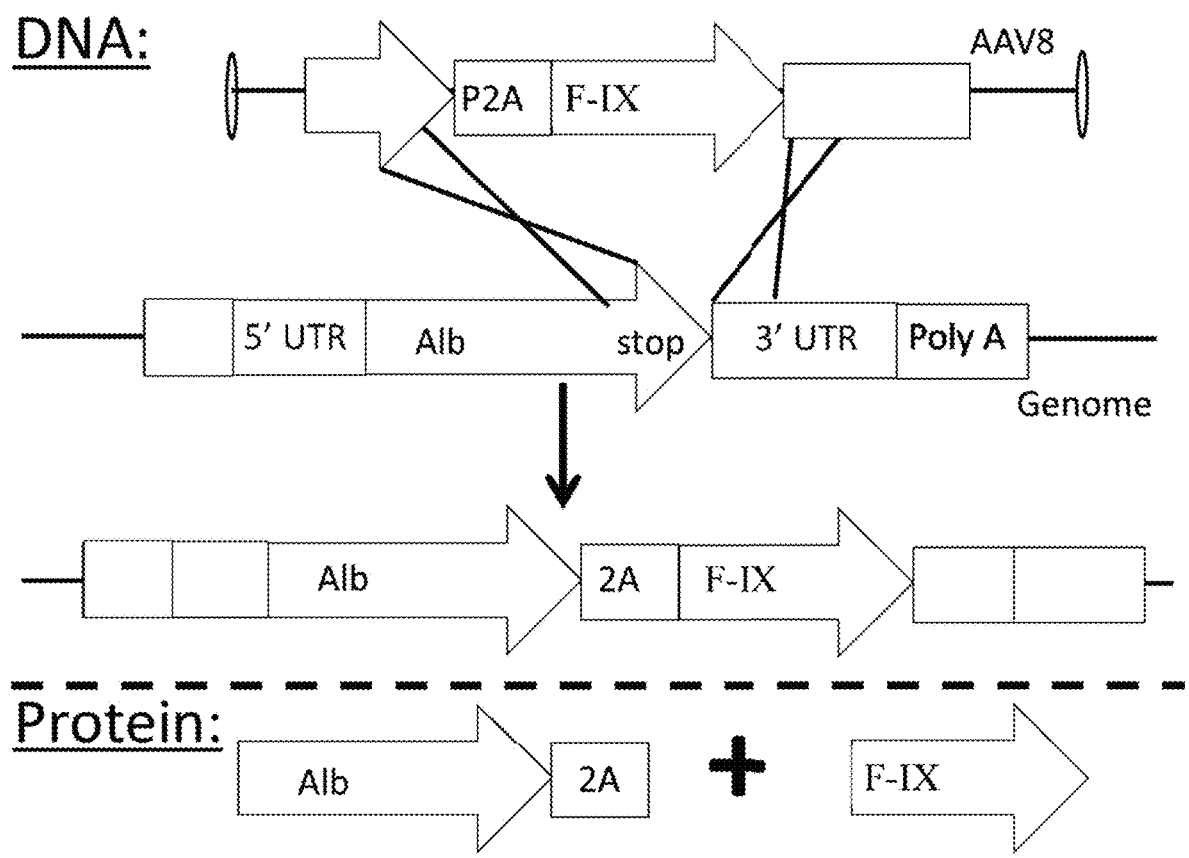
FIG. 1. Vector design and targeting scheme: A codon optimized human F-IX cDNA (light green) is preceded by a sequence coding a 2A peptide (P2A, dark green). It is flanked by sequences that are homologous to those spanning the Albumin Stop codon from the 5' (blue) and 3' (UTR, yellow). The homology arms are 1.3 and 1.4 Kb long, respectively. Integration into the Alb locus results in a chimeric gene. However, Ribosomal skipping induced by the 2A peptide allows the production of two separate proteins. The Albumin protein is left with a 21 amino acid long 2A tag while the clotting factor is linked to an N terminal Proline that is later processed in the ER as part of the signal peptide.
Figure 2:
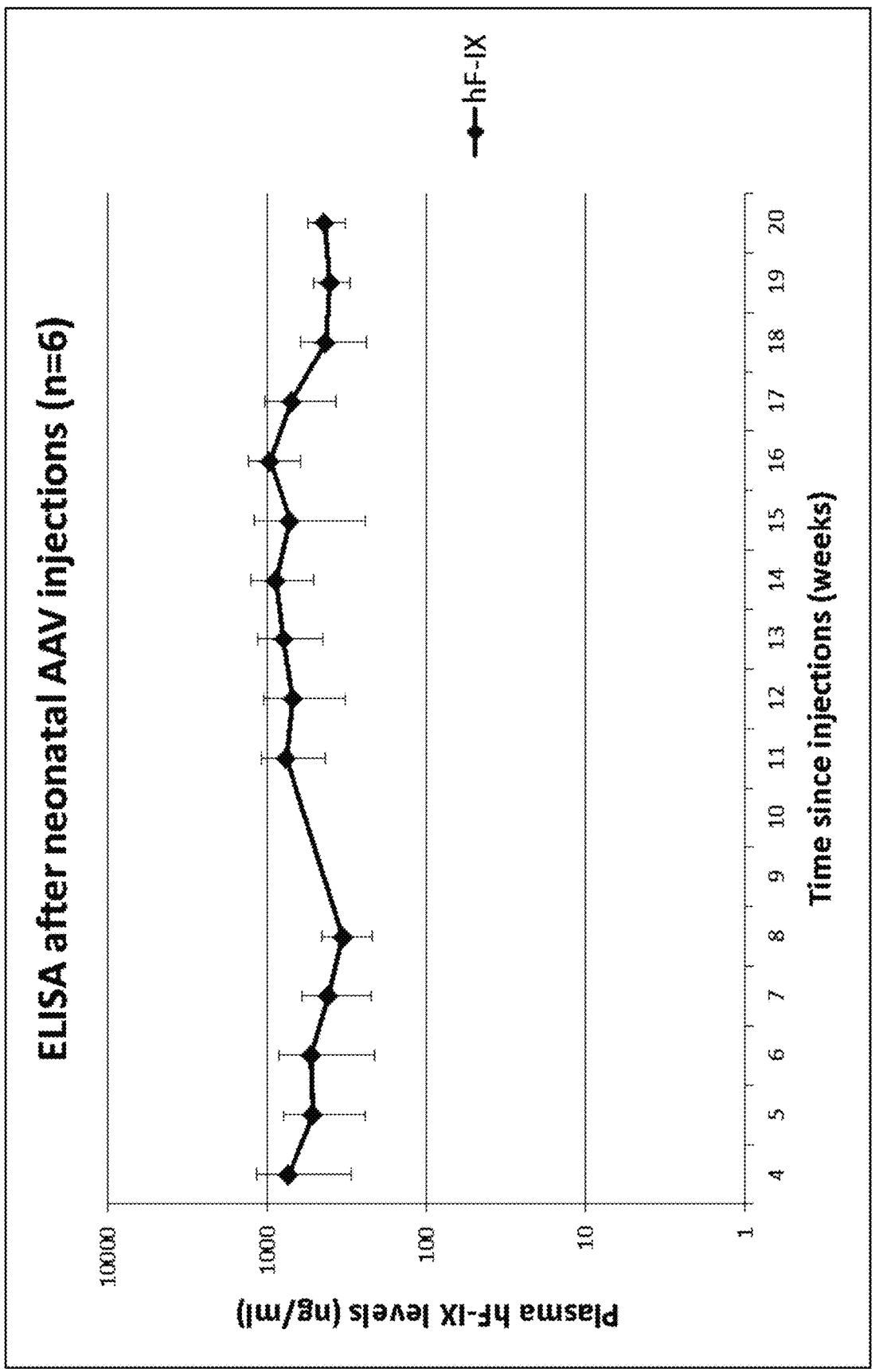
FIG. 2. Two day old C57BL/6J (B6) mice were injected intraperitoneally (IP) by 50 ul containing 2.5e11 vector particles, as tittered by dot blot. Plasma hF-IX was assessed weekly by ELISA, starting at week 4 of life, following retro-orbital blood collection. N=6, error bars represent standard deviation.
Figure 3:
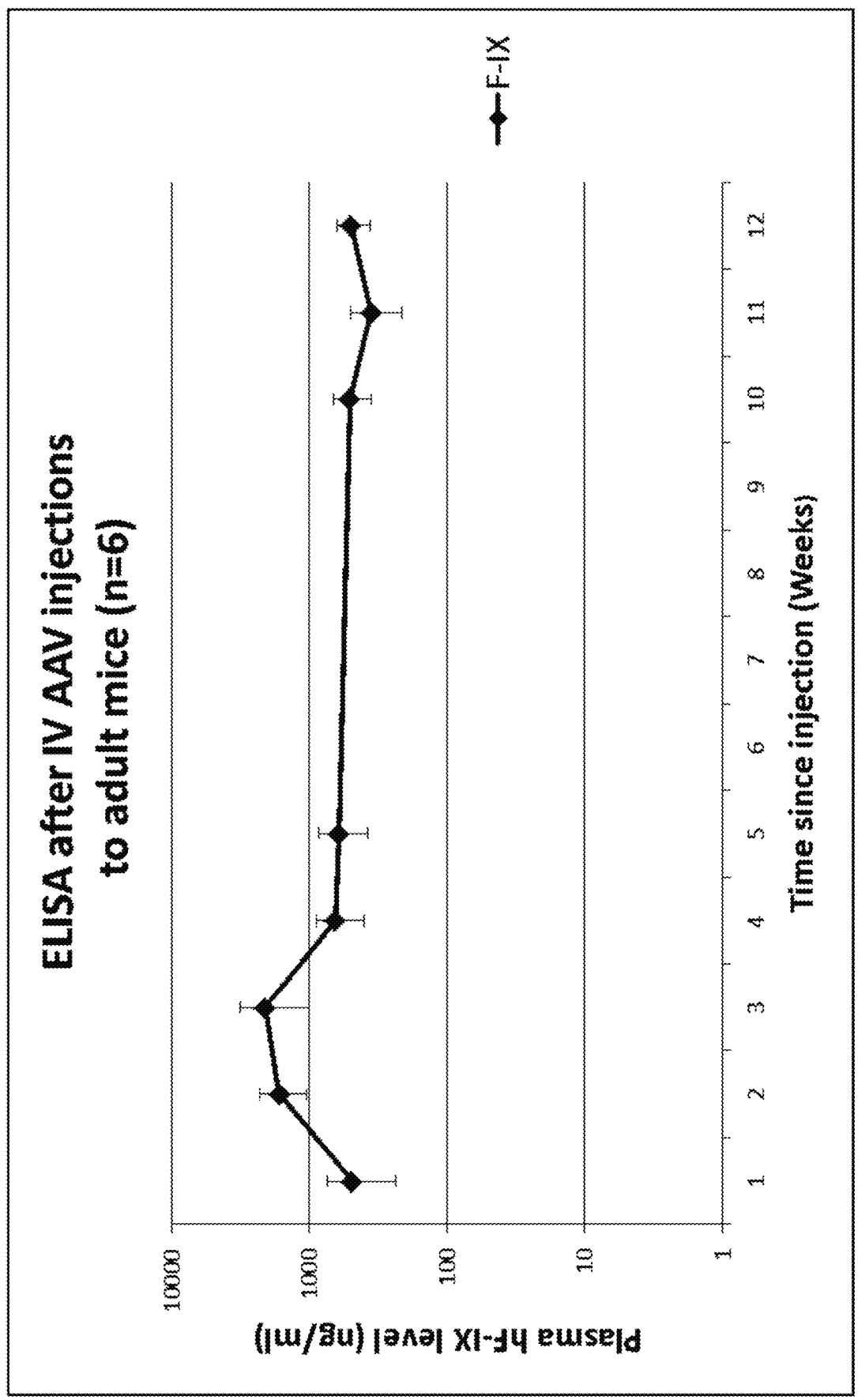
FIG. 3. Adult C57BL/6J (B6) mice were injected intravenously (IV) by 100 ul containing 1e12 vector particles, as tittered by dot blot. Plasma hF-IX was assessed weekly by ELISA, starting at week 4 of life, following retro-orbital blood collection. N=3, error bars represent standard deviation.
Figure 4:
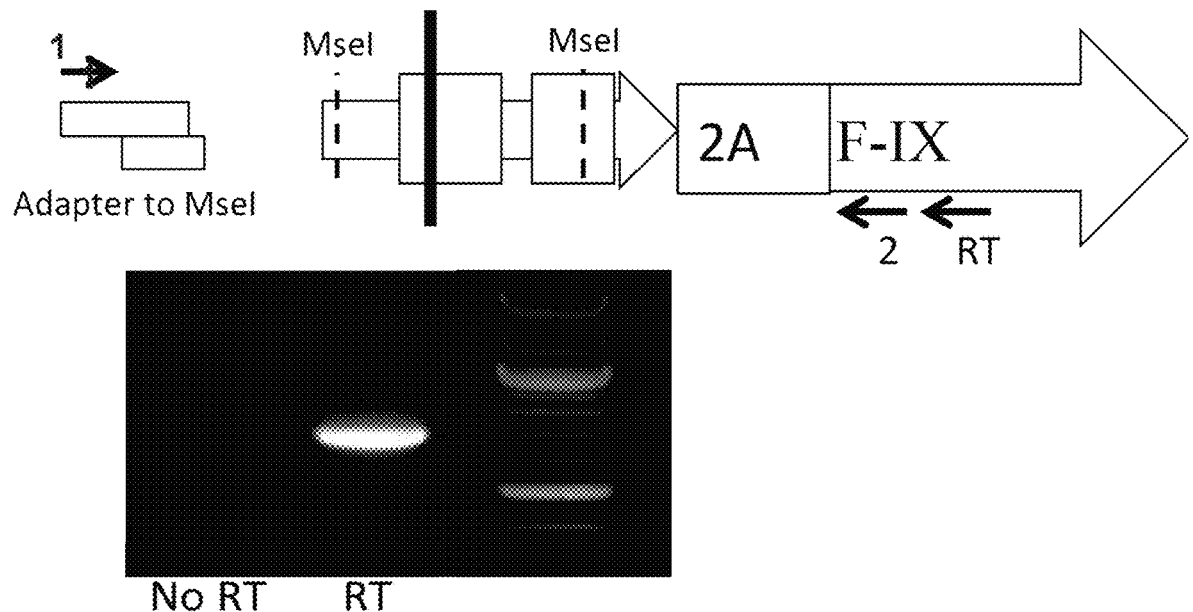
FIG. 4. RT unbiased PCR showing that hF-IX is expressed from on-target integration. Reverse transcription was performed with primer RT (UP) followed by second strand DNA synthesis with random primers, cleavage with the MseI restriction enzyme, linker ligation and PCR with primer pair 1&2. Blue: Alb exons, Orange: Alb introns, solid black line: end of homology between the vector and the genome. The PCR product (Down) was sequenced and found to correspond to a fused Albumin_F-IX transcript as expected from on-target integration. The unbiased approach gave rise to no PCR products corresponding to episomal expression or to off-target integration.
Figure 5:
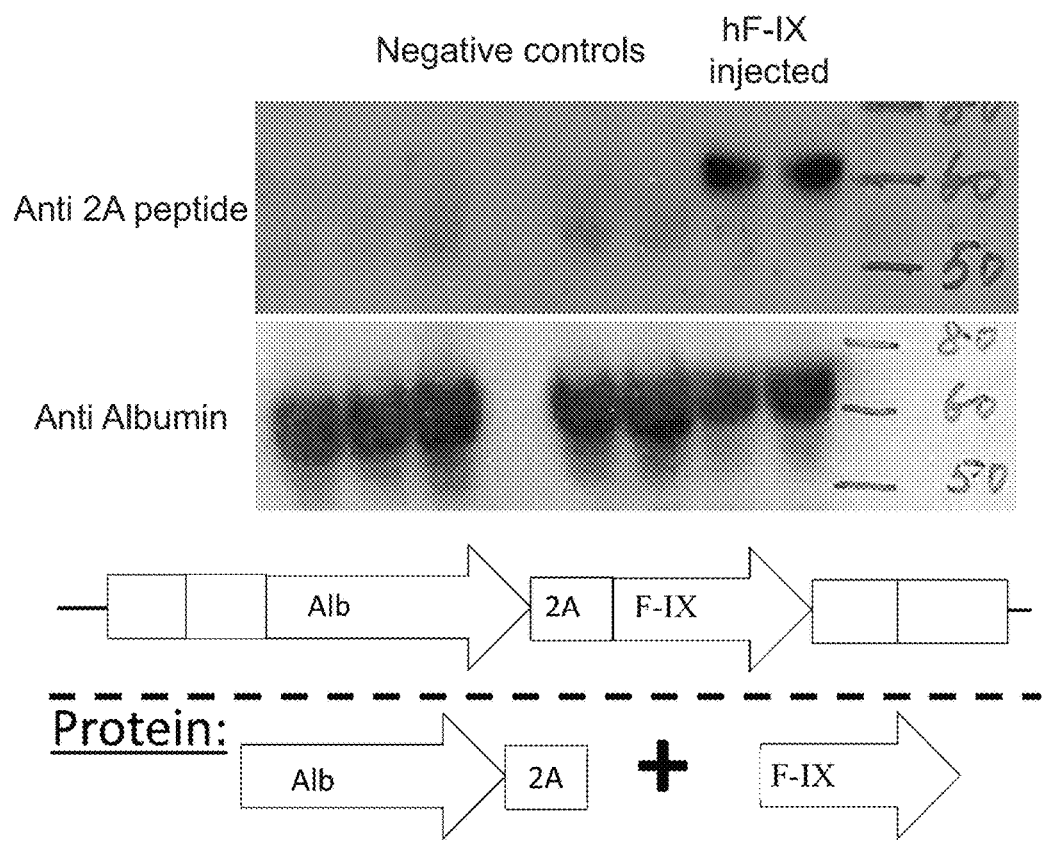
FIG. 5. Western blot analysis of plasma showing a single anti-2A band of the size of Albumin, indicating only on-target expression.
Figure 7:
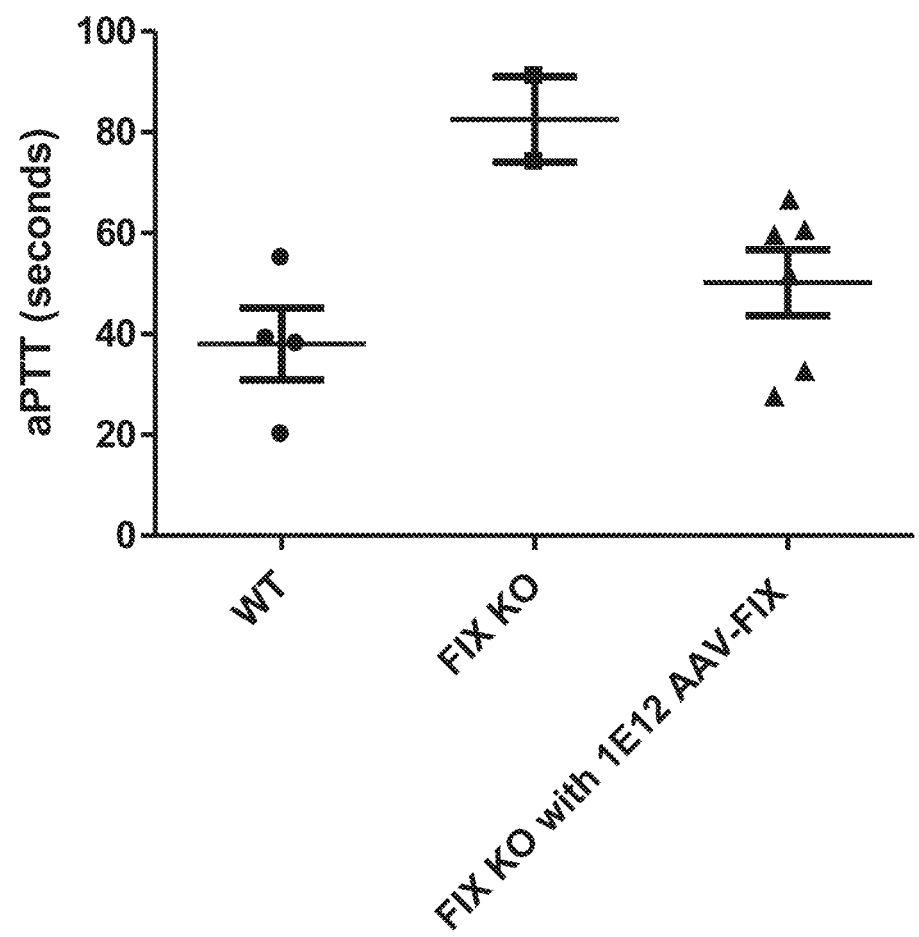
FIG. 7. Phenotypic correction in F-IX knock-out mice (a cross of B6 and CD-1). Adult mice were injected with 1×10^12 vector genomes (Vg) of AAV8_hF-IX. Coagulation time was measured by aPTT assay two weeks post injection. Mice injected with the AAV8_hF-IX targeting vector show much improved coagulation times.

Methods and compositions are provided for editing the genome of a cell without the use of an exogenously supplied nuclease. Aspects of the methods include contacting a cell with a targeting vector comprising nucleic acid sequence to be integrated into the target locus, where the cell is not also contacted with a nuclease. In addition, reagents, devices and kits thereof that find use in practicing the subject methods are provided. These and other objects, advantages, and features of the invention will become apparent to those persons skilled in the art upon reading the details of the compositions and methods as more fully described below.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods and compositions are provided for editing the genome of a cell. By genome editing, it is meant genetic engineering in which a nucleic acid sequence of interest is inserted, replaced, or removed from a genome. In the present instance, the subject methods and compositions find particular use in inserting a nucleic acid sequence to be expressed in a cell, referred to herein as a "transgene", into the cell's genome at a target locus. In some instances, the transgene encodes an RNA that codes for a peptide or polypeptide. In other instances, the transgene encodes for a non-coding RNA, i.e. an RNA that does not encode a peptide or protein, e.g. a nucleic acid sequence that encodes for a ribozyme, a small hairpin RNA (shRNA), a microRNA (miRNA), or a precursor thereof, a long-noncoding RNA, etc. In some instances, one transgene is inserted into the target locus. In other instances, more than one transgene is inserted, e.g. 2, 3, 4, or 5 or more transgenes are inserted into the target locus. In some instances, the subject transgene(s) becomes operably linked to the promoter of the endogenous gene at the target locus upon integration into the target integration site. In other instances, the subject transgene is operably linked to a promoter on the viral vector, and remains operably linked to that promoter upon integration into the target integration site.

In practicing the subject methods, the genome of the cell is edited without the use of an exogenous nuclease. By a "nuclease" it is meant an enzyme that is capable of cleaving the phosphodiester bonds between nucleotide subunits of DNA, e.g. genomic DNA or mitochondrial DNA, to create a double strand break. Many examples of nucleases are known in the art, including the artificially engineered Zinc finger nucleases (ZFNs), Transcription Activator-Like Effector Nucleases (TALENs), the CRISPR/Cas system, and engineered meganuclease re-engineered homing endonucleases, and naturally occurring nucleases such as restriction endonucleases, RecBCD endonuclease, T7 endonuclease, T4 endonuclease IV, Bal 31 endonuclease, Endonuclease I (endo I), Endonuclease II (endo VI, exo III), Micrococcal nuclease, Neurospora endonuclease, S1-nuclease, P1-nuclease, Mung bean nuclease I, Ustilago nuclease, Dnase I, AP endonuclease, and EndoR. By an exogenous nuclease, it is meant a nucleases that comes from the outside of the cell, for example, a nuclease or a nucleic acid encoding a nuclease that is present and active in a living cell but that originated outside of that cell. As demonstrated in the working examples herein, targeted genome editing in a cell may be achieved without providing nucleases to the cell, i.e. without contacting the cell with nuclease or a nucleic acid encoding a nuclease.

Genome editing without the use of an exogenous nuclease provides a number of benefits over methods that require the use of an exogenous nuclease. For example, nucleases can be immunogenic, as can vectors that deliver a nuclease coding gene. In addition, nuclease activity can be genotoxic due to both target-specific and off-target cleavage. Furthermore, the introduction of a nuclease coding sequence into a cell also carries with it the risk of possible integration of the nuclease coding sequence into the genome and subsequent stable expression of the nuclease, leading to an even greater risk of immunogenicity and genotoxicity as well as the activation of nearby genes by the promoter driving expression of the nuclease or by other promoters present on the vector coding for the nucleases. Use of a nuclease-free method removes these risks.

In practicing the subject methods, the transgene to be integrated into the genome of the cell is provided to cells on a vector, referred to herein as a "targeting vector". In other words, cells are contacted with a targeting vector that comprises the nucleic acid sequence to be integrated into the cellular genome by targeted integration. In the detailed description that follows, compositions comprising targeting vectors will be described, followed by exemplary methods for their use.

Compositions

In aspects of the invention, compositions are provided that find use in genome editing, e.g. by the methods of the disclosure. In some embodiments, the composition is a targeting vector. As discussed above, a targeting vector refers to a vector comprising a transgene to be integrated into the genome of the cell. Examples of targeting vectors encompassed by the present invention include viral vectors and non-viral vectors, e.g., plasmids, minicircles, and the like.

In some embodiments, the targeting vector is a viral vector. A viral vector refers to a virus or viral chromosomal material into which a fragment of foreign DNA can be inserted for transfer into a cell. Any virus that includes a DNA stage in its life cycle may be used as a viral vector in the subject methods and compositions. For example, the virus may be a single strand DNA (ssDNA) virus or a double strand DNA (dsDNA) virus. Also suitable are RNA viruses that have a DNA stage in their lifecycle, for example, retroviruses, e.g. MMLV, lentivirus, which are reverse-transcribed into DNA. The virus can be an integrating virus or a non-integrating virus.

As one non-limiting example, one virus of interest is adeno-associated virus. By adeno-associated virus, or "AAV" it is meant the virus itself or derivatives thereof. The term covers all subtypes and both naturally occurring and recombinant forms, except where required otherwise, for example, AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), AAV type 10 (AAV-10), AAV type 11 (AAV-11), avian AAV, bovine AAV, canine AAV, equine AAV, primate AAV, non-primate AAV, ovine AAV, a hybrid AAV (i.e., an AAV comprising a capsid protein of one AAV subtype and genomic material of another subtype), an AAV comprising a mutant AAV capsid protein or a chimeric AAV capsid (i.e. a capsid protein with regions or domains or individual amino acids that are derived from two or more different serotypes of AAV, e.g. AAV-DJ, AAV-LK3, AAV-LK19). "Primate AAV" refers to AAV that infect primates, "non-primate AAV" refers to AAV that infect non-primate mammals, "bovine AAV" refers to AAV that infect bovine mammals, etc.

By a "recombinant AAV vector", or "rAAV vector" it is meant an AAV virus or AAV viral chromosomal material comprising a polynucleotide sequence not of AAV origin (i.e., a polynucleotide heterologous to AAV), typically a nucleic acid sequence of interest to be integrated into the cell following the subject methods. In general, the heterologous polynucleotide is flanked by at least one, and generally by two AAV inverted terminal repeat sequences (ITRs). In some instances, the recombinant viral vector also comprises viral genes important for the packaging of the recombinant viral vector material. By "packaging" it is meant a series of intracellular events that result in the assembly and encapsidation of a viral particle, e.g. an AAV viral particle. Examples of nucleic acid sequences important for AAV packaging (i.e., "packaging genes") include the AAV "rep" and "cap" genes, which encode for replication and encapsidation proteins of adeno-associated virus, respectively. The term rAAV vector encompasses both rAAV vector particles and rAAV vector plasmids.

A "viral particle" refers to a single unit of virus comprising a capsid encapsidating a virus-based polynucleotide, e.g. the viral genome (as in a wild type virus), or, e.g., the subject targeting vector (as in a recombinant virus). An "AAV viral particle" refers to a viral particle composed of at least one AAV capsid protein (typically by all of the capsid proteins of a wild-type AAV) and an encapsidated polynucleotide AAV vector. If the particle comprises a heterologous polynucleotide (i.e. a polynucleotide other than a wild-type AAV genome, such as a transgene to be delivered to a mammalian cell), it is typically referred to as an "rAAV vector particle" or simply an "rAAV vector". Thus, production of rAAV particle necessarily includes production of rAAV vector, as such a vector is contained within an rAAV particle.

The subject targeting vectors are configured to guide the integration of the transgene to a specific locus of interest, i.e., a "target locus", in the cell genome. In other words, the integration is a targeted integration. Examples of loci in mammals of particular interest for targeting include the albumin gene; a collagen gene, e.g. collagen type 1, collagen type 2, collagen type 3, collagen type 4, collagen type 5, collagen type 6, collagen type 7, collagen type 8, collagen type 9, collagen type 10, collagen type 11, collagen type 12, collagen type 13, collagen type 14, collagen type 15, collagen type 16, collagen type 17, collagen type 18, collagen type 19, collagen type 20, collagen type 21, collagen type 22, collagen type 23, collagen type 24, collagen type 25, collagen type 26, collagen type 27, collagen type 28; an actin gene, e.g. alpha actin, beta actin; etc.

To promote targeted integration, the targeting vector comprises nucleic acid sequences that are permissive to homologous recombination at the site of integration, e.g. sequences that are permissive to homologous recombination with the albumin gene, a collagen gene, an actin gene, etc. This process requires nucleotide sequence homology, using the "donor" molecule, e.g. the targeting vector, to template repair of a "target" molecule, i.e., the nucleic acid into which the nucleic acid of sequence is integrated, e.g. a target locus in the cellular genome, and leads to the transfer of genetic information from the donor to the target. As such, in targeting vectors of the subject compositions, the transgene to be integrated into the cellular genome may be flanked by sequences that contain sufficient homology to a genomic sequence at the cleavage site, e.g. 70%, 80%, 85%, 90%, 95%, or 100% homology with the nucleotide sequences flanking the cleavage site, e.g. within about 50 bases or less of the cleavage site, e.g. within about 30 bases, within about 15 bases, within about 10 bases, within about 5 bases, or immediately flanking the target integration site, to support homologous recombination between it and the genomic sequence to which it bears homology. Approximately 25, 50, 100, 250, or 500 nucleotides or more of sequence homology between a donor and a genomic sequence will support homologous recombination therebetween.

In some embodiments, the presence of the flanking sequences that are permissive to homologous recombination provide for an increased rate of target site integration, as compared to a vector lacking the flanking sequences or having flanking sequences that are not homologous to the target locus (e.g., flanking sequences that are homologous to a different genomic locus, flanking sequences with no homology to any location in the target genome, etc.). In some embodiments, 0.01% or more (e.g., 0.05% or more, 0.1% or more, 0.2% or more, 0.3% or more, 0.4% or more, 0.5% or more, 0.6% or more, 0.7% or more, 0.8% or more, 0.9% or more, 1% or more, 1.5% or more, 2% or more, 5% or more, 10% or more) of target loci among cells in a tissue or among cells receiving the targeting vector contain an integrated transgene following administration. Rate of integration into a target locus may be measured by any suitable assay (e.g., a linear amplification assay like the one described herein).

In some embodiments, transgene expression results substantially from integration at the target locus. For example, in some cases 75% or more (e.g., 80% or more, 85% or more, 90% or more, 95% or more, 99% or more, 99.5% or more) of the total transgene expression is from the transgene that has integrated at the target locus. In other words, in some cases, the relative fraction of transgene expression from sources other than integration at the target locus (e.g. episomal expression, or integration at a non-target locus) as compared to expression from integration at the target locus is 25% or less (e.g., 20% or less, 15% or less, 10% or less, 5% or less, 1% or less, 0.5% or less, etc.). The percent of expression from target-locus-based integration can be measured by any suitable assay, e.g., an assay disclosed herein.

The flanking recombination sequences can be of any length, e.g. 10 nucleotides or more, 50 nucleotides or more, 100 nucleotides or more, 250 nucleotides or more, 500 nucleotides or more, 1000 nucleotides (1 kb) or more, 5000 nucleotides (5 kb) or more, 10000 nucleotides (10 kb) or more etc. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the targeting vector.

In some instances, the flanking sequences may be substantially equal in length to one another, e.g. one may be 30% shorter or less than the other flanking sequence, 20% shorter or less than the other flanking sequence, 10% shorter or less than the other flanking sequence, 5% shorter or less than the other flanking sequence, 2% shorter or less than the other flanking sequence, or only a few nucleotides less than the other. In other instances, the flanking sequences may be substantially different in length from one another, e.g. one may be 40% shorter or more, 50% shorter or more, sometimes 60% shorter or more, 70% shorter or more, 80% shorter or more, 90% shorter or more, or 95% shorter or more than the other flanking sequence.

Often, at least one flanking recombination sequence will comprise coding sequence for the gene at the target locus. For example, if the target integration site comprises the 3' end of the endogenous gene, the recombination sequence on the targeting vector that is 5' of the transgene will be substantially homologous to DNA sequence upstream of, e.g. adjacent to, the stop codon of the endogenous gene, while the recombination sequence on the targeting vector that is 3' of the transgene will be substantially homologous to the DNA sequence downstream of, e.g. adjacent to, the stop codon of the endogenous gene. As another example, if the target integration site comprises the 5' end of the endogenous gene, the recombination sequence on the targeting vector that is 5' of the transgene will be substantially homologous to the DNA sequence upstream of, e.g. adjacent to, the start codon of the endogenous gene, while the recombination sequence on the targeting vector that is 3' of the transgene will be substantially homologous to the DNA sequence downstream of, e.g. adjacent to, the start codon of the endogenous gene. Integrating coding sequence for the gene at the target locus into the target locus finds many uses. For example, integrating coding sequence for the gene at the target locus that is downstream, or 3', of the insertion site will ensure that the expression of the gene is not substantially disrupted by the integration of the gene of interest. As another example, it may be desirable to integrate coding sequence for the gene at the target locus so as to express a gene sequence that is a variant from that at the cell's target locus, e.g. if the gene at the cell's target locus is mutant, e.g. to complement a mutant target locus with wild-type gene sequence to treat a genetic disorder.

In some embodiments, it is desirable to edit the genome of the cell without substantially disrupting the expression of the gene at the edited locus. Towards this end, the targeting vector may also comprise one or more additional nucleic acid sequences that provide for the expression of the transgene without substantially disrupting the expression of the gene at the target locus. For example, the targeting vector may comprise a nucleic acid sequence that promotes the production of two independent gene products—the endogenous gene at the target locus, and the integrated transgene—upon integration of the transgene into the target integration site. Examples of such nucleic acid sequences include a sequence that encodes a 2A peptide; an IRES; an intein; a recognition sequence for a site specific protease (e.g. Furin), a sequence that encodes a cleavable linker that is cleaved as part of the coagulation cascade; a sequence that encodes a factor XI cleavage site; and intronic splice donor/splice acceptor sequences.

By a "2A peptide" it is meant a small (18-22 amino acids) peptide sequence that allows for efficient, concordant expression of discrete protein products within a single coding sequence, regardless of the order of placement of the genes within the coding sequence, through ribosomal skipping. 2A peptides are readily identifiable by their consensus motif (DVEXNPGP) and their ability to promote protein cleavage. Any convenient 2A peptide may be used in the targeting vector, e.g. the 2A peptide from a virus such as foot-and-mouth disease virus (F2A), equine Rhinitis A virus, porcine teschovirus-1 (P2A) or Thosea asigna virus (T2A), or any of the 2A peptides described in Szymczak-Workman, A. et al. "Design and Construction of 2A Peptide-Linked Multicistronic Vectors". Adapted from: *Gene Transfer: Delivery and Expression of DNA and RNA* (ed. Friedmann and Rossi). CSHL Press, Cold Spring Harbor, N.Y., USA, 2007, the disclosure of which is incorporated herein by reference.

Typically, the transgene and 2A peptide coding sequence will be positioned on the targeting vector so as to provide for uninterrupted expression, i.e. transcription, translation, and activity, of the endogenous gene at the target locus upon insertion of the transgene. For example, it may be desirable to insert the transgene into an integration site near the 5' end of the endogenous gene at the target locus, e.g., just downstream of the start codon of the endogenous gene at the target locus. In such instances, the 2A peptide coding sequence would be positioned within the targeting vector such that it is immediately 3' to the transgene, and flanking recombination sequences selected that will guide homologous recombination and integration of the transgene-2A peptide coding sequence cassette to the integration site just downstream of the start codon of the endogenous gene at the target locus. As another example, it may be desirable to insert the transgene into an integration site within the 3' end of the endogenous gene at the target locus, i.e. just upstream of the stop codon of the endogenous gene at the target locus. In such instances, the 2A peptide coding sequence would be positioned within the targeting vector such that it is immediately 5' to the transgene, and flanking recombination sequences selected that will guide homologous recombination and integration of the 2A-transgene cassette to the integration site just upstream of the stop codon of the endogenous gene at the target locus.

By an "internal ribosome entry site," or "IRES" it is meant a nucleotide sequence that allows for the initiation of protein translation in the middle of a messenger RNA (mRNA) sequence. For example, when an IRES segment is located between two open reading frames in a bicistronic eukaryotic mRNA molecule, it can drive translation of the downstream protein-coding region independently of the 5'-cap structure bound to the 5' end of the mRNA molecule, i.e. in front of the upstream protein coding region. In such a setup both proteins are produced in the cell. The protein located in the first cistron is synthesized by the cap-dependent initiation approach, while translation initiation of the second protein is directed by the IRES segment located in the intercistronic spacer region between the two protein coding regions. IRESs have been isolated from viral genomes and cellular genomes. Artificially engineered IRESs are also known in the art. Any convenient IRES may be employed in the donor polynucleotide.

Typically, as with the 2A peptide, the transgene and IRES will be positioned on the targeting vector so as to provide for uninterrupted expression of the gene at the target locus upon insertion of the transgene. For example, it may be desirable to insert the transgene into an integration site within the 5' untranslated region (UTR) of the gene at the target locus. In such instances, the IRES would be positioned within the targeting vector such that it is immediately 3' to the transgene, and flanking recombination sequences selected that will guide homologous recombination and integration of the transgene-IRES cassette to the integration site within the 5' UTR. As another example, it may be desirable to insert the transgene into an integration site within the 3' UTR of the gene at the target locus, i.e. downstream of the stop codon, but upstream of the polyadenylation sequence. In such instances, the IRES would be positioned within the targeting vector such that it is immediately 5' to the transgene, and flanking recombination sequences selected that will guide homologous recombination and integration of the IRES-transgene cassette to the integration site within the 3' UTR of the gene at the target locus.

By an "intein" it is meant a segment of a polypeptide that is able to excise itself and rejoin the remaining portions of the translated polypeptide sequence (the "exteins") with a peptide bond. In other words, the targeting vector comprises nucleic acid sequences that, when translated, promote excision of the protein encoded by the transgene from the polypeptide that is translated from the modified target locus. Inteins may be naturally occurring, i.e. inteins that spontaneously catalyze a protein splicing reaction to excise their own sequences and join the flanking extein sequences, or artificial, i.e. inteins that have been engineered to undergo controllable splicing. Inteins typically comprise an N-terminal splicing region comprising a Cys (C), Ser (S), Ala (A), Gln (Q) or Pro (P) at the most N-terminal position and a downstream TXXH sequence; and a C-terminal splicing region comprising an Asn (N), Gln (Q) or Asp (D) at the most C-terminal position and a His (H) at the penultimate C-terminal position. In addition, a Cys (C), Ser (S), or Thr (T) is located in the +1 position of the extein from which the intein is spliced (−1 and +1 of the extein being defined as the positions immediately N-terminal and C-terminal, respectively, to the intein insertion site). Mechanism by which inteins promote protein splicing and the requirements for intein splicing may be found in Liu, X-Q, "Protein Splicing Intein: Genetic Mobility, Origin, and Evolution" Annual Review of Genetics 2000, 34: 61-76 and in publicly available databases such as, for example, the InBase database on the New England Biolabs website, found on the world wide web at "tools(dot)neb(dot)com/inbase/mech(dot)php", the disclosures of which are incorporated herein by reference. Any sequences, e.g. N-terminal splicing regions and C-terminal splicing regions, known to confer intein-associated excision, be it spontaneous or controlled excision, on a donor polynucleotide, find use in the subject compositions. Genes of interest that are configured as inteins may be inserted at an integration site in any exon of a target locus, i.e. between the start codon and the stop codon of the gene at the target locus.

By a recognition sequence for a site specific protease, it is generally meant a nucleic acid sequence that encodes an amino acid sequence that is recognized by an enzyme that performs proteolysis. In some cases, such an amino acid sequence is referred to as a "cleavable linker." For example, in some cases the cleavable linker is cleaved as part of the coagulation cascade (e.g., in some cases, the recognition sequence for a site specific protease is a factor XI cleavage site). Non-limiting examples of proteases that are highly specific and the sequences that they cleave include thrombin (cleaves after the arginine residue at its cleavage site Leu-Val-Pro-Arg-Gly-Ser), TEV protease (cleaves after the glutamine residue at its cleavage site Glu-X-X-Tyr-X-Gln-Ser), Furin (cleaves protein after the last arginine of the sequence Arg-X-(Lys/Arg)-Arg), Enterokinase (cleaves after the lysine residue at its cleavage site Asp-Asp-Asp-Asp-Lys); Factor Xa (cleaves after the arginine residue at its cleavage site Ile-(Glu or Asp)-Gly-Arg); Genenase I (cleaves at the site Pro-Gly-Ala-Ala-His-Tyr); HRV 3C protease (cleaves after the glutamine residue at its cleavage site Leu-Glu-Val-Leu-Phe-Gln-Gly-Pro). In some embodiments, the cleavable linker is cleaved by an intracellular protease. In some embodiments, the cleavable linker is cleaved by an extracellular protease.

By an "intron" it is meant any nucleotide sequence within a gene that is removed by RNA splicing to generate the final mature RNA product of a gene. In other words, the targeting vector comprises nucleic acid sequences that, when transcribed, promote excision of the pre-RNA encoded by the gene of interest from the pre-RNA that is transcribed from the modified target locus, allowing the transgene to be translated separately (or not, if the transgene encodes an siRNA, miRNA, etc.) from the mRNA of the target locus. Introns typically comprise a 5' splice site (splice donor), a 3' splice site (spice acceptor) and a branch site. The splice donor includes an almost invariant sequence GU at the 5' end of the intron. The splice acceptor terminates the intron with an almost invariant AG sequence. Upstream (5'-ward) from the splice acceptor is a region high in pyrimidines (C and U) or a polypyrimidine tract. Upstream from the polypyrimidine tract is the branch point, which includes an adenine nucleotide. In addition to comprising these elements, the targeting vector may comprise one or more additional sequences that promote the translation of the mRNA transcribed from the gene of interest, e.g. a Kozak consensus sequence, a ribosomal binding site, an internal ribosome entry site, etc. Genes of interest that are configured as introns may be inserted at an integration site within the transcribed sequence of a target locus anywhere 5' of the nucleic acid sequence that encodes the polyadenylation sequence, e.g.

the 3' untranslated region, the coding sequence, or the 5' untranslated region of the gene at the target locus.

As discussed above, in some instances, it may be desirable to insert two or more genes of interest, e.g. three or more, 4 or more, or 5 or more genes of interest into a target locus. In such instances, multiple 2A peptides or IRESs may be used to create a bicistronic or multicistronic targeting vector. For example, a transgene and a selectable marker may be integrated into the 3' region of the gene at the target locus, with 2A peptides being used to promote their cleavage from the polypeptide encoded by the target locus and from one another. Alternatively, coding sequences of interest may be provided on the targeting vector under the control of a promoter distinct from that of the gene at the target locus.

Typically, the gene of interest, the 2A peptide, and the recombination sequences will be positioned on the targeting vector so as to provide for uninterrupted expression of the gene at the target locus upon insertion of the gene of interest. For example, as discussed above, it may be desirable to insert the transgene into an integration site that is 3', or "downstream" of the initiation codon of the gene at the target locus, for example, within the first 50 nucleotides 3' of the initiation codon (i.e. the start ATG) for the gene at the target locus, e.g. within the first 25 nucleotides 3' of initiation codon, within the first 10 nucleotides 3' of the initiation codon, within the first 5 nucleotides 3' of the initiation codon, or in some instances, immediately 3' of the initiation codon, i.e. adjacent to the initiation codon. In such instances, the 2A peptide would be positioned within the targeting vector such that it is immediately 3' to the gene of interest, and flanking recombination sequences selected that will guide homologous recombination and integration of the gene of interest to the integration site that is 3' of the initiation codon at the target locus. As another example, it may be desirable to insert the gene of interest into an integration site that is 5', or "upstream" of the termination codon of the gene at the target locus, for example, within the first 50 nucleotides 5' of the termination codon (i.e. the stop codon, e.g. TAA, TAG, or TGA), e.g. within the first 25 nucleotides 5' of termination codon, within the first 10 nucleotides 5' of the termination codon, within the first 5 nucleotides of the termination codon, or in some embodiments, immediately 5' of the termination codon, i.e. adjacent to the termination codon. In such instances, the 2A peptide would be positioned within the targeting vector such that it is immediately 5' to the gene of interest, and flanking recombination sequences selected that will guide homologous recombination and integration of the gene of interest to the integration site that is 5' of the termination codon at the target locus.

The targeting vector may also comprise sequences, e.g. restriction sites, nucleotide polymorphisms, selectable markers, etc., which may be used to assess for successful insertion of the gene of interest at the integration site. Typically, the targeting vector will also comprise a vector backbone containing sequences, e.g. viral sequences, e.g. replication origins, cap gene, rep gene, ITRs, etc., that are not homologous to the target region of interest and that are not intended for insertion into the target region of interest. Methods In practicing the subject methods, a cell, e.g. a mitotic cell, a post-mitotic cell, is contacted in vitro or in vivo with the targeting vector. In other words, the cells are contacted with targeting vector such that the targeting vector is taken up by the cells. The subject targeting vector can be introduced to the cell by any convenient method that results in the targeting vector being taken up by the cell, e.g. as naked nucleic acid, as nucleic acid complexed with an agent such as a liposome or poloxamer, as genomic material in a virus (e.g., adenovirus, AAV, retrovirus), etc. Methods for contacting cells with nucleic acid vectors that are plasmids, such as electroporation, calcium chloride transfection, and lipofection, are well known in the art, any of which may be used. Methods and systems for packaging nucleic acid vectors into viral capsids, harvesting the viral particles comprising the nucleic acid vector, and contacting cells with the viral particles comprising the nucleic acid vector are also well known in the art, any of which may be used. Once inside the cell, the targeting vector may be maintained episomally, e.g. as plasmids, minicircle DNAs, viruses such as adeno-associated virus, adenovirus, cytomegalovirus etc., or they may be integrated into the target cell genome, through homologous recombination or random integration, e.g. retrovirus-derived vectors such as MMLV, HIV-1, ALV, etc.

In some embodiments, the targeting vector is provided to the cells as viral particles comprising the targeting vector. In such instances, the targeting vector will typically comprise the subject nucleic acid sequence(s), e.g. transgene, nucleic acid sequence that promotes the production of two independent gene products, sequences of homology to the target integration site, etc., as heterologous sequences in association with viral genomic sequence, e.g. inverted terminal repeats (ITRs). Any virus that includes a DNA stage in its life cycle may be used as a viral vector in the subject methods and compositions. For example, the virus may be a single strand DNA (ssDNA) virus or a double strand DNA (dsDNA) virus. Also suitable are RNA viruses that have a DNA stage in their lifecycle, for example, retroviruses, e.g. MMLV, lentivirus, which are reverse-transcribed into DNA. The virus can be an integrating virus or a non-integrating virus.

Adeno-associated viruses, for example, are particularly suitable to the subject methods. By adeno-associated virus, or "AAV" it is meant the virus itself or derivatives thereof. The term covers all subtypes and both naturally occurring and recombinant forms, except where required otherwise, for example, AAV type 1 (AAV-1), AAV type 2 (AAV-2), AAV type 3 (AAV-3), AAV type 4 (AAV-4), AAV type 5 (AAV-5), AAV type 6 (AAV-6), AAV type 7 (AAV-7), AAV type 8 (AAV-8), AAV type 9 (AAV-9), avian AAV, bovine AAV, canine AAV, equine AAV, primate AAV, non-primate AAV, ovine AAV, a hybrid AAV (i.e., an AAV comprising a capsid protein of one AAV subtype and genomic material of another subtype), an AAV comprising a mutant AAV capsid protein or a chimeric AAV capsid (i.e. a capsid protein with regions or domains or individual amino acids that are derived from two or more different serotypes of AAV, e.g. AAV-DJ, AAV-LK3, AAV-LK19), etc.

An AAV expression vector comprising the heterologous nucleic acid sequences of interest, e.g. transgene, nucleic acid sequence that promotes the production of two independent gene products, sequences of homology to the target integration site, etc., and which is used to generate an rAAV virion can be constructed using methods that are well known in the art. See, e.g., Koerber et al. (2009) Mol. Ther. 17:2088; Koerber et al. (2008) Mol Ther. 16:1703-1709; U.S. Pat. Nos. 7,439,065, 6,951,758, and 6,491,907. For example, the heterologous sequence(s) can be directly inserted into an AAV genome which has had the major AAV open reading frames ("ORFs") excised therefrom. Other portions of the AAV genome can also be deleted, so long as a sufficient portion of the ITRs remain to allow for replication and packaging functions. Such constructs can be designed using techniques well known in the art. See, e.g., U.S. Pat. Nos. 5,173,414 and 5,139,941; International Publication Nos. WO 92/01070 (published Jan. 23, 1992) and WO 93/03769 (published Mar. 4, 1993); Lebkowski et al. (1988) Molec. Cell. Biol. 8:3988-3996; Vincent et al. (1990) Vaccines 90 (Cold Spring Harbor Laboratory Press); Carter, B. J. (1992) Current Opinion in Biotechnology 3:533-539; Muzyczka, N. (1992) Curr. Topics Microbiol. Immunol. 158:97-129; Kotin, R. M. (1994) Human Gene Therapy 5:793-801; Shelling and Smith (1994) Gene Therapy 1:165-169; and Zhou et al. (1994) J. Exp. Med. 179:1867-1875.

In order to produce rAAV virions, an AAV expression vector is introduced into a suitable host cell using known techniques, such as by transfection. A number of transfection techniques are generally known in the art. See, e.g., Graham et al. (1973) Virology, 52:456, Sambrook et al. (1989) Molecular Cloning, A Laboratory Manual, Cold Spring Harbor Laboratories, New York, Davis et al. (1986) Basic Methods in Molecular Biology, Elsevier, and Chu et al. (1981) Gene 13:197. Particularly suitable transfection methods include calcium phosphate co-precipitation (Graham et al. (1973) Virol. 52:456-467), direct micro-injection into cultured cells (Capecchi, M. R. (1980) Cell 22:479-488), electroporation (Shigekawa et al. (1988) BioTechnigues 6:742-751), liposome mediated gene transfer (Mannino et al. (1988) BioTechniques 6:682-690), lipid-mediated transduction (Feigner et al. (1987) Proc. Natl. Acad. Sci. USA 84:7413-7417), and nucleic acid delivery using high-velocity microprojectiles (Klein et al. (1987) Nature 327:70-73).

Suitable host cells for producing rAAV virions include microorganisms, yeast cells, insect cells, and mammalian cells, that can be, or have been, used as recipients of a heterologous DNA molecule. The term includes the progeny of the original cell which has been transfected. Thus, a "host cell" as used herein generally refers to a cell which has been transfected with an exogenous DNA sequence. Cells from the stable human cell line, 293 (readily available through, e.g., the American Type Culture Collection under Accession Number ATCC CRL1573) can be used. For example, the human cell line 293 is a human embryonic kidney cell line that has been transformed with adenovirus type-5 DNA fragments (Graham et al. (1977) J. Gen. Virol. 36:59), and expresses the adenoviral E1a and E1b genes (Aiello et al. (1979) Virology 94:460). The 293 cell line is readily transfected, and provides a convenient platform in which to produce rAAV virions. Methods of producing an AAV virion in insect cells are known in the art, and can be used to produce a subject rAAV virion. See, e.g., U.S. Patent Publication No. 2009/0203071; U.S. Pat. No. 7,271,002; and Chen (2008) Mol. Ther. 16:924.

AAV virus that is produced may be replication competent or replication-incompetent. A "replication-competent" virus (e.g. a replication-competent AAV) refers to a phenotypically wild-type virus that is infectious, and is also capable of being replicated in an infected cell (e.g., in the presence of a helper virus or helper virus functions). In the case of AAV, replication competence generally requires the presence of functional AAV packaging genes. In general, rAAV vectors as described herein are replication-incompetent in mammalian cells (especially in human cells) by virtue of the lack of one or more AAV packaging genes. Typically, such rAAV vectors lack any AAV packaging gene sequences in order to minimize the possibility that replication competent AAV are generated by recombination between AAV packaging genes and an incoming rAAV vector. In many embodiments, rAAV vector preparations as described herein are those which contain few if any replication competent AAV (rcAAV, also referred to as RCA) (e.g., less than about 1 rcAAV per 102 rAAV particles, less than about 1 rcAAV per 104 rAAV particles, less than about 1 rcAAV per 108 rAAV particles, less than about 1 rcAAV per 1012 rAAV particles, or no rcAAV).

Cells may be contacted with the subject targeting vectors, e.g. as a plasmid, as a virus, etc. in vitro or in vivo. If contacted in vitro, cells may be from established cell lines or they may be primary cells, where "primary cells", "primary cell lines", and "primary cultures" are used interchangeably herein to refer to cells and cells cultures that have been derived from a subject and either modified without significant additional culturing, i.e. modified "ex vivo", e.g. for return to the subject, or allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, the primary cell lines of the present invention are maintained for fewer than 10 passages in vitro. Typically, the cells to be contacted are permissive of homologous recombination.

If the cells are primary cells, they may be harvest from an individual by any convenient method. For example, leukocytes may be conveniently harvested by apheresis, leukocytapheresis, density gradient separation, etc., while cells from tissues such as skin, muscle, bone marrow, spleen, liver, pancreas, lung, intestine, stomach, etc. are most conveniently harvested by biopsy. An appropriate solution may be used for dispersion or suspension of the harvested cells. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

To induced DNA integration in vitro, the targeting vector, e.g. as a virus, is provided to the cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. The targeting vector may be provided to the subject cells one or more times, e.g. one time, twice, three times, or more than three times, and the cells allowed to incubate with the target vector for some amount of time following each contacting event e.g. 16-24 hours, after which time the media is replaced with fresh media and the cells are cultured further.

Contacting the cells with the targeting vector may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

Typically, an effective amount of targeting vector is provided to the cells to promote recombination and integration. An effective amount of target vector is the amount to induce a 2-fold increase or more in the number of cells in which integration of the transgene is observed relative to a negative control, e.g. a cell contacted with an empty vector. The amount of integration may be measured by any convenient method. For example, the presence of the gene of interest in the locus may be detected by, e.g., flow cytometry. PCR or Southern hybridization may be performed using primers that will amplify the target locus to detect the presence of the insertion. The expression or activity of the integrated gene of interest may be determined by Western, ELISA, testing for protein activity, etc. e.g. 2 hours, 4 hours, 8 hours, 12 hours, 24 hours, 36 hours, 48 hours, 72 hours or more after contact with the donor polynucleotide. As another example, integration may be measured by co-integrating an imaging marker or a selectable marker, and detecting the presence of the imaging or selectable marker in the cells.

Typically, genetic modification of the cell using the subject compositions and methods will not be accompanied by disruption of the expression of the gene at the modified locus, i.e. the target locus. In other words, the normal expression of the gene at the target locus is maintained spatially, temporally, and at levels that are substantially unchanged from normal levels, for example, at levels that differ 5-fold or less from normal levels, e.g. 4-fold or less, or 3-fold or less, more usually 2-fold or less from normal levels, following targeted integration of the gene of interest into the target locus.

In some instances, the population of cells may be enriched for those comprising the transgene by separating the genetically modified cells from the remaining population. Separation of genetically modified cells typically relies upon the expression of a selectable marker that is co-integrated into the target locus. By a "selectable marker" it is meant an agent that can be used to select cells, e.g. cells that have been targeted by compositions of the subject application. In some instances, the selection may be positive selection; that is, the cells are isolated from a population, e.g. to create an enriched population of cells comprising the genetic modification. In other instances, the selection may be negative selection; that is, the population is isolated away from the cells, e.g. to create an enriched population of cells that do not comprise the genetic modification. Separation may be by any convenient separation technique appropriate for the selectable marker used. For example, if a fluorescent marker has been inserted, cells may be separated by fluorescence activated cell sorting, whereas if a cell surface marker has been inserted, cells may be separated from the heterogeneous population by affinity separation techniques, e.g. magnetic separation, affinity chromatography, "panning" with an affinity reagent attached to a solid matrix, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the genetically modified cells.

Cell compositions that are highly enriched for cells comprising the transgene are achieved in this manner. By "highly enriched", it is meant that the genetically modified cells will be 70% or more, 75% or more, 80% or more, 85% or more, 90% or more of the cell composition, for example, about 95% or more, or 98% or more of the cell composition. In other words, the composition may be a substantially pure composition of genetically modified cells.

Genetically modified cells produced by the methods described herein may be used immediately. Alternatively, the cells may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

The genetically modified cells may be cultured in vitro under various culture conditions. The cells may be expanded in culture, i.e. grown under conditions that promote their proliferation. Culture medium may be liquid or semi-solid, e.g. containing agar, methylcellulose, etc. The cell population may be suspended in an appropriate nutrient medium, such as Iscove's modified DMEM or RPMI 1640, normally supplemented with fetal calf serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

Cells that have been genetically modified in this way may be transplanted to a subject for purposes such as gene therapy, e.g. to treat a disease or as an antiviral, antipathogenic, or anticancer therapeutic, for the production of genetically modified organisms in agriculture, or for biological research. The subject may be a neonate, a juvenile, or an adult. Of particular interest are mammalian subjects. Mammalian species that may be treated with the present methods include canines and felines; equines; bovines; ovines; etc. and primates, particularly humans. Animal models, particularly small mammals, e.g. murine, lagomorpha, etc. may be used for experimental investigations.

Cells may be provided to the subject alone or with a suitable substrate or matrix, e.g. to support their growth and/or organization in the tissue to which they are being transplanted. Usually, at least $1 \times 10^3$ cells will be administered, for example $5 \times 10^3$ cells, $1 \times 10^4$ cells, $5 \times 10^4$ cells, $1 \times 10^5$ cells, $1 \times 10^6$ cells or more. The cells may be introduced to the subject via any of the following routes: parenteral, subcutaneous, intravenous, intracranial, intraspinal, intraocular, or into spinal fluid. The cells may be introduced by injection, catheter, or the like. Examples of methods for local delivery, that is, delivery to the site of injury, include, e.g. through an Ommaya reservoir, e.g. for intrathecal delivery (see e.g. U.S. Pat. Nos. 5,222,982 and 5,385,582, incorporated herein by reference); by bolus injection, e.g. by a syringe, e.g. into a joint; by continuous infusion, e.g. by cannulation, e.g. with convection (see e.g. US Application No. 20070254842, incorporated here by reference); or by implanting a device upon which the cells have been reversably affixed (see e.g. US Application Nos. 20080081064 and 20090196903, incorporated herein by reference). The number of administrations of treatment to a subject may vary. Introducing the genetically modified cells into the subject may be a one-time event; but in certain situations, such treatment may elicit improvement for a limited period of time and require an on-going series of repeated treatments. In other situations, multiple administrations of the genetically modified cells may be required before an effect is observed. The exact protocols depend upon the disease or condition, the stage of the disease and parameters of the individual subject being treated.

In other aspects of the invention, the targeting vector is employed to modify cellular DNA in vivo. In these in vivo embodiments, the targeting vector is administered directly, e.g. as a virus to the individual. Targeting vector may be administered by any of a number of well-known methods in the art for the administration of nucleic acids to a subject. The targeting vector can be incorporated into a variety of formulations. More particularly, targeting vectors of the present invention can be formulated into pharmaceutical compositions by combination with appropriate pharmaceutically acceptable carriers or diluents.

Pharmaceutical preparations are compositions that include a targeting vector, e.g. as a virus, present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. As such, administration of the targeting vector can be achieved in various ways, including oral, buccal, rectal, parenteral, intraperitoneal, intraocular, intradermal, transdermal, intracheal, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

For some conditions, particularly central nervous system conditions, it may be necessary to formulate agents to cross the blood-brain barrier (BBB). One strategy for drug delivery through the blood-brain barrier (BBB) entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the therapeutic compositions of the invention when the compositions are administered by intravascular injection. Other strategies to go through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of therapeutics agents behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the agent has been reversably affixed (see e.g. US Application Nos. 20080081064 and 20090196903, incorporated herein by reference).

Typically, an effective amount of targeting vector is provided. As discussed above with regard to ex vivo methods, an effective amount or effective dose of a targeting vector in vivo is the amount to induce a 2-fold increase or more in the number of cells in which recombination between the targeting vector and the target locus can be observed relative to a negative control, e.g. a cell contacted with an empty vector or irrelevant polypeptide. The amount of recombination may be measured by any convenient method, e.g. as described above and known in the art. The calculation of the effective amount or effective dose of a targeting vector to be administered is within the skill of one of ordinary skill in the art, and will be routine to those persons skilled in the art. Needless to say, the final amount to be administered will be dependent upon the route of administration and upon the nature of the disorder or condition that is to be treated.

The effective amount given to a particular patient will depend on a variety of factors, several of which will differ from patient to patient. A competent clinician will be able to determine an effective amount of a targeting vector to administer to a patient to halt or reverse the progression the disease condition as required. Utilizing $LD_{50}$ animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

For inclusion in a medicament, the targeting vector may be obtained from a suitable commercial source. As a general proposition, the total pharmaceutically effective amount of the targeting vector administered parenterally per dose will be in a range that can be measured by a dose response curve.

Targeting vector-based therapies must be sterile. Sterility is readily accomplished by filtration through sterile filtration membranes (e.g., 0.2 μm membranes). Therapeutic compositions generally are placed into a container having a sterile access port, for example, an intravenous solution bag or vial having a stopper pierceable by a hypodermic injection needle. The targeting vector-based therapies may be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents. The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred.

In some embodiments, a pharmaceutical composition administered to a subject in an effective amount exhibits little to no liver toxicity (e.g., exhibits no substantial liver toxicity, does not exhibit substantial liver toxicity, is substantially non-toxic to the liver, etc.). Liver toxicity may be measured in a variety of ways, such as measuring levels of one, both, or a ratio of alanine aminotransferase (ALT) and aspartate aminotransferases (ASP). In some embodiments, administering an effective amount of the pharmaceutical composition induces an increase in liver toxicity (e.g., as measured by a selected convenient assay) of less than 50% (e.g., less than 40%, less than 30%, less than 20%, less than 15%, less than 10%, less than 5%, less than 4%, less than 3%, less than 2%, less than 1%, less than 0.5%, or 0%) as compared to such measure of liver toxicity prior to such administration (or as compared to an untreated control or as compared to an accepted normal range of values, i.e., reference values, for the measure). In some embodiments, administering an effective amount of the pharmaceutical composition induces no statistically significant increase in the measure of liver toxicity (e.g. at a p-value of less than 0.1, 0.05, 0.01, or lower) as compared to such measure prior to such administration (or as compared to an untreated control or as compared to an accepted normal range of values, i.e., reference values, for the measure). In some embodiments, administering an effective amount of the pharmaceutical composition reduces a measure of liver toxicity (e.g., as may result when the condition treated by the administration was causing liver toxicity) by 5% or more (e.g., 10% or more, 15% or more, 20% or more, 30% or more, 40% or more, 50% or more, etc.) as compared to such measure prior to such administration (or as compared to an untreated control or as compared to an accepted normal range of values, i.e., reference values, for the measure).

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions. The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Utility

The methods and compositions disclosed herein find use in any in vitro or in vivo application in which it is desirable to express a transgene from a particular locus in a cell, for example when it is desirable to express one or more transgenes in a cell in the same spatially and temporally restricted pattern as that of an endogenous gene at a target locus, while maintaining the expression of that endogenous gene at that target locus and while avoiding the risk of using an exogenous nuclease. By using the subject methods and compositions to edit the genome of the cell, a number of benefits may be achieved over methods that require the use of an exogenous nuclease. For example, use of the subject methods and compositions will avoid the potential immunogenicity and genotoxicity that is associated with providing an exogenous nuclease to a cell, be it as a polypeptide or a coding nucleic acid. The risk of possible integration of the nuclease coding sequence into the genome and subsequent stable expression of the nuclease, which may result in enhanced immunogenicity and genotoxicity as well as the activation of nearby genes by the promoter driving expression of the nuclease, is also avoided.

The subject methods and compositions for integrating one or more transgenes into cellular DNA at a target locus finds use in many fields, including, for example, gene therapy, agriculture, biotechnology, and research. For example, such modifications are therapeutically useful, e.g. to treat a genetic disorder by complementing a genetic mutation in a subject with a wild-type copy of the gene; to promote naturally occurring processes, by promoting/augmenting cellular activities (e.g. promoting wound healing for the treatment of chronic wounds or prevention of acute wound or flap failure, by augmenting cellular activities associated with wound healing); to modulate cellular response (e.g. to treat diabetes mellitus, by providing insulin); to express antiviral, antipathogenic, or anticancer therapeutics in subjects, e.g. in specific cell populations or under specific conditions, etc. Other uses for such genetic modifications include in the induction of induced pluripotent stem cells (iPSCs), e.g. to produce iPSCs from an individual for diagnostic, therapeutic, or research purposes; in the production of genetically modified organisms, for example in manufacturing for the large scale production of proteins by cells for therapeutic, diagnostic, or research purposes; in agriculture, e.g. for the production of improved crops; or in research, e.g. for the study of animal models of disease.

For example, the subject methods and compositions may be used to treat a disorder, a disease, or medical condition in a subject. The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease. The terms "individual," "subject," "host," and "patient," are used interchangeably herein and refer to any mammalian subject for whom diagnosis, treatment, or therapy is desired, particularly humans.

Towards this end, the one or more transgenes of the subject compositions may include a gene that encodes a therapeutic agent. By a "therapeutic agent" it is meant an agent, e.g. ribozyme, siRNA, shRNA, miRNA, peptide, polypeptide, etc. that has a therapeutic effect upon a cell or an individual, for example, that promotes a biological process to treat a medical condition, e.g. a disease or disorder.

Examples of therapeutic agents that may be integrated into a cellular genome using the subject methods and compositions include (i.e., the integrated transgene encodes) agents such as ribozymes, siRNAs, shRNAs, miRNAs, peptides (e.g., a nucleic acid encoding a peptide), or polypeptides (e.g., a nucleic acid encoding a polypeptide) which alter cellular activity. In some instances, the transgene encodes a peptide or polypeptide. Example of peptide or polypeptides envisioned as having a therapeutic activity for the multicellular organism in which they are expressed (e.g., via a nucleic acid encoding the peptide or polypeptide) include, but are not limited to: factor VIII, factor IX, β-globin, low-density lipoprotein receptor, adenosine deaminase, purine nucleoside phosphorylase, sphingomyelinase, glucocerebrosidase, cystic fibrosis transmembrane conductance regulator, α1-antitrypsin, CD-18, ornithine transcarbamylase, argininosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase; a neuroprotective factor, e.g. a neurotrophin (e.g. NGF, BDNF, NT-3, NT-4, CNTF), Kifap3, Bcl-xl, collapsin response mediator protein 1, Chkβ, calmodulin 2, calcyon, NPT1, Eef1a1, Dhps, Cd151, Morf412, CTGF, LDH-A, Atli, NPT2, Ehd3, Cox5b, Tubaia, γ-actin, Rpsa, NPG3, NPG4, NPG5, NPG6, NPG7, NPG8, NPG9, NPG10, dopamine, interleukins, cytokines, small peptides, the genes/proteins listed in Table 1 (see below: BCKDH complex (E1a, E1b and E2 subunits); Methylmalonyl-CoA Mutase; Propionyl-CoA Carboxylase (Alpha and Beta subunits); Isovaleryl CoA dehydrogenase; HADHA; HADHB; LCHAD; ACADM; ACADVL; G6PC (GSD1a); G6PT1(GSD1b); SLC17A3; SLC37A4 (GSD1c); Acid alpha-glucosidase; OCTN2; CPT1; CACT; CPT2; CPS1; ARG1; ASL; OTC; UGT1A1; FAH; COL7A1; COL17A1; MMP1; KRT5; LAMA3; LAMB3; LAMC2; ITGB4; and/or ATP7B), and the like. The above list of proteins refers to mammalian proteins, and in many embodiments human proteins, where the nucleotide and amino acid sequences of the above proteins are generally known to those of skill in the art.

TABLE 1

List of genes/proteins that are defective in various diseases

| Family of diseases | Diseases | Gene/protein |
|---|---|---|
| Branched-chain organic acidurias | Maple Syrup Urine Disease (MSUD) | BCKDH complex (E1a, E1b and E2 subunits) |
| | Methylmalonic Acidemia (MMA) | Methylmalonyl-CoA Mutase |
| | Propionic Acidemia (PA) | Propionyl-CoA Carboxylase (Alpha and Beta subunits) |
| | IsoValeric Acidemia (IVA) | Isovaleryl CoA dehydrogenase |
| Long chained fatty acid oxidation disorders | trifunctional protein deficiency | HADHA and HADHB |
| | LCHADD | LCHAD |
| | MCHADD | ACADM |
| | VLCHADD | ACADVL |

TABLE 1-continued

List of genes/proteins that are defective in various diseases

| Family of diseases | Diseases | Gene/protein |
|---|---|---|
| Glycogen storage disease | GSD1 | G6PC (GSD1a), G6PT1 (GSD1b), SLC17A3 or SLC37A4 (GSD1c) |
| | GSD2 | Acid alpha-glucosidase |
| Carnitine cycle disorders | | OCTN2<br>CPT1<br>CACT<br>CPT2 |
| Urea cycle disorders | | CPS1<br>ARG1<br>ASL<br>OTC |
| | Crigler-Najjar syndrome | UGT1A1 |
| | Heraditary Tyrosinemia | FAH |
| | Epidermolysis Bullosa | COL7A1 or COL17A1 or MMP1 or KRT5 or LAMA3 or LAMB3 or LAMC2 or ITGB4 |
| | Wilson Disease | ATP7B |

In other instances, the transgene encodes for an RNA that does not encode a protein, e.g. the nucleic acid encodes for a ribozyme, a small hairpin RNA (shRNA), a microRNA (miRNA), or a precursor thereof. As used herein, the term "microRNA" refers to any type of interfering RNAs, including but not limited to, endogenous microRNAs and artificial microRNAs (e.g., synthetic miRNAs). Endogenous microRNAs are small RNAs naturally encoded in the genome which are capable of modulating the productive utilization of mRNA. An artificial microRNA can be any type of RNA sequence, other than endogenous microRNA, which is capable of modulating the activity of an mRNA. A microRNA sequence can be an RNA molecule composed of any one or more of these sequences. MicroRNA (or "miRNA") sequences have been described in publications such as Lim, et al., 2003, Genes & Development, 17, 991-1008, Lim et al., 2003, Science, 299, 1540, Lee and Ambrose, 2001, Science, 294, 862, Lau et al., 2001, Science 294, 858-861, Lagos-Quintana et al., 2002, Current Biology, 12, 735-739, Lagos-Quintana et al., 2001, Science, 294, 853-857, and Lagos-Quintana et al., 2003, RNA, 9, 175-179. Examples of microRNAs include any RNA that is a fragment of a larger RNA or is a miRNA, siRNA, stRNA, sncRNA, tncRNA, snoRNA, smRNA, shRNA, snRNA, or other small non-coding RNA. See, e.g., US Patent Applications 20050272923, 20050266552, 20050142581, and 20050075492. A "microRNA precursor" (or "pre-miRNA") refers to a nucleic acid having a stem-loop structure with a microRNA sequence incorporated therein. A "mature microRNA" (or "mature miRNA") includes a microRNA that has been cleaved from a microRNA precursor (a "pre-miRNA"), or that has been synthesized (e.g., synthesized in a laboratory by cell-free synthesis), and has a length of from about 19 nucleotides to about 27 nucleotides, e.g., a mature microRNA can have a length of 19 nt, 20 nt, 21 nt, 22 nt, 23 nt, 24 nt, 25 nt, 26 nt, or 27 nt. A mature microRNA can bind to a target mRNA and inhibit translation of the target mRNA.

Other examples of therapeutic agents that may be integrated into a target locus include (i.e., the integrated transgene encodes) agents that promote immunoprophylaxis (also referred to as vectored immunoprophylaxis, or VIP). Examples of agents that promote immunoprophylaxis include, but are not limited to: antibodies or chimeric polypeptides comprising an immunoglobulin domain and an immune effector domain. As non-limiting examples, agents that promote immunoprophylaxis can include neutralizing antibodies, or chimeric polypeptides, specific for a pathogen selected from: human immunodeficiency virus (HIV), influenza virus, Respiratory Syncytial Virus (RSV), Hepatitis C virus (HCV), a *plasmodium* (e.g., *Plasmodium falciparum*, *Plasmodium malariae*, and the like), fungal or bacterial pathogens, and the like. For example, agents that promote immunoprophylaxis can include neutralizing antibodies, or chimeric polypeptides, that target epitopes conserved among strains of: human immunodeficiency virus (HIV), influenza virus, Respiratory Syncytial Virus (RSV), Hepatitis C virus (HCV), a *plasmodium* (e.g., *Plasmodium falciparum*, *Plasmodium malariae*, and the like), fungal or bacterial pathogens, and the like.

In some instances, the therapeutic agent alters the activity of the cell in which the agent is expressed. In other words, the agent has a cell-intrinsic effect. For example, the agent may be an intracellular protein, transmembrane protein or secreted protein that, when expressed in a cell, will substitute for, or "complement", a mutant protein in the cell. In other instances, the therapeutic agent alters the activity of cells other than cells in which the agent is expressed. In other words, the agent has a cell-extrinsic effect. For example, the integrated gene of interest may encode a cytokine, chemokine, growth factor, hormone, antibody, or cell surface receptor that modulates the activity of other cells.

The subject methods and compositions may be applied to any disease, disorder, or natural cellular process that would benefit from modulating cell activity by integrating a transgene of interest. For example, the subject methods and compositions find use in treating genetic disorders. Any genetic disorder that results from a defined genetic defect (e.g., a disorder with a single gene defect, a disorder with 2 defective genes, 3 defective genes, 4 defective genes, 5 defective genes, 2 or more defective genes, 3 or more defective genes, 4 or more defective genes, 5 or more defective genes, etc.) may be treated by the subject compositions and methods. The defect may result from one or more mutations in a single gene (e.g. 1, 2, 3, 4, 5, or more mutations), or may result from one or more mutations in 2 or more genes (e.g., 3 or more genes, 4 or more genes, 5 or more genes, 2 genes, 3 genes, 4 genes, 5 genes, etc.). Non-limiting examples of diseases resulting from genetic defects include: hemophilia (e.g., hemophilia A, hemophilia B), branched-chain organic acidurias (e.g., Maple syrup urine disease (MSUD), isovaleric acidaemia (IVA), propionic aciduria (PA) and methylmalonic aciduria (MMA), 3-methylcrotonyl glycinuria, 3-methylglutaconic Aciduria Type I, Short/branched-chain Acyl-CoA Dehydrogenase Deficiency, 2-methyl-3-hydroxybutyryl-CoA Dehydrogenase Deficiency, Isobutyryl-CoA Dehydrogenase Deficiency, 3-Hydroxyisobutyric Aciduria, Malonic Aciduria, etc.), long chained fatty acid oxidation disorders, glycogen storage diseases (e.g., glycogen storage disease type I (GSD1), glycogen storage disease type II, glycogen storage disease type III, glycogen storage disease type IV, glycogen storage disease type V, glycogen storage disease type VI, glycogen storage disease type VII, glycogen storage disease type VIII, glycogen storage disease type IX, glycogen storage disease type X, glycogen storage disease type XI, glycogen storage disease type XII, glycogen storage disease type 0, etc.), carnitine cycle disorders, urea cycle disorders, Crigler-Najjar syndrome, Heradiatary Tyrosinemia, Epidermolysis Bullosa, Wilson Disease, adenosine deaminase deficiency, sickle cell disease, X-Linked Severe Combined Immunodeficiency (SCID-X1), thalassemia, cystic fibrosis, alpha-1 anti-trypsin deficiency, diamond-blackfan anemia, Gaucher's disease, growth hormone deficiency, and the like.

As another example, the subject methods and compositions find use in treating nervous system conditions and to protect the CNS against nervous system conditions, e.g. neurodegenerative diseases, including, for example, e.g. Parkinson's Disease, Alzheimer's Disease, Huntington's Disease, Amyotrophic Lateral Sclerosis (ALS), Spielmeyer-Vogt-Sjögren-Batten disease (Batten Disease), Frontotemporal Dementia with Parkinsonism, Progressive Supranuclear Palsy, Pick Disease, prion diseases (e.g. Creutzfeldt-Jakob disease), Amyloidosis, glaucoma, diabetic retinopathy, age related macular degeneration (AMD), and the like); neuropsychiatric disorders (e.g. anxiety disorders (e.g. obsessive compulsive disorder), mood disorders (e.g. depression), childhood disorders (e.g. attention deficit disorder, autistic disorders), cognitive disorders (e.g. delirium, dementia), schizophrenia, substance related disorders (e.g. addiction), eating disorders, and the like); channelopathies (e.g. epilepsy, migraine, and the like); lysosomal storage disorders (e.g. Tay-Sachs disease, Gaucher disease, Fabry disease, Pompe disease, Niemann-Pick disease, Mucopolysaccharidosis (MPS) & related diseases, and the like); autoimmune diseases of the CNS (e.g. Multiple Sclerosis, encephalomyelitis, paraneoplastic syndromes (e.g. cerebellar degeneration), autoimmune inner ear disease, opsoclonus myoclonus syndrome, and the like); cerebral infarction, stroke, traumatic brain injury, and spinal cord injury.

As another for example, the subject methods and compositions may be used in the treatment of medical conditions and diseases in which it is desirable to ectopically express a therapeutic agent to promote tissue repair, tissue regeneration, or protect against further tissue insult, e.g. to promote wound healing; promote the survival of the cell and/or neighboring cells, e.g. in degenerative disease, e.g. neurodegenerative disease, kidney disease, liver disease, etc.; prevent or treat infection, etc.

Other examples of how the subject methods may be used to treat medical conditions are disclosed elsewhere herein, or would be readily apparent to the ordinarily skilled artisan.

The subject methods and compositions also find us in imaging cells of interest, e.g. cells comprising an integrated gene of interest. As such, the transgene (or one of the transgenes) to be integrated may encode for an imaging marker. By an "imaging marker" it is meant a non-cytotoxic agent that can be used to locate and, optionally, visualize cells, e.g. cells that have been targeted by compositions of the subject application. An imaging moiety may require the addition of a substrate for detection, e.g. horseradish peroxidase (HRP), β-galactosidase, luciferase, and the like. Alternatively, an imaging moiety may provide a detectable signal that does not require the addition of a substrate for detection, e.g. a fluorophore or chromophore dye, e.g. Alexa Fluor 488® or Alexa Fluor 647®, or a protein that comprises a fluorophore or chromophore, e.g. a fluorescent protein. As used herein, a fluorescent protein (FP) refers to a protein that possesses the ability to fluoresce (i.e., to absorb energy at one wavelength and emit it at another wavelength). For example, a green fluorescent protein (GFP) refers to a polypeptide that has a peak in the emission spectrum at 510 nm or about 510 nm. A variety of FPs that emit at various wavelengths are known in the art. FPs of interest include, but are not limited to, a green fluorescent protein (GFP), yellow fluorescent protein (YFP), orange fluorescent protein (OFP), cyan fluorescent protein (CFP), blue fluorescent protein (BFP), red fluorescent protein (RFP), far-red fluorescent protein, or near-infrared fluorescent protein and variants thereof.

As another example, the subject methods and compositions find use in isolating cells of interest, e.g. cells comprising an integrated transgene. Towards this end, the transgene (or one of the transgenes) to be integrated may encode for a selectable marker. By a "selectable marker" it is meant an agent that can be used to select cells, e.g. cells that have been targeted by compositions of the subject application. In some instances, the selection may be positive selection; that is, the cells are isolated from a population, e.g. to create an enriched population of cells comprising the genetic modification. In other instances, the selection may be negative selection; that is, the population is isolated away from the cells, e.g. to create an enriched population of cells that do not comprise the genetic modification. Any convenient selectable marker may be employed, for example, a drug selectable marker, e.g. a marker that prevents cell death in the presence of drug, a marker that promotes cell death in the presence of drug, an imaging marker, etc.; an imaging marker that may be selected for using imaging technology, e.g. fluorescence activated cell sorting; a polypeptide or peptide that may be selected for using affinity separation techniques, e.g. fluorescence activated cell sorting, magnetic separation, affinity chromatography, "panning" with an affinity reagent attached to a solid matrix, etc.; and the like.

In some instances, the transgene may be conjugated to a coding domain that modulates the stability of the encoded protein, e.g. in the absence/presence of an agent, e.g. a cofactor or drug. Non-limiting examples of destabilizing domains that may be used include a mutant FRB domain that is unstable in the absence of rapamycin-derivative C20-MaRap (Stankunas K, et al. (2003) Conditional protein alleles using knockin mice and a chemical inducer of dimerization. Mol Cell. 12(6):1615-24); an FKBP12 mutant polypeptide that is metabolically unstable in the absence of its ligand Shield-1 (Banaszynski L A, et al. (2006) A rapid, reversible, and tunable method to regulate protein function in living cells using synthetic small molecules. Ce11.126 (5):995-1004); a mutant *E. coli* dihydrofolate reductase (DHFR) polypeptide that is metabolically unstable in the absence of trimethoprim (TMP) (Mari Iwamoto, et al. (2010) A general chemical method to regulate protein stability in the mammalian central nervous system. Chem Biol. 2010 Sep. 24; 17(9): 981-988); and the like.

As discussed above, any nucleic acid sequence that the ordinarily skilled artisan would like expressed in a cell may be integrated into a target locus, for example, any nucleic acid sequence encoding a non-coding RNA such as, e.g., a ribozyme, siRNA, shRNA, miRNA, or long-noncoding RNA; or any nucleic acid sequence encoding an RNA coding for a peptide or polypeptide, may be integrated. In some instances, more than one sequence to be expressed may be integrated, for example, two or more polynucleotides of interest may be integrated, three or more polynucleotides may be integrated, four or more polynucleotides may be integrated, e.g. five or more polynucleotides may be integrated. Thus, for example, a therapeutic gene and an imaging marker may be integrated; a therapeutic gene and a non-coding RNA may be integrated; a therapeutic gene and a selectable marker may be integrated, an imaging marker and a selectable marker may be integrated, a therapeutic gene, an imaging marker and a selectable marker may be integrated, and so forth.

Reagents, Devices and Kits

Also provided are reagents, devices and kits thereof for practicing one or more of the above-described methods. The subject reagents, devices and kits thereof may vary greatly.

In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Example 1

In Vivo Gene-Targeting without Nucleases Facilitates Therapeutic Levels of hF-IX Following AAV8 Vector Injections of Either Neonate or Adult Mice.

Achieving therapeutic levels of site-specific gene targeting is often assumed to require the use of endonucleases (e.g. CRISPR, TALEN, ZFN) which are associated with off-target effects. In particular, delivery of endonuclease-coding vectors for in-vivo applications may lead to adverse immune consequences as well as to genotoxicity stemming from sustained expression. Avoiding the use of nucleases, we performed in vivo, AAV8 vector mediated targeting of a promoter-less hF-IX gene to the Albumin locus for the treatment of Hemophilia B. The promoter-less hF-IX gene, preceded by a sequence coding a 2A-peptide, is flanked by homology arms targeting its integration as a DNA fusion to the Albumin ORF. hF-IX expression is therefore linked to the robust Albumin expression at the levels of transcription, RNA processing, localization and stability, translation initiation and ER localization. The 2A peptide induces ribosomal skipping, thus Albumin is tagged but not disrupted. Off-target integration is minimized by refraining from using nucleases, and the lack of vector-borne promoter diminishes the risk of neighboring-oncogene activation by rare off-target integration.

First, we performed IP injections of 2-day old B6 mice with 2.5e11 Vg per mouse of an AAV8 vector coding for the hF-IX targeting cassette. We then followed plasma hF-IX levels weekly, starting at week 4 of life. Levels of plasma hF-IX plateaued at ~10% of normal, which corresponds to significant disease amelioration if translated to the clinic. Importantly, hF-IX plasma levels rebounded to their original level soon after a ⅔ partial hepatectomy, thus establishing stable transgene integration. We validated that hF-IX expression originates essentially entirely from on-target integration by performing RT followed by linker ligation, unbiased PCR and sequencing. In particular, this method did not detect any hF-IX expression from the episome nor from any off-target integration. Further corroboration comes from overlapping Western blot signals when using either an anti-2A-peptide or an anti-Albumin antibody. Northern blot using an anti-hF-IX probe reveals a single band at the expected size of an Albumin-hF-IX fused mRNA. Next, we checked whether liver cell division, associated with neonates, is essential for therapeutic levels of gene-targeting. We performed tail vain injection of adult mice with 1e12 Vg per mouse of our AAV8 vector. Weekly monitoring of hF-IX levels revealed stable expression at 15% of normal. We are currently repeating these studies in hemophilia B mice and are using qPCR, IHC and NGS to quantify the rate of on-target integration and the distribution of off-target integration.

In conclusion, the AAV mediated in vivo non-disruptive and promoter-less gene targeting method is applicable to both neonates and adults. Targeting transgene integration as a 2A-fusion to a highly expressed endogenous gene may obviate the requirement for nucleases, thus diminishing off-target effect, while allowing therapeutic levels of transgene expression.

Example 2

Methods

For vector construction, a fragment of Alb genomic DNA spanning the stop codon was first inserted between AAV2 ITRs on a pTRUF plasmid backbone (Lisowski et al. Molecular therapy: the journal of the American Society of Gene Therapy 20, 1912-1923, 2012). P2A coding sequence and hF9 cDNA were then inserted in a nested fashion. For the inverse control, a central segment was cleaved out and integrated back in the opposite orientation. rAAV8 was produced in HEK293 cells and titered by dot blot. 2-day-old B6 mice were injected intraperitonealy with 2.5e11 vg of rAAV8 (hF9 or inverse) and bled weekly beginning at week 4 of life by retro-orbital bleeding for ELISA. Adult B6 mice received either tail vein injections of 1e12 vg of rAAV8 (hF9 or inverse) or hydrodynamic injections of 3.5e12 vg plasmid, and were similarly bled weekly for ELISA. ⅔ partial hepatectomies (PH) were performed according to established protocols. Liver tissues for DNA, RNA and protein analysis as well as IHC were collected at PH and upon sacrificing mice. Frozen liver tissue for hF9 IHC were sectioned and stained according to established protocols. TaqMan qPCR assays, Northern and Western blots used established protocols. aPTT assays were performed on haemophilia B knockout mice as previously described (Shi et al., Gene therapy 20, 987-996, 2013).

Results

Recombinant adeno-associated virus (rAAV) mediated promoterless gene targeting was performed without nucleases to ameliorate the bleeding diathesis in haemophilia B mice. In particular, a promoterless human coagulation factor IX (hF9) gene was targeted to the liver-expressed albumin (Alb) locus. hF9 was targeted, along with a preceding 2A-peptide coding sequence, to be integrated just upstream to the Alb stop codon. While hF9 was fused to Alb at the DNA and RNA levels, two separate proteins were synthesized by way of ribosomal skipping. Thus, hF9 expression was linked to robust hepatic albumin expression without disrupting it. An AAV8-hF9 vector was injected into neonatal and adult mice to achieve on target integration into ~0.5% of the albumin alleles in hepatocytes. It was established that hF9 was produced from on-target integration only and ribosomal skipping was highly efficient. Stable hF9 plasma levels of 7-20% of normal, were obtained, and treated factor IX deficient mice had normal coagulation times. Transgene integration as a 2A-fusion to a highly expressed endogenous gene obviated the requirement for nucleases and/or vector-borne promoters. This example method allows for safe and efficacious gene targeting in both infants and adults by greatly diminishing off-target effects while still providing therapeutic levels of expression from integration.

The hF9 gene, which is deficient in the X-linked recessive disease haemophilia B affecting 1/30,000 males, was targeted. Affected individuals suffer from serious spontaneous bleeding due to a deficiency of plasma coagulation factor IX produced from the liver. Reconstitution with as little as 1-2% clotting factor can significantly improve quality of life, while 5-20% will markedly ameliorate the bleeding diathesis. The liver tropic rAAV8 serotype was used to target hF9 for expression upon integration from the robust liver-specific Alb promoter. We postulated that: (1) the Alb promoter should allow high levels of coagulation factor production even if integration takes place in only a small fraction of hepatocytes; and (2) the high transcriptional activity at the Alb locus might make it more susceptible to transgene integration by homologous recombination.

Gene targeting without nucleases should affect only a small fraction of Alb alleles in the liver. Nevertheless, we opted to minimize disruption and dysregulation of the Alb gene by targeting hF9 as a 2A-fusion at the end of the Alb reading frame (FIG. 8A). 2A-peptides, derived from plus-strand RNA viruses, allow the production of multiple proteins from a single reading frame by means of ribosomal skipping (Kim, J. H. et al. High cleavage efficiency of a 2A peptide derived from porcine teschovirus-1 in human cell lines, zebrafish and mice. *PloS one* 6, e18556, doi:10.1371/journal.pone.0018556 (2011). This process leaves the first translated protein tagged with ~20 C-terminal amino acids, and the second protein with just one additional N-terminal proline. Functionality of both proteins is typically retained, and clinical trials using 2A-peptides did not report immunogenicity. Single stranded AAV were used to target a codon-optimized hF9 cDNA, preceded by a sequence coding for a porcine teschovirus-1 2A-peptide (P2A), to be integrated just 5' of the Alb stop codon. Following integration, Alb and hF9 are co-transcribed from the strong Alb promoter and should thus be co-regulated at the levels of splicing, nuclear exit, mRNA stability, translation initiation and ER localization. Two separate proteins were translated, both containing a signal peptide, so that the ER-associated translation of Alb was be immediately followed by translation and processing of the clotting factor for secretion. Finally, in order to further reduce the chance of off-target hF9 expression, the vector has neither an ATG start codon before the hF9 signal peptide, nor a start codon in the 2A-peptide coding sequence or preceding Alb exon.

First, intra-peritoneal (IP) injections of 2-day old C57BL/6 (B6) mice were performed with 2.5e11 vector genomes (vg) per mouse of a rAAV8 coding for the hF9 targeting cassette or an inverse control (FIG. 8B). The fragment inverted in the control with respect to the Alb homology arms included not only the hF9 gene, but also the P2A coding sequence, the adjacent Alb exon and the preceding splice junction. The inverse control should not allow significant hF9 expression upon on-target integration, but would allow levels of off-target expression similar to that from the experimental construct (Episomal expression is controlled for by other means, below). Plasma hF9 Protein levels were measured weekly by enzyme-linked immunosorbent assay (ELISA), starting at week 4 of life (FIG. 9A). For the experimental group, levels of plasma hF9 plateaued at 350-1000 ng/mL, which corresponds to 7-20% of normal. For the inverse control group, hF9 plasma levels were at or below the level of detection (20 ng/mL), implying that in the experimental group, hF9 expression did indeed originate from on-target integration. hF9 retained the original plasma protein levels after a ⅔ partial hepatectomy, a surgical procedure known to reduce episomal AAV transgene expression by >90%, further establishing stable transgene integration.

Figure 12:
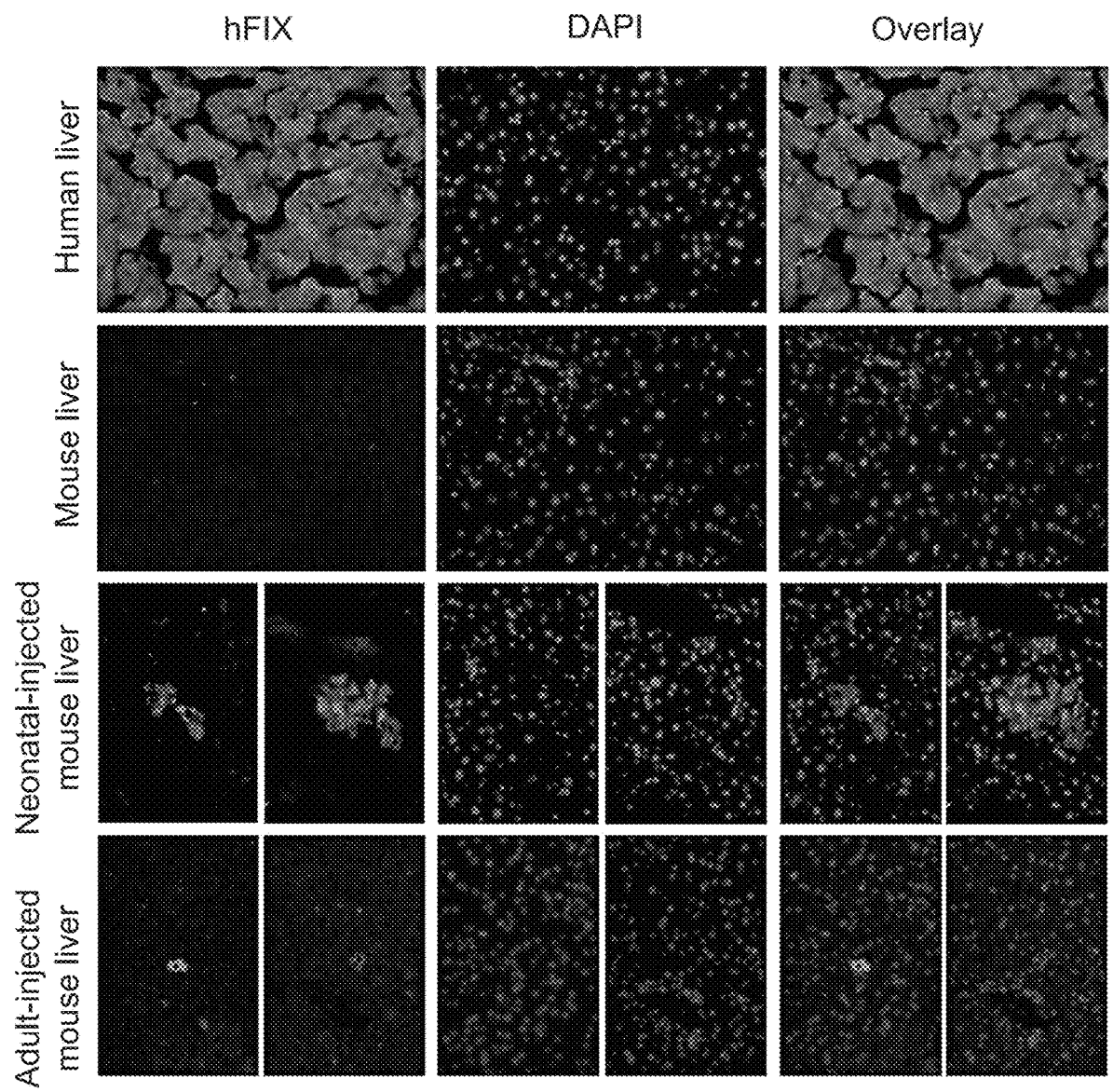
FIG. 12. hF9 liver immunohistochemistry. From top to bottom, panels show human factor 9 staining (red) with DAPI nuclear counterstain (blue) in positive control human liver, negative control untreated mouse liver, and two representative stains from mice treated as neonates or adults with AAV8-P2A-hF9.
Figure 15:
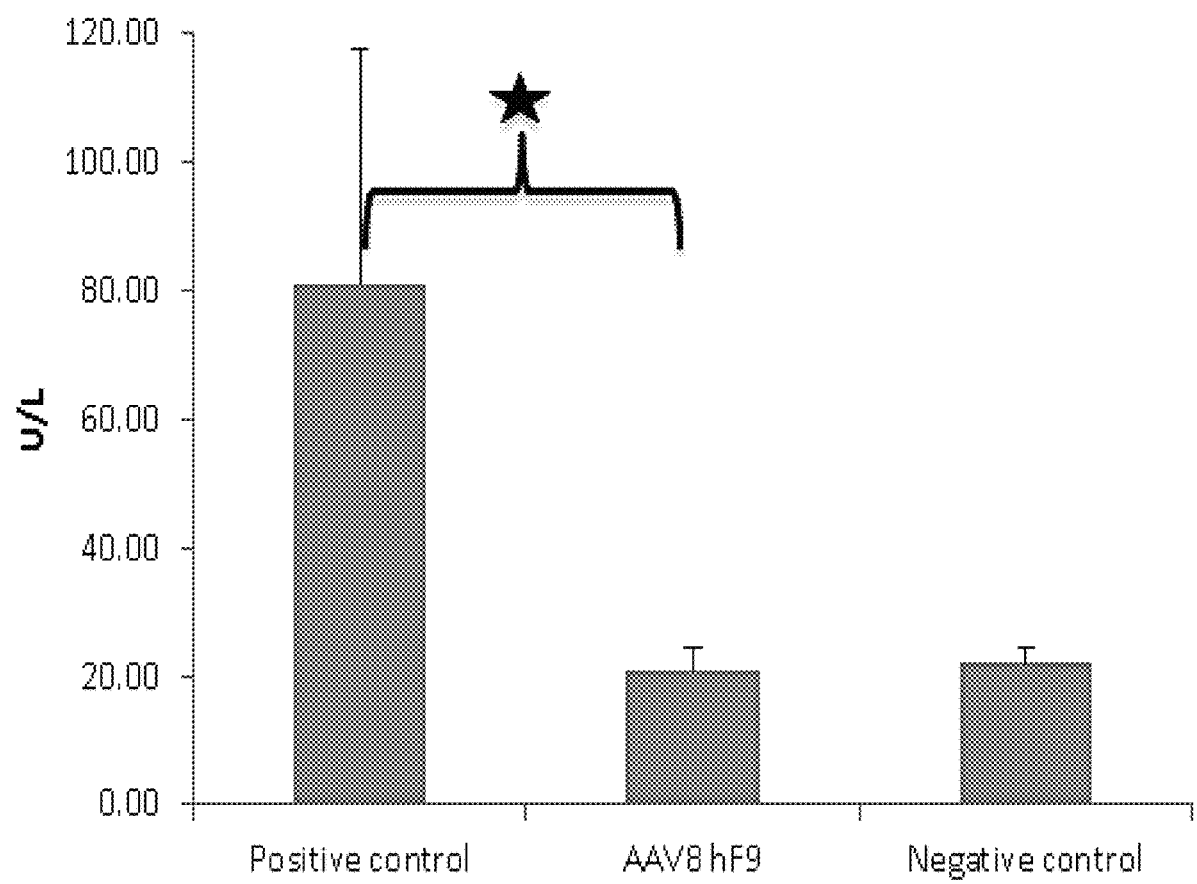
FIG. 15. Toxicity assessment by ALT measurement. Alanine transaminase levels (ALT) were evaluated 7 days post-injection in mice injected with AAV8 coding for our experimental vector (1e12) or a negative control coding for a known non-toxic cassette (1e12 of H1 promoter-driven shRNA), or a positive control coding for a known toxic cassette (5e11 of U6 promoter-driven shRNA). Data represent mean of two measurements of four independent mice for each groups. The statistical significance is defined here as having p<0.05 in a one-tailed t test between samples of different variance.

In order to determine whether liver growth, as seen with neonates, is essential for therapeutic levels of gene targeting, hF9 was targeted to the Alb locus using the same vector in adult mice. Adult B6 mice were injected with $1 \times 10^{12}$ vg per mouse (approximately 5e13 per Kg) by tail vein with the rAAV8 vector, or the inverse control. A third group of mice received hydrodynamic tail vain injections of a plasmid coding for the promoterless hF9 construct in the "correct" orientation. For the rAAV hF9 mice group, plasma hF9 levels were found to be stable at 7-20% of normal (FIG. 9B). Vector injections at lower MOI led to lower plasma hF9 levels with no plateau to imply an upper-threshold effect (FIG. 9C). For adults as well as for neonates, the hF9 plasma levels of the inverse control group were at or below the limit of detection. Diminished hF9 plasma levels were also associated with mice hydrodynamically injected with plasmid. Thus, significant targeting is dependent on rAAV vectorization. Finally, rAAV injections were performed in adult F9 knockout (KO) haemophilia B mice. The functional coagulation, as determined by the activated partial thromboplastin time (aPTT) in treated KO mice, was restored to levels similar to that of wild-type mice (FIG. 9D). The hF9 biological activity correlated with plasma protein levels of 709±91 ng/mL, similar to levels in wild-type mice (FIG. 9B-D).

hF9 expression from the liver was confirmed by immunohistochemistry (IHC) (FIG. 12). Western blot analysis of liver samples detected hF9 at the expected molecular weight, testifying that ribosomal skipping was efficient, and implying that both the ELISA and IHC signals correspond to a accurately processed hF9 (FIG. 9E).

hF9 is a secreted protein. Hence, the IHC signal was sparse and could not be used for quantitation of targeting rates. Instead, qPCR was used to quantitatively assess the rate of Alb targeting by hF9. To avoid false signals from episomal rAAV, a 3' segment of the genomic Alb locus was first amplified in a manner not affected by presence or absence of an integrated hF9 sequence (FIG. 10a, FIG. 13). The unbiased amplification was made possible by presence of a common restriction site at a roughly equal distance 3' of the stop codon in targeted and wild-type alleles. The PCR amplicon was then used as a template for two different qPCR assays: one quantifying the abundance of targeted Alb alleles, and the other quantifying the abundance of untargeted wild-type alleles. In the liver, only hepatocytes are targeted by rAAV8 (Nakai, H. et al. Unrestricted hepatocyte transduction with adeno-associated virus serotype 8 vectors in mice. *J Virol* 79, 214-224, doi:10.1128/JVI.79.1.214-224.2005 (2005). Therefore, we conservatively corrected for a 70% hepatocyte frequency and found the rate of Alb alleles targeted by hF9 to be 0.5% on average for mice injected as either neonates or adults (FIG. 10c and associated standard curves in FIG. 14). The proportion of fused Alb_hF9 mRNAs to wild-type Alb mRNAs was then examined by comparing two respective qPCR assays performed on an unbiased cDNA template (FIG. 10B). The proportion was found to be 0.1% on average for mice injected as either neonates or adults (FIG. 10C). This value tended to be lower than the rate of integration at the DNA level, although the difference was not statistically significant. It is possible that the production, processing and/or stability of chimeric hF9-Alb mRNA transcripts were reduced compared to wild-type Alb mRNA. It is also possible that some integration occurred at non-parenchymal cells who do not express Albumin. The observed targeting rate is higher than previously reported (Miller, D. G. et al. Gene targeting in vivo by adeno-associated virus vectors. *Nature biotechnology* 24, 1022-1026, doi:10.1038/nbt1231 (2006); Paulk, N. K., Loza, L. M., Finegold, M. J. & Grompe, M. AAV-mediated gene targeting is significantly enhanced by transient inhibition of nonhomologous end joining or the proteasome in vivo. *Human gene therapy* 23, 658-665, doi:10.1089/hum.2012.038 (2012)), and is particularly noteworthy in adult mice where non-proliferating cells were expected to allow for a low rate of homologous recombination. We hypothesize that the high expression rate of the Alb locus and the associated chromatin status may contribute to the high rates of targeting. Damage induced proliferation cannot be strictly ruled out, but no elevation in ALT levels were seen following injection (FIG. 15).

Figure 16:
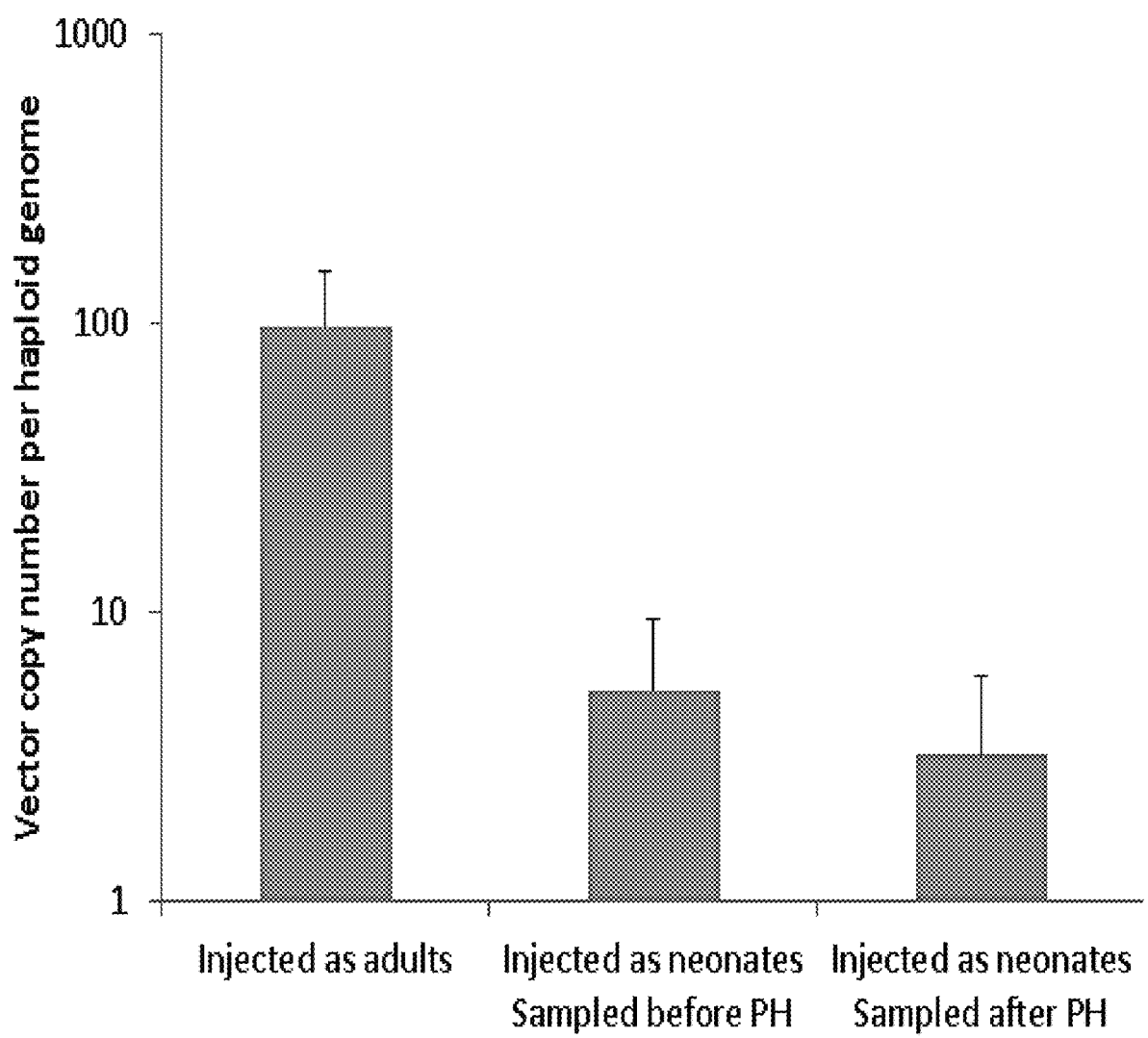
FIG. 16. Vector copy number. Vector copy number assessed by qPCR using primers 8 and 9 (FIG. 3). N=7 for mice injected as adults and N=6 for mice injected as neonates and analyzed before or after partial hepatectomy. Error bars represent standard deviation.

AAV vector may be present in cells as episomes or as on-target or off-target integrant. The total vector copy number was assessed by qPCR (FIG. 16). The relatively minor change in vector copy number following partial hepatectomy in mice injected as neonates may imply that episomal vector has already been greatly diluted. In which case, the vector copy number could be seen as an approximated lower bound on the rate of off target to on target integration. However, in the absence of a vector-borne promoter, hF9 should only be expressed from on-target integration. The reconstituted high hF9 levels following partial hepatectomy (FIG. 9A) support this assumption as only stably integrated transgenes could rebound after such a procedure, unlike that seen with transient episomal expression. Lack of significant hF9 plasma levels following treatment with the inverse control vector further demonstrated reduced off-target expression. We used RT-qPCR to directly assess the ratio of fused Alb_hF9 mRNAs among the total hF9 mRNA pool (FIG. 11A). The ratio was found to be 1:1 for mice injected as neonates as well as for mice injected as adults (FIG. 11B). This implies that hF9 is expressed almost exclusively from on-target integration. Indeed, the only specific signal from a Northern blot with a P2A probe corresponded to the expected fused Alb-P2A-hF9 mRNA (FIG. 11C). Finally, a Western blot with an anti-2A-peptide antibody indicated the 2A-peptide is associated with a single species at the expected molecular weight of Alb (FIG. 11D), as would be expected only if expression was restricted to on-target integration and was followed by efficient ribosomal skipping.

rAAV has become a popular vector for clinical therapy. While the period of transgene expression in adults can last for at least a couple of years, it is not yet known whether lifelong expression, as required for many genetic disorders, can be obtained with routine promoter-containing vectors. Episomal expression from AAV vectors is rapidly lost, even after one round of cell division. This makes it likely that diseases that induce cellular regeneration and/or are treated in infancy while tissues continue to grow, will have limited expression. Secondary infusion of an AAV vector will unlikely result in secondary transduction, due to the robust humoral immunity resulting from the primary vector administration. In contrast, the approach described herein results in vector integration that would eliminate loss of expression over time, even in growing tissues. This however relies on the choice of appropriate AAV serotypes to avoid neutralization by pre-existing immunity.

Previous work demonstrating targeting of hF9 to a chimeric locus in a transgenic mouse (Li, H. et al. In vivo genome editing restores haemostasis in a mouse model of haemophilia. *Nature* 475, 217-221, doi:10.1038/nature10177 (2011)) have relied on co-expression of nucleases that may be associated with immunological and genotoxic side effects. The same reliance on endonucleases held true even when hF8 was targeted to the Alb locus in mice and non-human primates (Anguela, X. e. a. ZFN Mediated Targeting Of Albumin "Safe Harbor" Results In Therapeutic Levels Of Human Factor VIII In a Mouse Model Of Hemophilia A. *Blood* 122, 720 (2013)), probably because no homology arms were provided and integration relied instead on non-homologous end joining. rAAV has already been used in clinical gene therapy trials to treat Haemophilia B (Nathwani, A. C. et al. Adenovirus-associated virus vector-mediated gene transfer in hemophilia B. *The New England journal of medicine* 365, 2357-2365, doi:10.1056/NEJMoa1108046 (2011)). However, the transgene in these clinical trials was expressed from a vector-borne promoter that might induce oncogene activation, as has been reported in mice (Donsante, A. et al. AAV vector integration sites in mouse hepatocellular carcinoma. *Science* 317, 477, doi: 10.1126/science.1142658 (2007)). As assessed by measuring levels of alanine transaminases, no liver toxicity was observed with the injection of the hF9 targeting vector described herein (FIG. 15).

The work described here demonstrates a therapeutic effect for in vivo gene targeting without nucleases and without a vector-borne promoter. Genetic polymorphisms at the target locus in the human patient population could potentially lead to variable therapeutic efficacy due to reduced homology. However, we found that ~95% of a 1000 genome sample of the human population have no more than just two haplotypes at the relevant Alb sequence, thus demonstrating this approach to have broad applicability (FIG. 17).

The favorable safety profile of this promoterless and nuclease-free gene targeting strategy for rAAV makes it a prime candidate for treatment of haemophilia and other genetic deficiencies (Yew, N. S. & Cheng, S. H. Gene therapy for lysosomal storage disorders. *Pediatric endocrinology reviews: PER* 11 Suppl 1, 99-109 (2013)), More generally, this strategy could be applied whenever the therapeutic effect is conveyed by a secreted protein (e.g. broadly neutralizing antibodies) or when targeting confers a selective advantage (Paulk, N. K., Loza, L. M., Finegold, M. J. & Grompe, M. AAV-mediated gene targeting is significantly enhanced by transient inhibition of nonhomologous end joining or the proteasome in vivo. *Human gene therapy* 23, 658-665, doi:10.1089/hum.2012.038 (2012)).

Example 3

Figure 18:
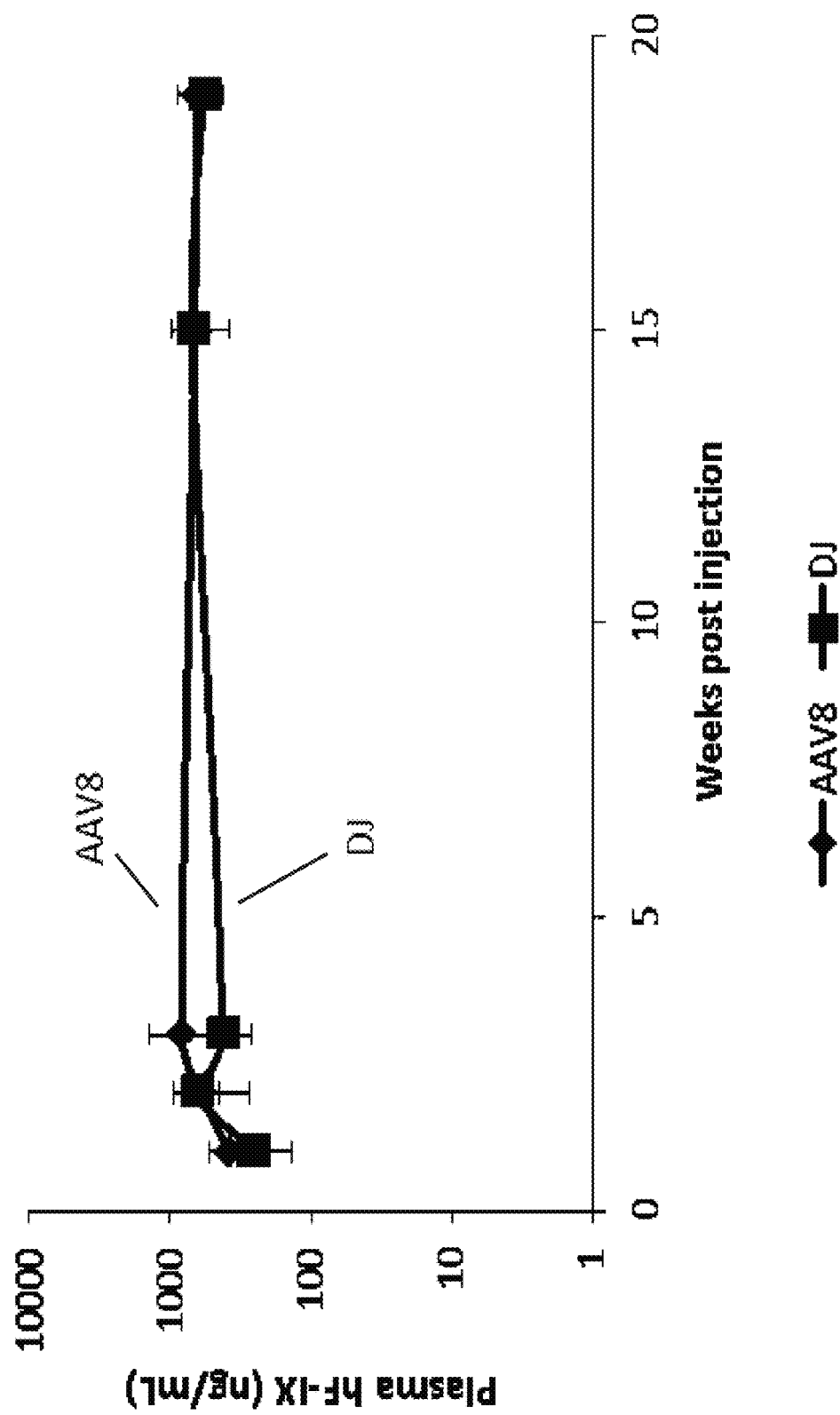
FIG. 18. Plasma F9 measured by ELISA after tail vein injections of 9-week-old female B6 mice with $1\times10^{12}$ vector genomes per mouse of the AAV8-F9 or AAVDJ-F9 experimental construct (n=4 each), Error bars represent standard deviation.

FIG. 18 provides data obtained by measuring plasma F9 (measured by ELISA) after tail vein injections of 9-week-old female B6 mice with $1 \times 10^{12}$ vector genomes per mouse of the AAV8-F9 or AAVDJ-F9 experimental construct (n=4 each).

FIG. 19 provides data obtained by measuring coagulation efficiency (by activated partial thromboplastin time (aPTT)) 2 weeks after tail vein injections of AAV8-F9 at $1 \times 10^{12}$ vector genomes per mouse (top) or of AAV8-F9 Triple at $3 \times 10^{11}$ vector genomes per mouse (bottom) (n=5 each).

Figure 20:
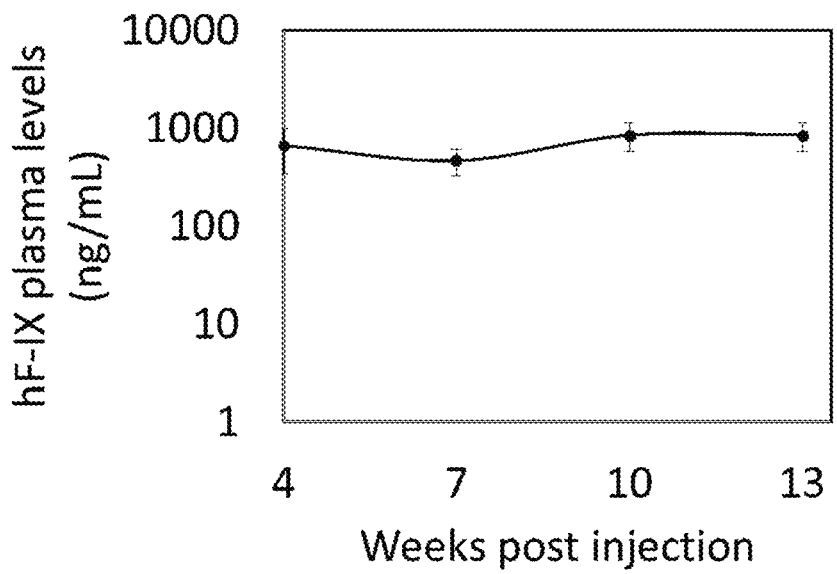
FIG. 20. Plasma F9 measured by ELISA following superficial temporal vein injections of 2-day-old B6 mice with $2.5\times10^{11}$ vector genomes per mouse of the AAV8-F9 experimental construct (n=4).

FIG. 20 provides data obtained by measuring plasma F9 (measured by ELISA) following superficial temporal vein injections of 2-day-old B6 mice with $2.5 \times 10^{11}$ vector genomes per mouse of the AAV8-F9 experimental construct (n=4).

Figure 21:
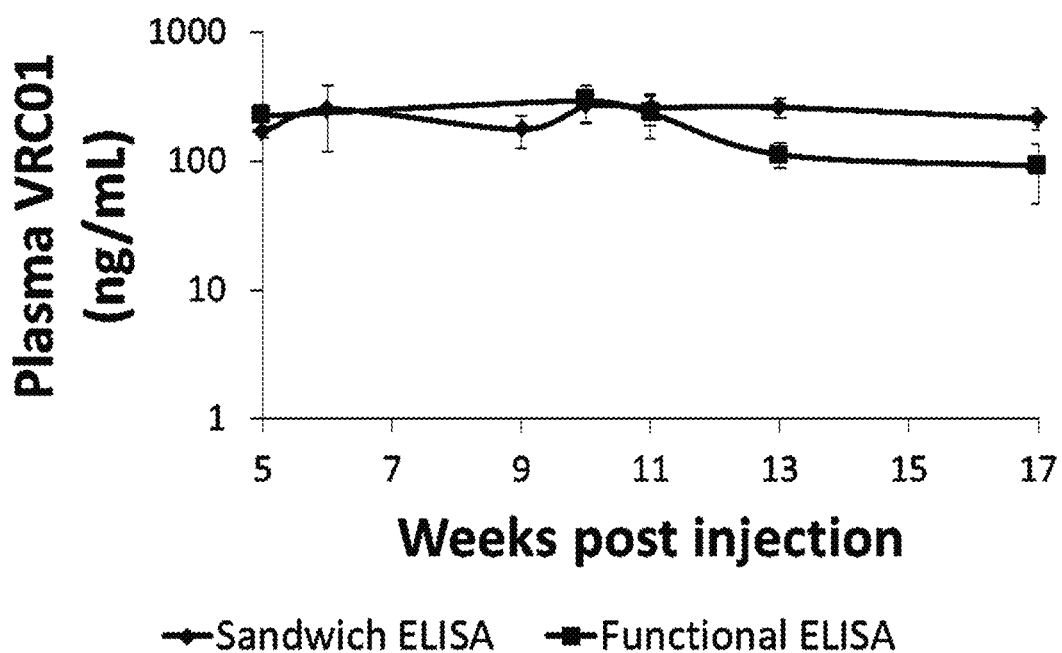
FIG. 21. Plasma VRC01 (broadly neutralizing antibody against HIV) measured by ELISA after tail vein injections of 9-week-old female B6 mice with $1\times10^{12}$ vector genomes per mouse of the AAV8-VRC01 experimental construct (n=4 each), Error bars represent standard deviation. Sandwich ELISA uses plates covered by antibodies against the constant region of human IgG whereas functional ELISA uses plates covered with the HIV glycoprotein gp120 which is the antigen recognized by the VRC01 antibody.

FIG. 21 provides data obtained by measuring plasma VRC01 (broadly neutralizing antibody against HIV) (measured by ELISA) after tail vein injections of 9-week-old female B6 mice with $1 \times 10^{12}$ vector genomes per mouse of the AAV8-VRC01 experimental construct (n=4 each). Sandwich ELISA used plates covered by antibodies against the constant region of human IgG whereas functional ELISA used plates covered with the HIV glycoprotein gp120 which is the antigen recognized by the VRC01 antibody.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. A recombinant viral vector comprising:
   a polynucleotide cassette comprising a first nucleic acid sequence and a second nucleic acid sequence, wherein the first nucleic acid sequence comprises a transgene and the second nucleic acid sequence is positioned 5' or 3' to the first nucleic acid sequence and promotes the production of two independent gene products upon integration into the target integration site in the genome of the cell;

a third nucleic acid sequence positioned 5' to the polynucleotide cassette and comprising a sequence that is homologous to a genomic sequence 5' of the target integration site in the genome of the cell; and a fourth nucleic acid sequence positioned 3' of the polynucleotide cassette and comprising a sequence that is homologous to a genomic sequence 3' of the target integration site in the genome of the cell, wherein the transgene comprises a nucleotide sequence encoding methylmalonyl-CoA mutase, propionyl-CoA carboxylase (alpha and beta subunits), G6PC, G6PT1, SLC17A3, SLC37A4, acid alpha-glucosidase, ATP7B, UGT1A1, fumarylacetoacetate hydrolase, a BCKDH complex, isovaleryl CoA dehydrogenase, CPS1, ARG1, ASL, or OTC.

2. The recombinant viral vector of claim 1, wherein the transgene comprises a nucleotide sequence encoding methylmalonyl-CoA mutase.

3. The recombinant viral vector of claim 1, wherein the transgene comprises a nucleotide sequence encoding propionyl-CoA carboxylase (alpha and beta subunits).

4. The recombinant viral vector of claim 1, wherein the transgene comprises a nucleotide sequence encoding G6PC.

5. The recombinant viral vector of claim 1, wherein the transgene comprises a nucleotide sequence encoding G6PT1.

6. The recombinant viral vector of claim 1, wherein the transgene comprises a nucleotide sequence encoding SLC17A3.

7. The recombinant viral vector of claim 1, wherein the transgene comprises a nucleotide sequence encoding SLC37A4.

8. The recombinant viral vector of claim 1, wherein the transgene comprises a nucleotide sequence encoding ATP7B.

9. The recombinant viral vector of claim 1, wherein the transgene comprises a nucleotide sequence encoding UGT1A1.

10. The recombinant viral vector of claim 1, wherein the transgene comprises a nucleotide sequence encoding fumarylacetoacetate hydrolase.

11. The recombinant viral vector of claim 1, wherein the transgene comprises a nucleotide sequence encoding a BCKDH complex.

12. The recombinant viral vector of claim 1, wherein the transgene comprises a nucleotide sequence encoding isovaleryl CoA dehydrogenase.

13. The recombinant viral vector of claim 1, wherein the transgene comprises a nucleotide sequence encoding CPS1.

14. The recombinant viral vector of claim 1, wherein the transgene comprises a nucleotide sequence encoding ARG1.

15. The recombinant viral vector of claim 1, wherein the transgene comprises a nucleotide sequence encoding ASL.

16. The recombinant viral vector of claim 1, wherein the transgene comprises a nucleotide sequence encoding OTC.

17. The recombinant viral vector of claim 1, wherein the transgene comprises a nucleotide sequence encoding acid alpha-glucosidase.

18. The recombinant viral vector of claim 1, wherein the second nucleic acid sequence comprises a sequence that encodes a 2A peptide.

19. The recombinant viral vector of claim 1, wherein the viral vector is an rAAV vector.

20. The recombinant viral vector of claim 1, wherein the target integration site is in an albumin gene.

21. A recombinant viral vector comprising:

a polynucleotide cassette comprising a first nucleic acid sequence and a second nucleic acid sequence, wherein the first nucleic acid sequence comprises a transgene comprising a nucleotide sequence encoding fumarylacetoacetate hydrolase and the second nucleic acid sequence is positioned 5' or 3' to the first nucleic acid sequence and comprises a sequence encoding a 2A peptide;

a third nucleic acid sequence positioned 5' to the polynucleotide cassette and comprising a sequence that is homologous to a genomic sequence 5' of the target integration site in the genome of the cell; and a fourth nucleic acid sequence positioned 3' of the polynucleotide cassette and comprising a sequence that is homologous to a genomic sequence 3' of the target integration site in the genome of the cell;

wherein:

the target integration site is in an albumin gene.

* * * * *

```
SEQUENCE LISTING

<160> NUMBER OF SEQ ID NOS: 7

<210> SEQ ID NO 1
<211> LENGTH: 6
<212> TYPE: PRT
<213> ORGANISM: Artificial sequence
<220> FEATURE:
<223> OTHER INFORMATION: Synthetic sequence

<400> SEQUENCE: 1

Leu Val Pro Arg Gly Ser
1               5

<210> SEQ ID NO 2
<211> LENGTH: 7
<212> TYPE: PRT
<213> ORGANISM: Artificial sequence
<220> FEATURE:
<223> OTHER INFORMATION: Synthetic sequence
<220> FEATURE:
<221> NAME/KEY: misc_feature
<222> LOCATION: (2)..(3)
<223> OTHER INFORMATION: Xaa can be any amino acid
<220> FEATURE:
<221> NAME/KEY: misc_feature
<222> LOCATION: (5)..(5)
<223> OTHER INFORMATION: Xaa can be any amino acid

<400> SEQUENCE: 2

Glu Xaa Xaa Tyr Xaa Gln Ser
1               5

<210> SEQ ID NO 3
<211> LENGTH: 4
<212> TYPE: PRT
```

```
<213> ORGANISM: Artificial sequence
<220> FEATURE:
<223> OTHER INFORMATION: Synthetic sequence
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: MISC_FEATURE
<222> LOCATION: (3)..(3)
<223> OTHER INFORMATION: X at this position is Lys or Arg

<400> SEQUENCE: 3

Arg Xaa Xaa Arg
1

<210> SEQ ID NO 4
<211> LENGTH: 5
<212> TYPE: PRT
<213> ORGANISM: Artificial sequence
<220> FEATURE:
<223> OTHER INFORMATION: Synthetic sequence

<400> SEQUENCE: 4

Asp Asp Asp Asp Lys
1               5

<210> SEQ ID NO 5
<211> LENGTH: 4
<212> TYPE: PRT
<213> ORGANISM: Artificial sequence
<220> FEATURE:
<223> OTHER INFORMATION: Synthetic sequence
<220> FEATURE:
<221> NAME/KEY: MISC_FEATURE
<222> LOCATION: (2)..(2)
<223> OTHER INFORMATION: X at this position is Glu or Asp

<400> SEQUENCE: 5

Ile Xaa Gly Arg
1

<210> SEQ ID NO 6
<211> LENGTH: 6
<212> TYPE: PRT
<213> ORGANISM: Artificial sequence
<220> FEATURE:
<223> OTHER INFORMATION: Synthetic sequence

<400> SEQUENCE: 6

Pro Gly Ala Ala His Tyr
1               5

<210> SEQ ID NO 7
<211> LENGTH: 8
<212> TYPE: PRT
<213> ORGANISM: Artificial sequence
<220> FEATURE:
<223> OTHER INFORMATION: Synthetic sequence

<400> SEQUENCE: 7

Leu Glu Val Leu Phe Gln Gly Pro
1               5
```